(12) United States Patent
Bondke et al.

(10) Patent No.: US 11,566,029 B2
(45) Date of Patent: *Jan. 31, 2023

(54) PYRAZOLO[1,5-A]PYRIMIDINE-5,7-DIAMINE COMPOUNDS AS CDK INHIBITORS AND THEIR THERAPEUTIC USE

(71) Applicants: CANCER RESEARCH TECHNOLOGY LIMITED, London (GB); IP2IPO INNOVATIONS LIMITED, London (GB); EMORY UNIVERSITY, Atlanta, GA (US)

(72) Inventors: Alexander Bondke, Caputh (DE); Sebastian Kroll, London (GB); Anthony Barrett, London (GB); Matthew Fuchter, London (GB); Brian Slafer, Lemont, IL (US); Simak Ali, London (GB); Charles Coombes, London (GB); James Patrick Snyder, Atlanta, GA (US)

(73) Assignees: IP2IPO Innovations Limited, London (GB); Emory University, Atlanta, GA (US); Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/175,780

(22) Filed: Feb. 15, 2021

(65) Prior Publication Data
US 2021/0253583 A1  Aug. 19, 2021

Related U.S. Application Data

(63) Continuation of application No. 16/559,735, filed on Sep. 4, 2019, now Pat. No. 10,927,119, which is a continuation of application No. 15/941,063, filed on Mar. 30, 2018, now Pat. No. 10,414,772, which is a continuation of application No. 15/117,982, filed as application No. PCT/GB2015/050494 on Feb. 20, 2015, now Pat. No. 9,932,344.

(30) Foreign Application Priority Data

Feb. 21, 2014  (GB) .................................... 1403093

(51) Int. Cl.
*A61K 31/519*  (2006.01)
*A61P 35/04*  (2006.01)
*C07D 487/04*  (2006.01)

(52) U.S. Cl.
CPC .......... *C07D 487/04* (2013.01); *A61K 31/519* (2013.01); *A61P 35/04* (2018.01)

(58) Field of Classification Search
CPC ..... C07D 487/04; A61K 31/519; A61P 31/00; A61P 31/04; A61P 35/00; A61P 35/04
See application file for complete search history.

(56) References Cited

U.S. PATENT DOCUMENTS

| | | | |
|---|---|---|---|
| 8,067,424 B2 | 11/2011 | Jogalekar | |
| 9,932,344 B2 | 4/2018 | Bondke | |
| 10,414,772 B2 | 9/2019 | Bondke | |
| 2010/0261683 A1 | 10/2010 | Jogalekar | |
| 2016/0362410 A1 | 8/2016 | Bondke | |
| 2018/0273540 A1 | 9/2018 | Bondke et al. | |
| 2020/0055862 A1 | 2/2020 | Bondke | |

FOREIGN PATENT DOCUMENTS

| | | |
|---|---|---|
| WO | WO 2001/047897 A1 | 7/2001 |
| WO | WO 2004/022561 A1 | 3/2004 |
| WO | WO 2004/069162 A2 | 8/2004 |
| WO | WO 2004/076458 A1 | 9/2004 |
| WO | WO 2004/087707 A1 | 10/2004 |
| WO | WO 2005/000838 A1 | 1/2005 |
| WO | WO 2008/151304 A1 | 12/2008 |
| WO | WO 2011/068667 A1 | 6/2011 |
| WO | WO 2012/059932 A1 | 5/2012 |
| WO | WO 2013/128028 A1 | 9/2013 |

(Continued)

OTHER PUBLICATIONS

Alarcon et al., 2009, Cell, vol. 139, pp. 757-769, "Nuclear CDKs Drive Smad Transcriptional Activation and Turnover in BMP and TGF-b Pathways".

Ali et al., 1993, The EMBO Journal, vol. 12, No. 3, pp. 1153-1160, "Modulation of transcriptional activation by ligand dependent phosphorylation of the human oestrogen receptor A/B region".

Ali et al., 2002, Nat. Rev. Cancer, vol. 2, pp. 101-112, "Endocrine-Responsive Breast Cancer and Strategies for Combating Resistance".

Ali et al, 2011, Annu. Rev. Med., vol. 62, pp. 217-232, "Antiestrogens and Their Therapeutic Applications in Breast Cancer and Other Diseases".

(Continued)

*Primary Examiner* — Susanna Moore
(74) *Attorney, Agent, or Firm* — Adsero IP

(57) ABSTRACT

Certain pyrazolo[1,5-a]pyrimidine-5,7-diamine compounds that inhibit cycline dependent kinase (CDK) (e.g., CDK1, CDK2, CDK4, CDK5, CDK6, CDK7, CDK8, CDK9, CDK10, CDK11, CDK12, CDK13, etc.) are disclosed. Pharmaceutical compositions comprising these compounds, and the use of these compounds and compositions to inhibit CDK; to treat disorders associated with CDK such as those arising from an inappropriate activity, mutation, overexpression, or upstream pathway activation of CDK; or disorders that are ameliorated by the inhibition of CDK; proliferative disorders; cancer; viral infections; neurodegenerative disorders; ischaemia; renal diseases; and cardiovascular disorders are also disclosed. Optionally, the treatment further comprises simultaneous or sequential treatment with a further active agent, e.g., an aromatase inhibitor, an anti-estrogen, a Her2 blocker, a cytotoxic chemotherapeutic agent, etc.

26 Claims, 4 Drawing Sheets

(56) References Cited

FOREIGN PATENT DOCUMENTS

WO    WO 2013/128029 A1    9/2013

OTHER PUBLICATIONS

Bartkowiak et al., 2010, Gene Dev., vol. 24, pp. 2303-2316, "CDK12 is a transcription elongation associated CTD kinase, the metazoan ortholog of yeast Ctk1".
Bastien et al., 2000, J. Biol. Chem., vol. 275, No. 29, pp. 21896-21904, "TFIIH Interacts with the Retinoic Acid Receptor γ and Phosphorylates Its AF-1-activating Domain through cdk7*".
Blazek et al., 2011, Gene Dev., vol. 25, pp. 2158-2172, "The Cyclin K/Cdk12 complex maintains genomic stability via regulation of expression of DNA damage response genes".
Borg et al., 2000, JNCI, vol. 92, No. 15, pp. 1260-1266, "High Frequency of Multiple Melanomas and Breast and Pancreas Carcinomas in CDKN2A Mutation-Positive Melanoma Families".
Chen et al., 2000, Molecular Cell, vol. 6, pp. 127-137, "Activation of Estrogen Receptor α by S118 Phosphorylation Involves a Ligand-Dependent Interaction with TFIIH and Participation of CDK7".
Chen et al., 2002, Oncogene, vol. 21, pp. 4921-4931, "Phosphorylation of human estrogen receptor α at serine 118 by two distinct signal transduction pathways revealed by phosphorylation-specific antisera".
Cheng et al., 2012, Mol. Cell. Biol., vol. 32, No. 22, pp. 4691-4704. "Interaction of Cyclin-Dependent Kinase 12/CrkRS with Cyclin K1 Is Required for the Phosphorylation of the C-Terminal Domain of RNA Polymerase II".
Chymkowitch et al., 2011, EMBO J., vol. 30, No. 3, pp. 468-479, "The phosphorylation of the androgen receptor by TFIIH directs the ubiquitin/proteasome process".
Claudio et al., 2006, J. Cell. Physiol., vol. 208, pp. 602-612, "Cdk9 Phosphorylates p53 on Serine 392 Independently of CKII".
Corlu et al., 2012, Int. J. Hepatol., Article ID 689324, 17 pages, "Regulation of the G1/S Transition in Hepatocytes: Involvement of the Cyclin-Dependent Kinase Cdk1 in the DNA Replication".
Cuzick et al., 2010, Lancet Oncol., vol. 11, pp. 1135-1141, "Effect of anastrozole and tamoxifen as adjuvant treatment for early-stage breast cancer: 10-year analysis of the ATAC Trial".
Drogat et al., 2012, Cell Rep., vol. 2, pp. 1068-1076, "Cdk11-CyclinL Controls the Assembly of the RNA Polymerase II Mediator Complex".
Dhariwala et al, 2008, Cell. Mol. Neurobiol., vol. 28, pp. 351-369, "An Unusual Member of the Cdk Family: Cdk5".
Fisher et al., 1994, Cell, vol. 78, pp. 713-724, "A Novel Cyclin Associates with MO15/CDK7 to Form the CDK-Activating Kinase".
GB Search Report for GB 1403093.6 dated Sep. 12, 2014.
Ganuza et al., 2012, EMBO J., vol. 31, pp. 2498-2510, "Genetic inactivation of Cdk7 leads to cell cycle arrest and induces premature aging due to adult stem cell exhaustion".
Gijsen et al., 2008, Tetrahedron, vol. 64, pp. 2456-2464, "Development of two diastereoselective routes towards trans-4-aminomethyl-piperidin-3-ol building blocks".
Gordon et al., 2010, Mol. Endocrinol., vol. 24, No. 12, pp. 2267-2280, "CDK9 Regulates AR Promoter Selectivity and Cell Growth through Serine 81 Phosphorylation".
Hamada et al., 1996, Biochim. Biophys. Acta., vol. 1310, pp. 149-156, "Protein kinase C inhibits the CAK-CDK2 cyclin-dependent kinase cascade and G1/S cell cycle progression in human diploid fibroblasts".
Hansson, 2008, Surg. Clin. North Am., vol. 88, pp. 897-916, "Familial Melanoma".
Hansson, 2010, Adv. Exp. Med. Biol., vol. 685, Chapter 13, pp. 134-145, "Familial Cutaneous Melanoma".
Hong et al., 1997, Tetrahedron Lett., vol. 38, No. 32, pp. 5607-5610, "Palladium Catalyzed Amination of 2-Chloro-I,3-Azole Derivatives: Mild Entry to Potent $H_2$- Antihistaminic Norastemizole".

Iorns et al., 2008, Cancer Cell, vol. 13, pp. 91-104, "Identification of CDK10 as an Important Determinant of Resistance to Endocrine Therapy for Breast Cancer".
International Search Report and Written Opinion of the International Searching Authority for PCT/GB2015/050494 dated Apr. 14, 2015.
International Preliminary Report on Patentability for PCT/GB2015/050494 dated Aug. 23, 2016.
Johnston et al., 2003, Nat. Rev. Cancer, vol. 3, pp. 821-831, "Aromatase Inhibitors For Breast Cancer: Lessons From The Laboratory".
Jones et al., 2007, Cell, vol. 128, pp. 683-692, "The Epigenomics of Cancer".
Knockaert et al., 2002, Trends Pharmacol. Sci., vol. 23, No. 9, pp. 417-425, "Pharmacological inhibitors of cyclin-dependent kinases".
Ko et al., 1997, Mol. Cell. Biol., vol. 17, No. 12, pp. 7220-7229 "p53 Is Phosphorylated by CDK7-Cyclin H in a $p36^{MAT1}$-Dependent Manner".
Kolb et al., 1994, Chem. Rev., vol. 94, pp. 2483-2547, "Catalytic Asymmetric Dihydroxylation".
Kosugi et al., 2012, J. Med. Chem., 55(15):6700-6715, "Mitogen-Activated Protein Kinase-Activated Protein Kinase 2 (MAPKAP-K2) as an Antiinflammatory Target: Discovery and In Vivo Activity of Selective Pyrazolo[1,5-α]pyrimidine Inhibitors Using a Focused Library and Structure-Based Optimization Approach".
Larochelle et al., 2007, Mol. Cell, vol. 25, pp. 839-850, "Requirements for Cdk7 in the Assembly of Cdk1/Cyclin B and Activation of Cdk2 Revealed by Chemical Genetics in Human Cells".
Larochelle et al., 2012, Nat. Struct. Mol. Biol., vol. 19, No. 11, pp. 1108-1115, "Cyclin-dependent kinase control of the initiation-to-elongation switch of RNA polymerase II".
Lu et al., 1992, Nature, pp. 358, pp. 641-645, "Human general transcription factor IIH phosphorylates the C-terminal domain of RNA polymerase II".
Lu et al., 1997, Mol. Cell. Biol., vol. 17, No. 10, pp. 5923-5934, "The CDK7-cycH-p36 Complex of Transcription Factor IIH Phosphorylates p53, Enhancing Its Sequence-Specific DNA Binding Activity In Vitro".
Malumbres et al., 2001, Nat. Rev. Cancer, vol. 1, pp. 222-231, "To Cycle or Not to Cycle: A Critical Decision in Cancer".
Malumbres et al., 2009, Nat. Cell Biology, vol. 11, pp. 1275-1276, "Cyclin-dependent kinases: a family portrait".
Malumbres et al., 2009, Nat. Rev. Cancer, vol. 9, pp. 153-166, "Cell cycle, CDKs and cancer: a changing paradigm".
Marshall et al., 2006, Nephron. Exp. Nephrol., vol. 102, No. 2, pp. e39-e48, "Cell Cycle and Glomerular Disease: A Minireview".
Monaco et al., 2005, Front. Biosci., vol. 10, No. 1, pp. 143-159, "Role of Protein Kinases In Neurodegenerative Disease: Cyclin-Dependent Kinases in Alzheimer's Disease".
Morgan, 1995, Nature, vol. 374, pp. 131-134, "Principles of CDK regulation".
Nagel et al., 1984, Angew. Chem. Int. Ed. Eng. 23, vol. 96, No. 6, pp. 435-436, "Asymmetric Hydrogenation of α-(Acetylamino)cinnamic Acid with a Novel Rhodium Complex; the Design of an Optimal Ligand**".
Ortega et al, 2002, Biochim. Biophys. Acta., vol. 1602, pp. 73-87, "Cyclin D-dependent kinases, INK4 inhibitors and cancer".
Osborne et al., 2011, Annu. Rev. Med., vol. 62, pp. 233-247, "Mechanisms of Endocrine Resistance in Breast Cancer".
Osborne, 1998, N. Engl. J. Med., vol. 339, No. 22, pp. 1609-1618, "Tamoxifen in the Treatment of Breast Cancer".
Peterson et al., 1991, J. Med. Chem., vol. 34, pp. 2787-2797, "Synthesis and Biological Evaluation of 4-Purinylpyrrolidine Nucleosides".
Pines, 1995, Biochem. J., vol. 308, pp. 697-711, "Cyclins and cyclin-dependent kinases: a biochemical view".
Radhakrishnan et al., 2006, Cell Cycle, vol. 5, No. 5, pp. 519-521, "CDK9 Phosphorylates p53 on Serine Residues 33, 315 and 392".
Remuzon, 1996, Tetrahedron, vol. 52, No. 44, 13803-13835, "Trans-4-Hydroxy.L-Proline, a Useful and Versatile Chiral Starting Block".
Rochette-Egly et al., 1997, Cell, vol. 90, pp. 97-107. "Stimulation of RARα Activation Function AF-1 through Binding to the General Transcription Factor TFIIH and Phosphorylation by CDK7".

(56) References Cited

OTHER PUBLICATIONS

Serizawa et al., 1995, Nature, vol. 374, pp. 280-282, "Association of Cdk-activating kinase subunits with transcription factor TFIIH".
Sherr et al., 1995, Genes Dev., vol. 9, pp. 1149-1163, "Inhibitors of mammalian $G_1$ cyclin-dependent kinases".
Shiekhattar et al., 1995, Nature, vol. 374, pp. 283-287, "Cdk-activating kinase complex is a component of human transcription factor TFIIH".
Skehan et al., 1990, J. Natl. Cancer Inst., vol. 82, No. 13, pp. 1107-1112, "New Colorimetric Cytotoxicity Assay for Anticancer-Drug Screening".
Wang et al., 2008, Trends Pharmacol. Sci., vol. 29, No. 6, pp. 302-313, "Cyclin-dependent kinase 9: a key transcriptional regulator and potential drug target in oncology, virology and cardiology".
Xu et al., 2011, J. Genet. Genomics, vol. 38, pp. 439-452, "Dysregulation of CDK8 and Cyclin C in tumorigenesis".
Xu et al., 2011, Tetrahedron Lett., vol. 52, pp. 3266-3270, "An improved synthesis of 2-oxa-7-azaspiro[3,5]nonane and analogs as novel reagents in medicinal chemistry".
Yankulov et al., 1995, J. Biol. Chem., vol. 270, No. 41, pp. 23922-23925, "The Transcriptional Elongation Inhibitor 5,6-Dichloro-1-β-D-ribofuranosylbenzimidazole Inhibits Transcription Factor IIH-associated Protein Kinase*".
Yu et al., 2012, Oncol. Rep., vol. 27, pp. 1266-1276, "CDK10 functions as a tumor suppressor gene and regulates survivability of biliary tract cancer cells".
Zuo et al., 1996, Nat. Genet., vol. 12, pp. 97-99, "Germline mutations in the $p16^{INK4a}$ binding domain of CDK4 in familial melanoma".

PYRAZOLO[1,5-A]PYRIMIDINE-5,7-DIAMINE COMPOUNDS AS CDK INHIBITORS AND THEIR THERAPEUTIC USE

RELATED APPLICATION

This application is continuation of U.S. application Ser. No. 16/559,735, filed Sep. 4, 2019, which is a continuation of U.S. Pat. No. 10,414,772, issued on Sep. 17, 2019, which is a continuation of U.S. Pat. No. 9,932,344, issued on Apr. 3, 2018. U.S. Pat. No. 9,932,344 is a 35 U.S.C. § 371 national phase application of International Application Serial No. PCT/GB2015/050494 (WO 2015/124941), filed Feb. 20, 2015. International Application Serial No. PCT/GB2015/050494 claims priority to United Kingdom patent application number 1403093.6, filed Feb. 21, 2014. Each of the referenced applications is incorporated herein by reference in its entirety.

TECHNICAL FIELD

The present invention pertains generally to the field of therapeutic compounds. More specifically the present invention pertains to certain pyrazolo[1,5-a]pyrimidine-5,7-diamine compounds (referred to herein as "PPDA compounds") that, inter alia, inhibit (e.g., selectively inhibit) CDK (e.g., CDK1, CDK2, CDK4, CDK5, CDK6, CDK7, CDK8, CDK9, CDK10, CDK11, CDK12, CDK13, etc.). The present invention also pertains to pharmaceutical compositions comprising such compounds, and the use of such compounds and compositions, both in vitro and in vivo, to inhibit CDK; and to treat disorders including: disorders that are associated with CDK; disorders that result from an inappropriate activity of a cyclin-dependent kinase (CDK); disorders that are associated with CDK mutation; disorders that are associated with CDK overexpression; disorders that are associated with upstream pathway activation of CDK; disorders that are ameliorated by the inhibition of CDK; proliferative disorders; cancer; viral infections (including HIV); neurodegenerative disorders (including Alzheimer's disease and Parkinson's disease); ischaemia; renal diseases; and cardiovascular disorders (including atherosclerosis). Optionally, the treatment further comprises treatment (e.g., simultaneous or sequential treatment) with a further active agent which is, e.g., an aromatase inhibitor, an anti-estrogen, a Her2 blocker, a cytotoxic chemotherapeutic agent, etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Cyclin-Dependent Protein Kinase (CDK)

Cyclin-dependent protein kinases (CDK) are the catalytic subunits of a family of 21 serine/threonine protein kinases (see, e.g., Malumbres et al., 2009), some of which control progression of the cell through the stages of growth, DNA replication and mitosis (see, e.g., Pines, 1995; Morgan, 1995). Activation of specific CDKs is required for appropriate progression through the different stages of the cell cycle and entry into the next stage of the cell cycle. CDK4 and CDK6 are required for progression through the growth (G1) phase, CDK2 in the DNA synthesis (S phase) and CDK1 for mitosis and cell division (M phase). Regulation of the activity of the cell cycle CDKs is pivotal for correct timing of progression of the cell through the stages of the cell cycle and their activities are regulated at many levels, including complex formation with specific cyclins (A, B, D and E class cyclins; these cyclins are synthesized and degraded through the stages of the cell cycle), CDK inhibitors (CDKI), in particular CIP/KIP and INK-type CDKIs (see, e.g., Sherr et al., 1995), as well as phosphorylation and dephosphorylation at specific residues. The phosphorylation status of a specific threonine residue in the activation loop, the so-called T-loop, is a key modification for the activity of cell cycle CDKs (see, e.g., Fisher et al., 1994).

De-regulation of CDK activity is an important component of many disease states, generally through elevated and/or inappropriate activation, as CDKs themselves are infrequently mutated. Rare examples of mutations in cell cycle CDKs include CDK4 families with hereditary melanoma that result in insensitivity to the INK4 CDKIs (see, e.g., Zuo et al, 1996). Inactivating mutations in the CDKN2A gene, which encodes for p16INK4 and p14ARF CDKIs, are more common in hereditary melanoma (see, e.g., Hansson, 2010), these mutations also being associated with greater incidence of breast and pancreatic cancer in affected families (see, e.g., Borg et al., 2000). CDK4 and CDK6 can be amplified and/or overexpressed in cancer, their cyclin effectors, D-type cyclins, are also often amplified and/or over-expressed, whilst the CDK4/CDK6 inhibitors (INK4 genes) are frequently deleted in many cancer types and/or undergo epigenetic silencing (see, e.g., Ortega et al., 2002). E-type cyclins interact with CDK2 for its activity and are frequently over-expressed in cancer, whilst the p21 and p27 inhibitory proteins that act on CDK2, as well as CDK1, are epigenetically silenced in cancer (see, e.g., Malumbres et al., 2001; Jones et al., 2007). Up-regulation of the activities of cell cycle CDKs is therefore integral to cancer development and progression.

CDK7, another member of the CDK family, which complexes with cyclin H and MAT1, phosphorylates the cell cycle CDKs in the activation of T-loop, to promote their activities (see, e.g., Fisher et al., 1994). As such, it has been proposed that inhibiting CDK7 would provide a potent means of inhibiting cell cycle progression, which may be especially relevant given that there is compelling evidence from gene knockout studies in mice for lack of an absolute requirement for CDK2, CDK4 and CDK6 for the cell cycle, at least in most cell types (see, e.g., Malumbres et al., 2009), whilst different tumors appear to require some, but be independent of other interphase CDKs (CDK2, CDK4, CDK6). Recent genetic and biochemical studies have confirmed the importance of CDK7 for cell cycle progression (see, e.g., Larochelle et al., 2007; Ganuza et al., 2012).

In addition to its role as the CDK Activating Kinase (CAK), CDK7/cyclin H/MAT1, in complex with the basal transcription factor TFIIH, phosphorylates RNA polymerase II (P0111) in its C-terminal domain (CTD) (see, e.g., Lu et al., 1995; Serizawa et al., 1995). CDK9, another member of the family, is also required for PolII CTD phosphorylation. The PolII CTD is comprised of a seven amino acid repeat having the sequence Tyrosine-Serine-Proline-Threonine-Serine-Proline-Serine (YSPTSPS), 52 YSPTSPS heptad repeats being present in the mammalian PolII CTD. Phosphorylation of serine-2 (S2) and serine-5 (S5) by CDK7 and CDK9 is required for release of PolII from the gene promoter at initiation of transcription. CDK7 appears to act upstream of CDK9, phosphorylation of S5 phosphorylation by CDK7 preceding S2 phosphorylation by CDK9 (see, e.g., Larochelle et al., 2012). Transcriptional inhibitors such as flavopiridol, as well as CDK inhibitors that inhibit CDK7 and CDK9 demonstrate the potential utility of CDK7 and CDK9 inhibition in cancer (see, e.g., Wang et al., 2008). In addition to their action in phosphorylating the PolII CTD, CDK7 and CDK9 have been implicated in regulating the activities of a number of transcription factors, including the breast cancer associated estrogen receptor (ER) (see, e.g., Chen et al., 2000), retinoid receptors (see, e.g., Rochette-Egly et al., 1997; Bastien et al., 2000), the androgen receptor (see, e.g., Chymkowitch et al., 2011; Gordon et al., 2010), as well as the tumor suppressor p53 (Lu et al., 1997; Ko et al., 1997; Radhakrishnan et al., 2006; Claudio et al., 2006). CDK8, a component of the mediator complex that regulates gene transcription, through a mechanism involving interaction between transcription factors and the PolII basal transcription machinery, also phosphorylates transcription factors to regulate their activities (see, e.g., Alarcon et al., 2009). CDK8 also appears to be important for regulating transcription reinitiation. The importance of CDK8 in cancer is highlighted by the finding that the CDK8 gene is amplified in 40-60% of colorectal cancers, whilst its cyclin partner, cyclin c, is upregulated in many cancer types, whilst functional studies are supportive of an oncogenic role for CDK8 in cancer (see, e.g., Xu et al., 2011). A potential role for CDK11 in regulating mediator activity has been described, indicating a role for CDK11 in transcription regulation (see, e.g., Drogat et al., 2012), whilst their ability to phosphorylate S2 the PolII CTD also implicates CDK12 and CDK13 in transcription; CDK12 is also implicated in maintenance of genome stability (see, e.g., Bartkowiak et al., 2010; Blazek et al., 2011; Cheng et al., 2012).

In addition to the great deal of evidence implicating the above and other CDKs (e.g., CDK10; see, e.g., Lorns et al., 2008; Yu et al., 2012) in cancer, CDKs are also important in viral infections including HIV (see, e.g., Knockeart et al., 2002), neurodegenerative disorders including Alzheimer's and Parkinson's disease (of particular note here is CDK5, see, e.g., Monaco et al., 2005; Faterna et al., 2008), ischae-mia, and proliferative disorders, including renal diseases (see, e.g., Marshall et al., 2006) and cardiovascular disorders including atherosclerosis.

The development of small molecule CDK inhibitors provides a potentially powerful approach in the treatment of many human diseases, in particular cancer. Thus inhibition of cell cycle progression may be achieved through the development of selective CDK1 inhibitors (as CDK1 appears to be indispensible for the cell cycle) or selective CDK7 inhibitors (as CDK7 regulates the cell cycle CDKs) or with inhibitors with activity against all of the cell cycle CDKs. Some evidence indicates that selective CDK4/CDK6 or CDK2 inhibitors may have utility for specific conditions (e.g., CDK4/CDK6 in haematological malignancies and CDK2 in glioblastomas or osteosarcomas), and so development of selective inhibitors for these CDKs may be of utility, the selectivity perhaps aiding toxicity issues.

Known Compounds

It appears that the following compounds are known.

| CAS Registry No. | Structure |
|---|---|
| 771502-87-5 | 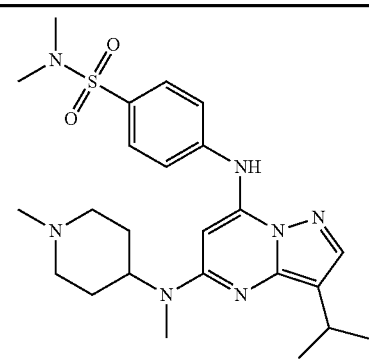 |
| 771501-59-8 | 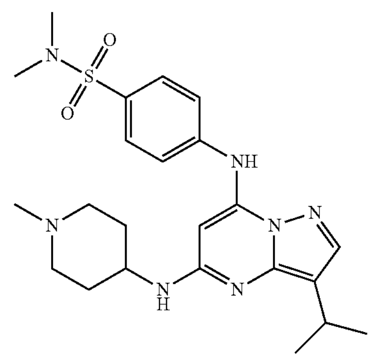 [SMILES: CC(C)c1cnn2c(Nc3ccc(S(=O)(=O)N(C)C)cc3)cc(NC3CCN(C)CC3)nc12] |
| 771509-61-6 | 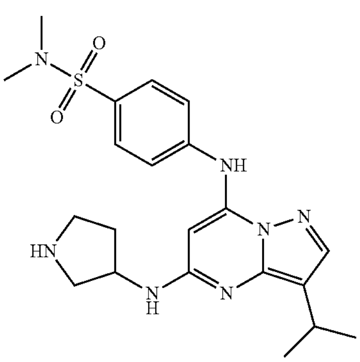 [SMILES: CC(C)c1cnn2c(Nc3ccc(S(=O)(=O)N(C)C)cc3)cc(NC3CCNC3)nc12] |

| CAS Registry No. | Structure |
|---|---|
| 771502-45-5 | 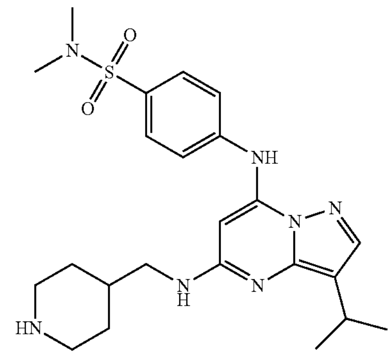 [SMILES: CC(C)c1cnn2c(Nc3ccc(S(=O)(=O)N(C)C)cc3)cc(NCC3CCNCC3)nc12] |
| 771508-20-4 | 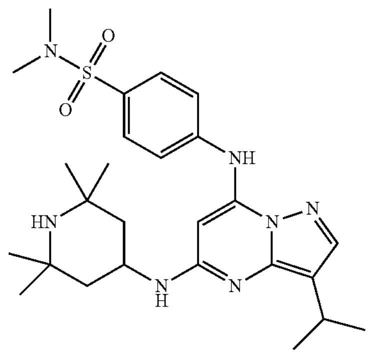 [SMILES: CC(C)c1cnn2c(Nc3ccc(S(=O)(=O)N(C)C)cc3)cc(NC3CC(C)(C)NC(C)(C)C3)nc12] |
| 1092443-65-6 | 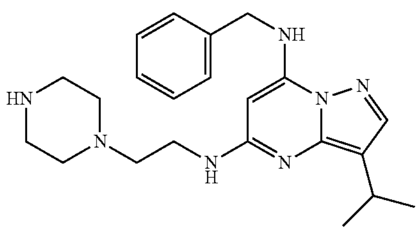 [SMILES: CC(C)c1cnn2c(NCc3ccccc3)cc(NCCN3CCNCC3)nc12] |
| 1092443-63-4 | 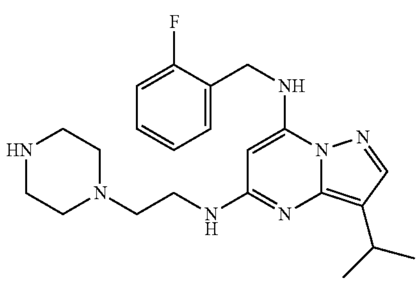 [SMILES: CC(C)c1cnn2c(NCc3ccccc3F)cc(NCCN3CCNCC3)nc12] |
| 1092444-59-1 | 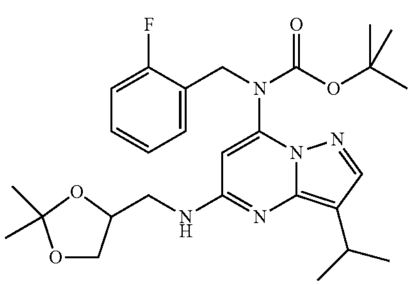 [SMILES: CC(C)c1cnn2c(N(Cc3ccccc3F)C(=O)OC(C)(C)C)cc(NCC3COC(C)(C)O3)nc12] |

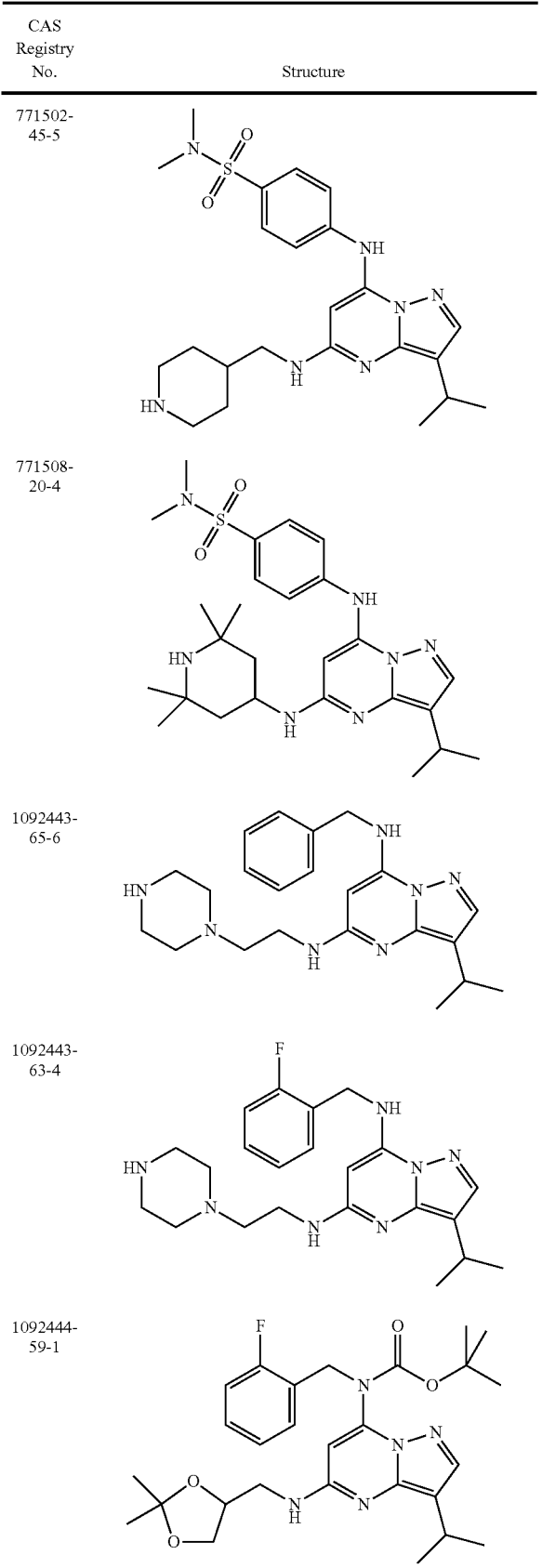

| CAS Registry No. | Structure |
|---|---|
| 1092444-58-0 | 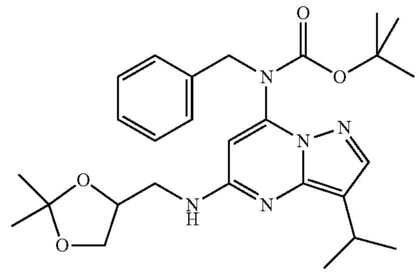 [SMILES: CC(C)c1cnn2c(N(Cc3ccccc3)C(=O)OC(C)(C)C)cc(NCC3COC(C)(C)O3)nc12] |
| 1092444-23-9 | 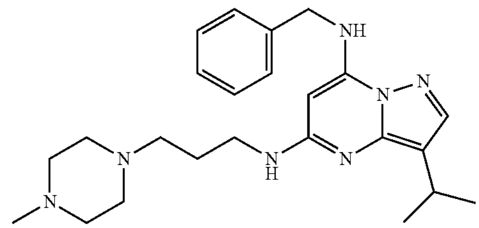 [SMILES: CC(C)c1cnn2c(NCc3ccccc3)cc(NCCCN3CCN(C)CC3)nc12] |
| 1092444-03-5 | 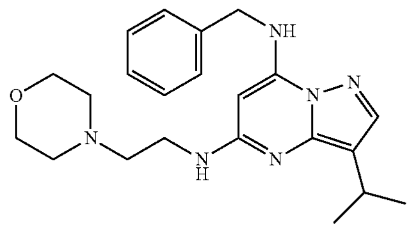 [SMILES: CC(C)c1cnn2c(NCc3ccccc3)cc(NCCN3CCOCC3)nc12] |
| 1256288-39-7 | 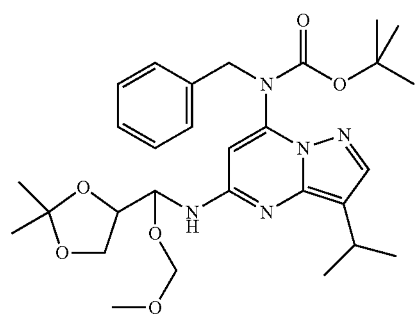 [SMILES: COCOC(Nc1cc(N(Cc2ccccc2)C(=O)OC(C)(C)C)n2ncc(C(C)C)c2n1)C1COC(C)(C)O1] |

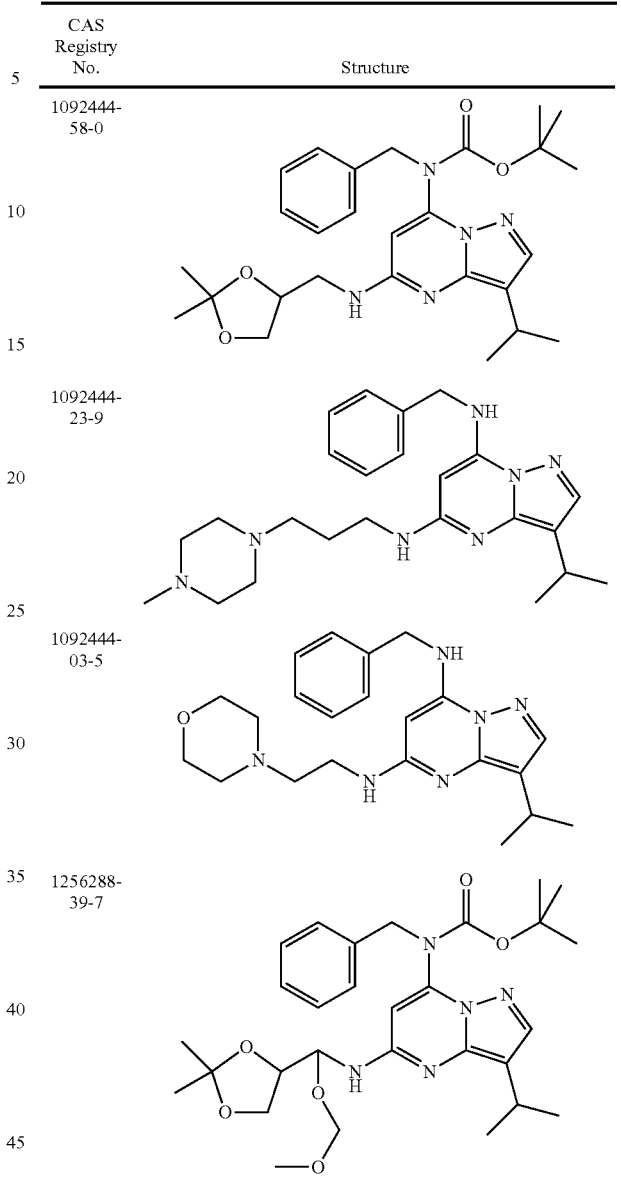

SUMMARY OF THE INVENTION

Figure 1:
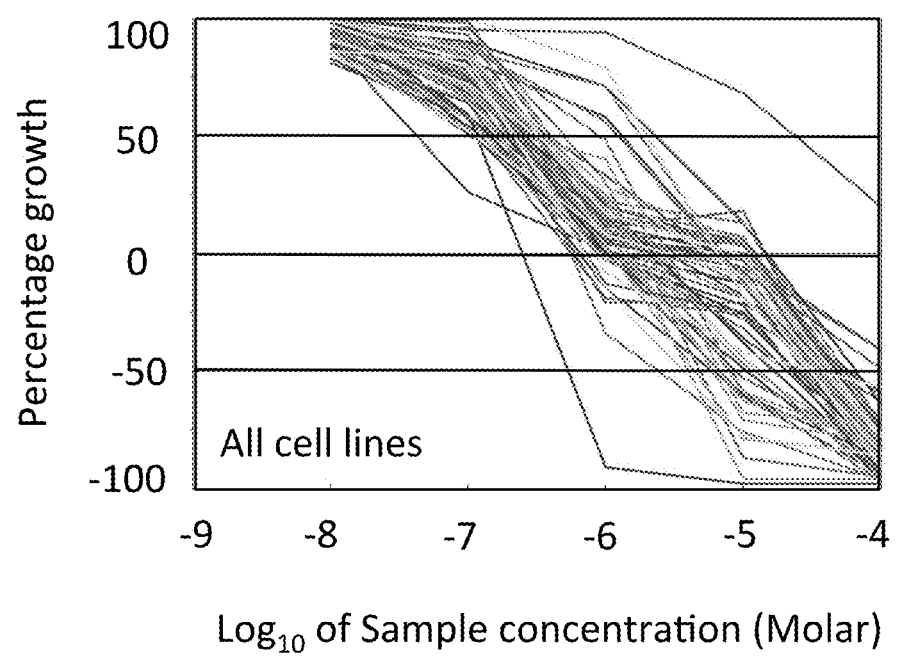
FIG. 1 is a graph of percentage growth inhibition as a function of the base-10 logarithm of the molar concentration of the test compound, PPDA-001, as determined by the NCI60 cancer cell line screen. Each line represents one cell line.

One aspect of the invention pertains to certain pyrazolo[1,5-a]pyrimidine-5,7-diamine compounds (referred to herein as "PPDA compounds"), as described herein.

Another aspect of the invention pertains to a composition (e.g., a pharmaceutical composition) comprising a PPDA compound, as described herein, and a pharmaceutically acceptable carrier or diluent.

Another aspect of the invention pertains to a method of preparing a composition (e.g., a pharmaceutical composition) comprising the step of mixing a PPDA compound, as described herein, and a pharmaceutically acceptable carrier or diluent.

Another aspect of the present invention pertains to a method of inhibiting CDK (e.g., CDK1, CDK2, CDK4, CDK5, CDK6, CDK7, CDK8, CDK9, CDK10, CDK11, CDK12, CDK13, etc.) function (e.g., in a cell), in vitro or in vivo, comprising contacting the cell with an effective amount of a PPDA compound, as described herein.

Another aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a PPDA compound, as described herein.

Another aspect of the present invention pertains to a PPDA compound as described herein for use in a method of treatment of the human or animal body by therapy, for example, for use a method of treatment of a disorder (e.g., a disease) as described herein.

Another aspect of the present invention pertains to use of a PPDA compound, as described herein, in the manufacture of a medicament, for example, for use in a method of treatment, for example, for use a method of treatment of a disorder (e.g., a disease) as described herein.

Another aspect of the present invention pertains to a method of treatment, for example, a method of treatment of a disorder (e.g., a disease) as described herein, comprising administering to a subject in need of treatment a therapeutically-effective amount of a PPDA compound, as described herein, preferably in the form of a pharmaceutical composition.

In one embodiment, the treatment further comprises treatment (e.g., simultaneous or sequential treatment) with a further active agent which is, e.g., an aromatase inhibitor, an anti-estrogen, a Her2 blocker, a cytotoxic chemotherapeutic agent, etc., as described herein.

Another aspect of the present invention pertains to a kit comprising (a) a PPDA compound, as described herein, preferably provided as a pharmaceutical composition and in a suitable container and/or with suitable packaging; and (b) instructions for use, for example, written instructions on how to administer the compound.

Another aspect of the present invention pertains to a PPDA compound obtainable by a method of synthesis as described herein, or a method comprising a method of synthesis as described herein.

Another aspect of the present invention pertains to a PPDA compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain compounds which are related to pyrazolo[1,5-a]pyrimidine-5,7-diamine:

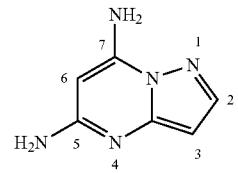

All of the compounds of the present invention have:

(a) a substituted amino group at the 5-position (denoted herein as —$NR^{5X}R^{5Y}$);

(b) a substituted amino group at the 7-position (denoted herein as —$NHR^7$); and (c) an alkyl or cycloalkyl group at the 3-position (denoted herein as —$R^3$).

More specifically, the group —$R^{5X}$ is, or contains, a non-aromatic heterocyclic ring having from 5 to 7 ring atoms, including at least one nitrogen ring atom (denoted herein as -Q), and substituted with at least one "oxy" substituent (denoted herein as -J).

Thus, one aspect of the present invention is a compound of the following formula, or a pharmaceutically acceptable salt, hydrate, or solvate thereof, wherein —$R^2$, —$R^3$, —$R^{5X}$, —$R^{5Y}$, —$R^6$, and —$R^7$ are as defined herein (for convenience, collectively referred to herein as "pyrazolo[1,5-a]pyrimidine-5,7-diamine compounds" and "PPDA compounds"):

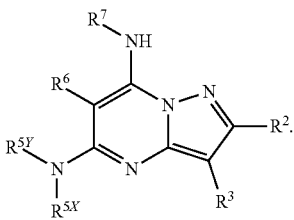

Some embodiments of the invention include the following:

(1) A compound of the following formula:

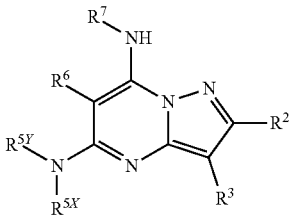

or a pharmaceutically acceptable salt or solvate thereof;
wherein:
—$R^{5X}$ is -$L^{5X}$-Q;
-$L^{5X}$- is independently a covalent single bond or -$L^{5XA}$-;
-$L^{5XA}$- is independently linear or branched saturated $C_{1-6}$ alkylene, and is optionally substituted with one or more groups selected from —OH and —$OR^{L5X}$, wherein each —$R^{L5X}$ is independently linear or branched saturated $C_{1-6}$ alkyl or saturated $C_{3-6}$cycloalkyl;
-Q is a non-aromatic heterocyclic ring having from 5 to 7 ring atoms, including at least one nitrogen ring atom, and is substituted with "n" groups -J, and is substituted with "m" groups —$R^Q$;
"n" is 1, 2, or 3;
"m" is 0, 1, 2, or 3;
each -J is independently —OH, —$OR^J$, -$L^J$-OH, or -$L^J$-$OR^J$;
each —$R^J$ is independently linear or branched saturated $C_{1-6}$ alkyl or saturated $C_{3-6}$cycloalkyl;
each -$L^J$- is independently linear or branched saturated $C_{1-6}$alkylene;
each —$R^Q$ is independently —F, —Cl, —Br, —I, —$R^{QA}$, —$CF_3$, —$OCF_3$, —$NH_2$, —$NHR^{QA}$, —$NR^{QA}_2$, pyrrolidino, piperidino, morpholino, piperazino, N—($R^{QA}$)-piperazino, —SH, —$SR^{QA}$, or —CN;
each —$R^{QA}$ is independently linear or branched saturated $C_{1-6}$ alkyl or saturated $C_{3-6}$cycloalkyl;
—$R^{5Y}$ is independently —H or —$R^{5YA}$;
—$R^{5YA}$ is independently linear or branched saturated $C_{1-6}$ alkyl;
—$R^7$ is independently —$R^{7X}$ or —C(=O)$R^{7X}$;
each —$R^{7X}$ is independently:
—$R^{7A}$, —$R^{7E}$, —$R^{7D}$—$R^{7D}$, —$R^{7E}$,
-$L^7$-$R^{7B}$, -$L^7$-$R^{7C}$, -$L^7$-$R^{7D}$, or -$L^7$-$R^{7E}$;
each -$L^7$- is independently linear or branched saturated $C_{1-6}$alkylene;
each —$R^{7A}$ is independently linear or branched saturated $C_{1-6}$alkyl, and is optionally substituted with one or more substituents —$W^1$;
each —$R^{7B}$ is saturated $C_{3-6}$cycloalkyl, and is optionally substituted with one or more substituents —$W^2$;

each —$R^{7D}$ is non-aromatic $C_{3-7}$ heterocyclyl, and is optionally substituted with one or more substituents —$W^2$;
each —$R^{7D}$ is independently phenyl or naphthyl, and is optionally substituted with one or more substituents —$W^3$;
each —$R^{7E}$ is $C_{5-12}$ heteroaryl, and is optionally substituted with one or more substituents —$W^3$;
each —$W^1$ is independently:
F, —Cl, —Br, —I, —$CF_3$, —OH, —$OR^{W1}$, —$OCF_3$, —$NH_2$, —$NHR^{W1}$, —$NR^{W1}_2$, pyrrolidino, piperidino, morpholino, piperazino, N—($R^{W1}$)-piperazino, —C(=O)OH, —C(=O)$OR^{W1}$, —C(=O)$NH_2$, —C(=O)$NHR^{W1}$, —C(=O)$NR^{W1}_2$, —C(=O)-pyrrolidino, —C(=O)-piperidino, —C(=O)-morpholino, —C(=O)-piperazino, —C(=O)—N—($R^{W1}$)-piperazino, —S(=O)$R^{W1}$, —S(=O)$_2R^{W1}$, —S(=O)$_2NH_2$, —S(=O)$_2NHR^{W1}$, —S(=O)$_2NR^{W1}_2$, —S(=O)$_2$ pyrrolidino, —S(=O)$_2$-piperidino, —S(=O)$_2$-morpholino, —S(=O)$_2$-piperazino, —S(=O)$_2$—N—($R^{W1}$)-piperazino, —CN, or —$NO_2$;
wherein each —$R^{W1}$ is independently linear or branched saturated $C_{1-6}$alkyl, phenyl, or —$CH_2$-phenyl, wherein each phenyl is optionally substituted with one or more groups selected from —F, —Cl, —Br, —I, —$R^{W11}$, —$CF_3$, —OH, —$OR^{W11}$, and —$OCF_3$, wherein each —$R^{W11}$ is independently linear or branched saturated $C_{1-6}$alkyl;
each —$W^2$ is independently:
—F, —Cl, —Br, —I, —$R^{W2}$, —$CF_3$, —OH, —OR', —$OCF_3$, —$NH_2$, —$NHR^{W2}$, —$NR^{W2}_2$, pyrrolidino, piperidino, morpholino, piperazino, N—($R^{W2}$)-piperazino, —C(=O)OH, —C(=O)$OR^{W2}$, —C(=O)$NH_2$, —C(=O)$NHR^{W2}$, —C(=O)$NR^{W2}_2$, —C(=O)-pyrrolidino, —C(=O)-piperidino, —C(=O)-morpholino, —C(=O)-piperazino, —C(=O)—N—($R^{W2}$)-piperazino, —S(=O)$R^{W2}$, —S(=O)$_2R^{W2}$, —S(=O)$_2NH_2$, —S(=O)$_2NHR^{W2}$, —S(=O)$_2NR^{W2}_2$, —S(=O)$_2$ pyrrolidino, —S(=O)$_2$-piperidino, —S(=O)$_2$-morpholino, —S(=O)$_2$-piperazino, —S(=O)$_2$—N—($R^{W2}$)-piperazino, —CN, or —$NO_2$;
wherein each —$R^{W2}$ is independently linear or branched saturated $C_{1-6}$alkyl, phenyl, or —$CH_2$-phenyl, wherein each phenyl is optionally substituted with one or more groups selected from —F, —Cl, —Br, —I, —$R^{W22}$, —$CF_3$, —OH, —$OR^{W22}$, and —$OCF_3$, wherein each —$R^{W22}$ is independently linear or branched saturated $C_{1-6}$alkyl;
each —$W^3$ is independently:
—F, —Cl, —Br, —I, —$R^{W3}$, —$CF_3$, —OH, —$OR^{W3}$, —$OCF_3$, —$NH_2$, —$NHR^{W3}$, —$NR^{W3}_2$, pyrrolidino, piperidino, morpholino, piperazino, N—($R^{W3}$)-piperazino, —C(=O)OH, —C(=O)$OR^{W3}$, —C(=O)$NH_2$, —C(=O)$NHR^{W3}$, —C(=O)$NR^{W3}_2$, —C(=O)-pyrrolidino, —C(=O)-piperidino, —C(=O)-morpholino, —C(=O)-piperazino, —C(=O)—N—($R^{W3}$)-piperazino, —S(=O)$R^{W3}$, —S(=O)$_2R^{W3}$, —S(=O)$_2NH_2$, —S(=O)$_2NHR^{W3}$, —S(=O)$_2NR^{W3}_2$, —S(=O)$_2$ pyrrolidino, —S(=O)$_2$-piperidino, —S(=O)$_2$-morpholino, —S(=O)$_2$-piperazino, —S(=O)$_2$—N—($R^{W3}$)-piperazino, —CN, or —$NO_2$;
wherein each —$R^{W3}$ is independently linear or branched saturated $C_{1-6}$alkyl, phenyl, or —$CH_2$-phenyl, wherein each phenyl is optionally substituted with one or more groups selected from —F, —Cl, —Br, —I, —$R^{W33}$, —CF$_3$, —OH, —OR$^{W33}$, and —OCF$_3$, wherein each —R$^{W33}$ is independently linear or branched saturated C$_{1-6}$alkyl;

—R$^3$ is independently —R$^{3A}$ or —R$^{3B}$;

—R$^{3A}$ is independently linear or branched saturated C$_{1-6}$alkyl;

—R$^{3B}$ is saturated C$_{3-7}$cycloalkyl;

—R$^2$ is independently —H or —R$^{2A}$; —R$^{2A}$ is independently —F, —Cl, —Br, —I, —R$^{2AA}$, —CF$_3$, —OH, —OR$^{2AA}$, —OCF$_3$, —NH$_2$, —NHR$^{2AA}$, —NR$^{2AA}$$_2$, pyrrolidino, piperidino, morpholino, piperazino, N—(R$^{2AA}$)-piperazino, —SH, —SR$^{2AA}$, or —CN;

each —R$^{2AA}$ is independently linear or branched saturated C$_{1-6}$alkyl;

—R$^6$ is independently —H or —R$^{6A}$; —R$^{6A}$ is independently —F, —Cl, —Br, —I, —R$^{6AA}$, —CF$_3$, —OH, —OR$^{6AA}$, —OCF$_3$, —NH$_2$, —NHR$^{6AA}$, —NR$^{6AA}$$_2$, pyrrolidino, piperidino, morpholino, piperazino, N—(R$^{6AA}$)-piperazino, —SH, —SR$^{6AA}$, or —CN; and each —R$^{6AA}$ is independently linear or branched saturated C$_{1-6}$alkyl.

For the avoidance of doubt:

The index "C$_{x-y}$" in terms such as "C$_{5-10}$ heteroaryl", "C$_{3-7}$ heterocyclyl", and the like, refers to the number of ring atoms, which may be carbon atoms or heteroatoms (e.g., N, O, S). For example, pyridyl is an example of a C$_6$ heteroaryl group, and piperidino is an example of a C$_6$ heterocyclyl group.

The term "heteroaryl" refers to a group that is attached to the rest of the molecule by an atom that is part of an aromatic ring, wherein the aromatic ring is part of an aromatic ring system, and the aromatic ring system has one or more heteroatoms (e.g., N, O, S). For example, pyridyl is an example of a C$_6$ heteroaryl group, and quinolyl is an example of a C$_{10}$ heteroaryl group.

The term "heterocyclyl" refers to a group that is attached to the rest of the molecule by a ring atom that is not part of an aromatic ring (i.e., the ring is partially or fully saturated), and the ring contains one or more heteroatoms (e.g., N, O, S). For example, piperidino is an example of a C$_6$ heterocyclyl group.

Unless otherwise indicated, where a compound is shown or described which has one or more chiral centres, and two or more stereoisomers are possible, all such stereoisomers are disclosed and encompassed, both individually (e.g., as isolated from the other stereoisomer(s)) and as mixtures (e.g., as equimolar or non-equimolar mixtures of two or more stereoisomers). For example, unless otherwise indicated, where a compound has one chiral centre, each of the (R) and (S) enantiomers are disclosed and encompassed, both individually (e.g., as isolated from the other enantiomer) and as a mixture (e.g., as equimolar or non-equimolar mixtures of the two enantiomers). For example, the initial carbon atom of a pendant sec-butyl group, —CH(CH$_3$)CH$_2$CH$_3$ is usually chiral, and so gives rise to stereoisomers, e.g., (R) and (S) enantiomers if it is the only chiral centre, each of which is disclosed and encompassed.

The Group -L$^{5X}$-

(2) A compound according to (1), wherein -L$^{5X}$- is a covalent single bond.

(3) A compound according to (1), wherein -L$^{5X}$- is -L$^{5XA}$-.

The Group -L$^{5XA}$-

(4) A compound according to any one of (1) to (3), wherein -L$^{5XA}$-, if present, is independently linear or branched saturated C$_{1-6}$alkylene.

(5) A compound according to any one of (1) to (3), wherein -L$^{5XA}$-, if present, is independently linear or branched saturated C$_{1-4}$ alkylene, and is optionally substituted with one or more groups selected from —OH and —OR$^{L5X}$, wherein each —R$^{L5X}$ is independently linear or branched saturated C$_{1-6}$alkyl or saturated C$_{3-6}$cycloalkyl.

(6) A compound according to any one of (1) to (3), wherein -L$^{5XA}$-, if present, is independently linear or branched saturated C$_{1-4}$ alkylene.

(7) A compound according to any one of (1) to (3), wherein -L$^{5XA}$-, if present, is independently —CH$_2$—, —CH(CH$_3$)—, —C(CH$_3$)$_2$—, —CH$_2$CH$_2$—, —CH(CH$_3$)CH$_2$—, —CH$_2$CH(CH$_3$)—, or —CH$_2$CH$_2$CH$_2$—.

(8) A compound according to any one of (1) to (3), wherein -L$^{5XA}$-, if present, is independently —CH$_2$—, —CH(CH$_3$)—, —C(CH$_3$)$_2$—, or —CH$_2$CH$_2$—.

(9) A compound according to any one of (1) to (3), wherein -L$^{5XA}$-, if present, is independently —CH$_2$—, —CH(CH$_3$)—, or —C(CH$_3$)$_2$—.

(10) A compound according to any one of (1) to (3), wherein -L$^{5XA}$-, if present, is independently —CH$_2$— or —CH$_2$CH$_2$—.

(11) A compound according to any one of (1) to (3), wherein -L$^{5XA}$-, if present, is —CH$_2$—.

The Group —R$^{L5X}$

(12) A compound according to any one of (1) to (11), wherein each —R$^{L5X}$, if present, is independently linear or branched saturated C$_{1-4}$ alkyl or saturated C$_{3-6}$cycloalkyl.

(13) A compound according to any one of (1) to (11), wherein each —R$^{L5X}$, if present, is independently linear or saturated C$_{1-4}$ alkyl.

(14) A compound according to any one of (1) to (11), wherein each —R$^{L5X}$, if present, is independently -Me, -Et, -nPr, -iPr, -nBu, -iBu, -sBu, or -tBu.

(15) A compound according to any one of (1) to (11), wherein each —R$^{L5X}$, if present, is independently -Me, -Et, -nPr, or -iPr.

(16) A compound according to any one of (1) to (11), wherein each —R$^{L5X}$, if present, is independently -Me or -Et.

(17) A compound according to any one of (1) to (11), wherein each —R$^{L5X}$, if present, is -Me.

The Group -Q

(18) A compound according to any one of (1) to (17), wherein -Q is a non-aromatic heterocyclic ring having from 5 to 7 ring atoms, including at least one nitrogen ring atom, wherein the point of attachment is via a ring carbon atom, and is substituted with "n" groups -J, and is substituted with "m" groups —R$^Q$.

(19) A compound according to any one of (1) to (17), wherein -Q is a non-aromatic heterocyclic ring having from 5 to 7 ring atoms, including at least one nitrogen ring atom, wherein the point of attachment is via a ring nitrogen atom, and is substituted with "n" groups -J, and is substituted with "m" groups —R$^Q$.

(20) A compound according to any one of (1) to (17), wherein -Q is pyrrolidinyl, piperidinyl, morpholinyl, piperazinyl, azepanyl, or diazepanyl, and is substituted with "n" groups -J, and is substituted with "m" groups —R$^Q$.

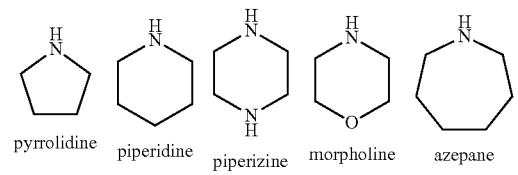

pyrrolidine   piperidine   piperizine   morpholine   azepane

[1,2]diazepane  [1,3]diazepane  [1,4]diazepane

(21) A compound according to any one of (1) to (17), wherein -Q is pyrrolidinyl, piperidinyl, morpholinyl, piperazinyl, azepanyl, or diazepanyl, wherein the point of attachment is via a ring carbon atom, and is substituted with "n" groups -J, and is substituted with "m" groups —$R^Q$.

(22) A compound according to any one of (1) to (17), wherein -Q is pyrrolidinyl, piperidinyl, morpholinyl, piperazinyl, azepanyl, or diazepanyl, wherein the point of attachment is via a ring nitrogen atom, and is substituted with "n" groups -J, and is substituted with "m" groups —$R^Q$.

(23) A compound according to any one of (1) to (17), wherein -Q is pyrrolidinyl, piperidinyl, morpholinyl, or piperazinyl, and is substituted with "n" groups -J, and is substituted with "m" groups —$R^Q$.

(24) A compound according to any one of (1) to (17), wherein -Q is pyrrolidinyl, piperidinyl, morpholinyl, or piperazinyl, wherein the point of attachment is via a ring carbon atom, and is substituted with "n" groups -J, and is substituted with "m" groups —$R^Q$.

(25) A compound according to any one of (1) to (17), wherein -Q is pyrrolidinyl, piperidinyl, morpholinyl, or piperazinyl, wherein the point of attachment is via a ring nitrogen atom, and is substituted with "n" groups -J, and is substituted with "m" groups —$R^Q$.

(26) A compound according to any one of (1) to (17), wherein -Q is pyrrolidinyl, and is substituted with "n" groups -J, and is substituted with "m" groups —$R^Q$.

(27) A compound according to any one of (1) to (17), wherein -Q is pyrrolidinyl, wherein the point of attachment is via a ring carbon atom, and is substituted with "n" groups -J, and is substituted with "m" groups —$R^Q$.

(28) A compound according to any one of (1) to (17), wherein -Q is pyrrolidinyl, wherein the point of attachment is via a ring nitrogen atom (i.e., pyrrolidino) and is substituted with "n" groups -J, and is substituted with "m" groups —$R^Q$.

(29) A compound according to any one of (1) to (17), wherein -Q is pyrrolidin-2-yl, and is substituted with "n" groups -J, and is substituted with "m" groups —$R^Q$.

(30) A compound according to any one of (1) to (17), wherein -Q is pyrrolidin-3-yl, and is substituted with "n" groups -J, and is substituted with "m" groups —$R^Q$.

(31) A compound according to any one of (1) to (17), wherein -Q is piperidinyl, and is substituted with "n" groups -J, and is substituted with "m" groups —$R^Q$.

(32) A compound according to any one of (1) to (17), wherein -Q is piperidinyl, wherein the point of attachment is via a ring carbon atom, and is substituted with "n" groups -J, and is substituted with "m" groups —$R^Q$.

(33) A compound according to any one of (1) to (17), wherein -Q is piperidin-4-yl, and is substituted with "n" groups -J, and is substituted with "m" groups —$R^Q$.

(34) A compound according to any one of (1) to (17), wherein -Q is piperidin-3-yl, and is substituted with "n" groups -J, and is substituted with "m" groups —$R^Q$.

(35) A compound according to any one of (1) to (17), wherein -Q is piperidin-2-yl, and is substituted with "n" groups -J, and is substituted with "m" groups —$R^Q$.

(36) A compound according to any one of (1) to (17), wherein -Q is piperidinyl, wherein the point of attachment is via a ring nitrogen atom (i.e., piperidino), and is substituted with "n" groups -J, and is substituted with "m" groups —$R^Q$.

(37) A compound according to any one of (1) to (17), wherein -Q is morpholinyl, and is substituted with "n" groups -J, and is substituted with "m" groups —$R^Q$.

(38) A compound according to any one of (1) to (17), wherein -Q is morpholinyl, wherein the point of attachment is via a ring carbon atom, and is substituted with "n" groups -J, and is substituted with "m" groups —$R^Q$.

(39) A compound according to any one of (1) to (17), wherein -Q is morpholin-2-yl, and is substituted with "n" groups -J, and is substituted with "m" groups —$R^Q$.

(40) A compound according to any one of (1) to (17), wherein -Q is morpholin-3-yl, and is substituted with "n" groups -J, and is substituted with "m" groups —$R^Q$.

(41) A compound according to any one of (1) to (17), wherein -Q is morpholinyl, wherein the point of attachment is via a ring nitrogen atom (i.e., morpholino), and is substituted with "n" groups -J, and is substituted with "m" groups —$R^Q$.

(42) A compound according to any one of (1) to (17), wherein -Q is piperazinyl, and is substituted with "n" groups -J, and is substituted with "m" groups —$R^Q$.

(43) A compound according to any one of (1) to (17), wherein -Q is piperazinyl, wherein the point of attachment is via a ring carbon atom, and is substituted with "n" groups -J, and is substituted with "m" groups —$R^Q$.

(44) A compound according to any one of (1) to (17), wherein -Q is piperazin-2-yl, and is substituted with "n" groups -J, and is substituted with "m" groups —$R^Q$.

(45) A compound according to any one of (1) to (17), wherein -Q is piperazin-3-yl, and is substituted with "n" groups -J, and is substituted with "m" groups —$R^Q$.

(46) A compound according to any one of (1) to (17), wherein -Q is piperazinyl, wherein the point of attachment is via a ring nitrogen atom (i.e., piperazino), and is substituted with "n" groups -J, and is substituted with "m" groups —$R^Q$.

The Index "n"

(47) A compound according to any one of (1) to (46), wherein "n" is 1 or 2.

(48) A compound according to any one of (1) to (46), wherein "n" is 1.

(49) A compound according to any one of (1) to (46), wherein "n" is 2.

(50) A compound according to any one of (1) to (46), wherein "n" is 3.

The Index "m"

(51) A compound according to any one of (1) to (50), wherein "m" is 0, 1 or 2.

(52) A compound according to any one of (1) to (50), wherein "m" is 0 or 1.

(53) A compound according to any one of (1) to (50), wherein "m" is 0.

(54) A compound according to any one of (1) to (50), wherein "m" is 1.

(55) A compound according to any one of (1) to (50), wherein "m" is 2.

(56) A compound according to any one of (1) to (50), wherein "m" is 3.

Some Preferred Groups -Q

(57) A compound according to any one of (1) to (56), wherein -Q is selected from:

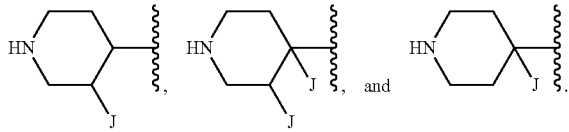

(58) A compound according to any one of (1) to (56), wherein -Q is:

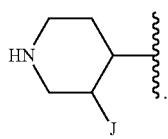

(59) A compound according to any one of (1) to (56), wherein -Q is:

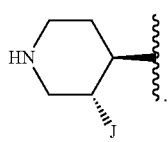

(60) A compound according to any one of (1) to (56), wherein -Q is:

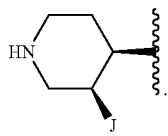

(61) A compound according to any one of (1) to (56), wherein -Q is:

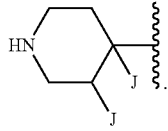

(62) A compound according to any one of (1) to (56), wherein -Q is:

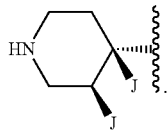

(63) A compound according to any one of (1) to (56), wherein -Q is:

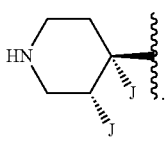

(64) A compound according to any one of (1) to (56), wherein -Q is:

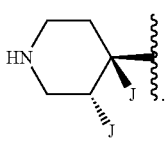

(65) A compound according to any one of (1) to (56), wherein -Q is:

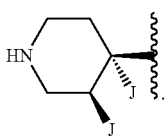

(66) A compound according to any one of (1) to (56), wherein -Q is:

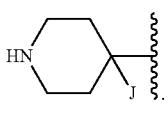

(67) A compound according to any one of (1) to (56), wherein -Q is selected from:

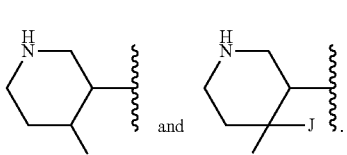

(68) A compound according to any one of (1) to (56), wherein -Q is:

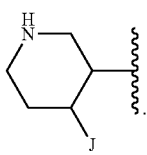

(69) A compound according to any one of (1) to (56), wherein -Q is:

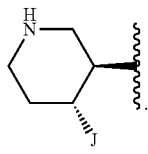

(70) A compound according to any one of (1) to (56), wherein -Q is:

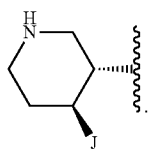

(71) A compound according to any one of (1) to (56), wherein -Q is:

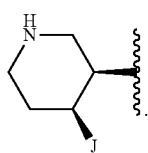

(72) A compound according to any one of (1) to (56), wherein -Q is:

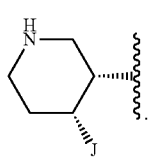

(73) A compound according to any one of (1) to (56), wherein -Q is:

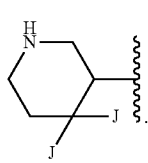

(74) A compound according to any one of (1) to (56), wherein -Q is:

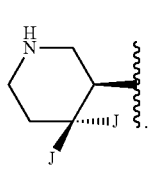

(75) A compound according to any one of (1) to (56), wherein -Q is:

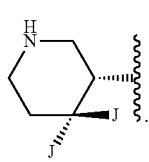

(76) A compound according to any one of (1) to (56), wherein -Q is selected from:

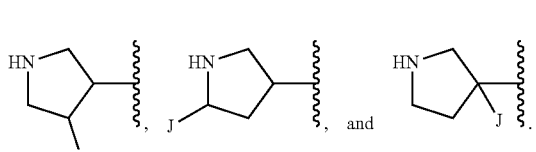

(77) A compound according to any one of (1) to (56), wherein -Q is:

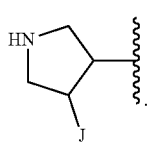

(78) A compound according to any one of (1) to (56), wherein -Q is:

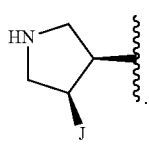

(79) A compound according to any one of (1) to (56), wherein -Q is:

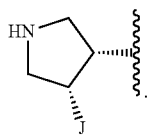

(80) A compound according to any one of (1) to (56), wherein -Q is:

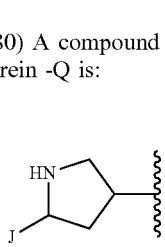

(81) A compound according to any one of (1) to (56), wherein -Q is:

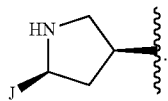

(82) A compound according to any one of (1) to (56), wherein -Q is:

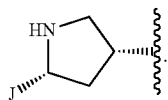

(83) A compound according to any one of (1) to (56), wherein -Q is:

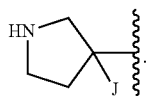

(84) A compound according to any one of (1) to (56), wherein -Q is:

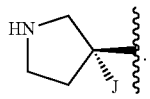

(85) A compound according to any one of (1) to (56), wherein -Q is:

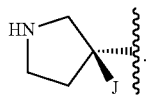

(86) A compound according to any one of (1) to (56), wherein -Q is selected from:

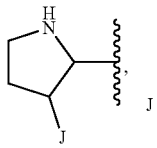 , 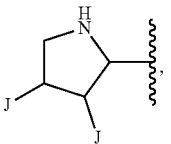 , and 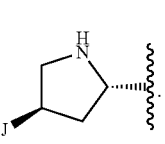 ,

(87) A compound according to any one of (1) to (56), wherein -Q is:

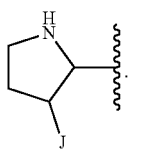

(88) A compound according to any one of (1) to (56), wherein -Q is:

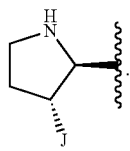

(89) A compound according to any one of (1) to (56), wherein -Q is:

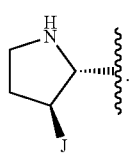

(90) A compound according to any one of (1) to (56), wherein -Q is:

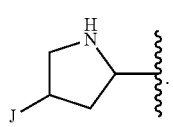

(91) A compound according to any one of (1) to (56), wherein -Q is:

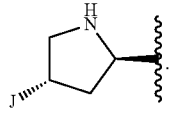

(92) A compound according to any one of (1) to (56), wherein -Q is:

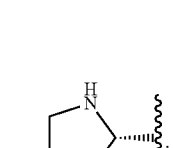

(93) A compound according to any one of (1) to (56), wherein -Q is:

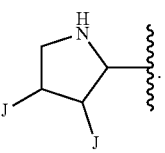

(94) A compound according to any one of (1) to (56), wherein -Q is:

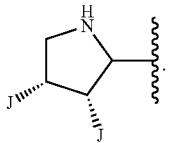

(95) A compound according to any one of (1) to (56), wherein -Q is:

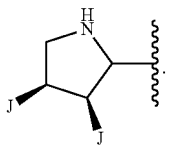

(96) A compound according to any one of (1) to (56), wherein -Q is:

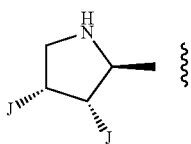

(97) A compound according to any one of (1) to (56), wherein -Q is:

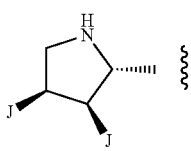

The Group -J

(98) A compound according to any one of (1) to (97), wherein each -J is independently —OH or —OR$^J$.

(99) A compound according to any one of (1) to (97), wherein each -J is independently —OH or -L$^J$-OH.

(100) A compound according to any one of (1) to (97), wherein each -J is independently -L$^J$-OH or -L$^J$-OR$^J$.

(101) A compound according to any one of (1) to (97), wherein each -J is —OH.

(102) A compound according to any one of (1) to (97), wherein each -J is —OR$^J$.

(103) A compound according to any one of (1) to (97), wherein each -J is -L$^J$-OH.

(104) A compound according to any one of (1) to (97), wherein each -J is -L$^J$-OR$^J$.

The Group —R$^J$ (105) A compound according to any one of (1) to (104), wherein each -Rd, if present, is independently linear or branched saturated $C_{1-4}$ alkyl or saturated $C_{3-6}$cycloalkyl.

(106) A compound according to any one of (1) to (104), wherein each -Rd, if present, is independently linear or branched saturated $C_{1-4}$ alkyl.

(107) A compound according to any one of (1) to (104), wherein each -Rd, if present, is independently -Me, -Et, -nPr, -iPr, -nBu, -iBu, -sBu, or -tBu.

(108) A compound according to any one of (1) to (104), wherein each -Rd, if present, is independently -Me, -Et, -nPr, or -iPr.

(109) A compound according to any one of (1) to (104), wherein each -Rd, if present, is independently -Me or -Et.

(110) A compound according to any one of (1) to (104), wherein each -Rd, if present, is -Me.

The Group -L$^J$-

(111) A compound according to any one of (1) to (110), wherein each -L$^J$-, if present, is independently linear or branched saturated $C_{1-4}$ alkylene.

(112) A compound according to any one of (1) to (110), wherein each -L$^J$-, if present, is independently —CH$_2$—, —CH(CH$_3$)—, —C(CH$_3$)$_2$—, —CH$_2$CH$_2$—, —CH(CH$_3$)CH$_2$—, —CH$_2$CH(CH$_3$)—, or —CH$_2$CH$_2$CH$_2$—.

(113) A compound according to any one of (1) to (110), wherein each -L$^J$-, if present, is independently —CH$_2$—, —CH(CH$_3$)—, —C(CH$_3$)$_2$—, or —CH$_2$CH$_2$—.

(114) A compound according to any one of (1) to (110), wherein each -L$^J$-, if present, is independently —CH$_2$—, —CH(CH$_3$)—, or —C(CH$_3$)$_2$—.

(115) A compound according to any one of (1) to (110), wherein each -L$^J$-, if present, is independently —CH$_2$— or —CH$_2$CH$_2$—.

(116) A compound according to any one of (1) to (110), wherein each -L$^J$-, if present, is independently —CH$_2$—.

The Group —R$^Q$ (117) A compound according to any one of (1) to (116), wherein each —R$^Q$, if present, is independently —F, —Cl, —Br, —I, —R$^{QA}$, —CF$_3$, —OH, —OR$^{QA}$, —OCF$_3$, —NH$_2$, —NHR$^{QA}$, —NR$^{QA}_2$, pyrrolidino, piperidino, morpholino, piperazino, or N—(R$^{QA}$)-piperazino.

(118) A compound according to any one of (1) to (116), wherein each —R$^Q$, if present, is independently —F, —Cl, —Br, —I, —R$^{QA}$, —OH, or —OR$^{QA}$.

(119) A compound according to any one of (1) to (116), wherein each —R$^Q$, if present, is independently —F, —Cl, —Br, or —I.

The Group —R$^{QA}$ (120) A compound according to any one of (1) to (119), wherein each —R$^{QA}$, if present, is independently linear or branched saturated $C_{1-4}$ alkyl or saturated $C_{3-6}$cycloalkyl.

(121) A compound according to any one of (1) to (119), wherein each —R$^{QA}$, if present, is independently linear or branched $C_{1-4}$ alkyl.

(122) A compound according to any one of (1) to (119), wherein each —R$^{QA}$, if present, is independently -Me, -Et, -nPr, -iPr, -nBu, -iBu, -sBu, or -tBu.

(123) A compound according to any one of (1) to (119), wherein each —R$^{QA}$, if present, is independently -Me, -Et, -nPr, or -iPr.

(124) A compound according to any one of (1) to (119), wherein each —R$^{QA}$, if present, is independently -Me or -Et.

(125) A compound according to any one of (1) to (119), wherein each —R$^{QA}$, if present, is independently -Me.

The Group —R$^{5Y}$ (126) A compound according to any one of (1) to (125), wherein —R$^{5Y}$ is —H.

(127) A compound according to any one of (1) to (125), wherein —R$^{5Y}$ is —R$^{5YA}$.

The Group —R$^{5YA}$ (128) A compound according to any one of (1) to (127), wherein —R$^{5YA}$, if present, is independently linear or branched saturated $C_{1-4}$ alkyl.

(129) A compound according to any one of (1) to (127), wherein —R$^{5YA}$, if present, is independently -Me, -Et, -nPr, -iPr, -nBu, -iBu, -sBu, or -tBu.

(130) A compound according to any one of (1) to (127), wherein —$R^{5YA}$, if present, is independently -Me, -Et, -nPr, or -iPr.

(131) A compound according to any one of (1) to (127), wherein —$R^{5YA}$, if present, is independently -Me or -Et.

(132) A compound according to any one of (1) to (127), wherein —$R^{5YA}$, if present, is independently -Me.

The Group —$R^7$ (133) A compound according to any one of (1) to (132), wherein —$R^7$ is —$R^{7X}$.

(134) A compound according to any one of (1) to (132), wherein —$R^7$ is —C(=O)$R^{7X}$.

The Group —$R^{7X}$ (135) A compound according to any one of (1) to (134), wherein each —$R^{7X}$ is independently:
—$R^{7B}$, —$R^{7C}$, —$R^{7D}$, —$R^{7E}$,
-$L^7$-$R^{7B}$, -$L^7$-$R^{7C}$, -$L^7$-$R^{7D}$, or -$L^7$-$R^{7E}$.

(136) A compound according to any one of (1) to (134), wherein each —$R^{7X}$ is independently:
—$R^{7C}$, —$R^{7D}$, —$R^{7E}$,
$L^7$-$R^{7B}$, -$L^7$-$R^{7D}$, or -$L^7$-$R^{7E}$.

(137) A compound according to any one of (1) to (134), wherein each —$R^{7X}$ is independently:
-$L^7$-$R^{7B}$, -$L^7$-$R^{7D}$, or -$L^7$-$R^{7E}$.

(138) A compound according to any one of (1) to (134), wherein each —$R^{7X}$ is -$L^7$-$R^{7D}$.

(139) A compound according to any one of (1) to (134), wherein each —$R^{7X}$ is —$R^{7A}$.

(140) A compound according to any one of (1) to (134), wherein each —$R^{7X}$ is —$R^{7B}$.

(141) A compound according to any one of (1) to (134), wherein each —$R^{7X}$ is —$R^{7C}$.

(142) A compound according to any one of (1) to (134), wherein each —$R^{7X}$ is —$R^{7D}$.

(143) A compound according to any one of (1) to (134), wherein each —$R^{7X}$ is —$R^{7E}$.

(144) A compound according to any one of (1) to (134), wherein each —$R^{7X}$ is -$L^7$-$R^{7B}$.

(145) A compound according to any one of (1) to (134), wherein each —$R^{7X}$ is -$L^7$-$R^{7C}$.

(146) A compound according to any one of (1) to (134), wherein each —$R^{7X}$ is -$L^7$-$R^{7D}$.

(147) A compound according to any one of (1) to (134), wherein each —$R^{7X}$ is -$L^7$-$R^{7E}$.

The Group -$L^7$-

(148) A compound according to any one of (1) to (147), wherein each -$L^7$-, if present, is independently linear or branched saturated $C_{1-4}$ alkylene.

(149) A compound according to any one of (1) to (147), wherein each -$L^7$-, if present, is independently —$CH_2$—, —CH($CH_3$)—, —C($CH_3$)$_2$—, —$CH_2CH_2$—, —CH($CH_3$)$CH_2$—, —$CH_2$CH($CH_3$)—, or —$CH_2CH_2CH_2$—.

(150) A compound according to any one of (1) to (147), wherein each -$L^7$-, if present, is independently —$CH_2$—, —CH($CH_3$)—, —C($CH_3$)$_2$—, or —$CH_2CH_2$—.

(151) A compound according to any one of (1) to (147), wherein each -$L^7$-, if present, is independently —$CH_2$—, —CH($CH_3$)—, or —C($CH_3$)$_2$—.

(152) A compound according to any one of (1) to (147), wherein each -$L^7$-, if present, is independently —$CH_2$— or —$CH_2CH_2$—.

(153) A compound according to any one of (1) to (147), wherein each -$L^7$-, if present, is —$CH_2$—.

The Group —$R^{7A}$ (154) A compound according to any one of (1) to (153), wherein each —$R^{7A}$, if present, is independently linear or branched saturated $C_{1-6}$alkyl.

(155) A compound according to any one of (1) to (153), wherein each —$R^{7A}$, if present, is independently linear or branched saturated $C_{1-4}$ alkyl, and is optionally substituted with one or more substituents —$W^1$.

(156) A compound according to any one of (1) to (153), wherein each —$R^{7A}$, if present, is independently linear or branched saturated $C_{1-4}$ alkyl.

(157) A compound according to any one of (1) to (153), wherein each —$R^{7A}$, if present, is independently -Me, -Et, -nPr, -iPr, -nBu, -iBu, -sBu, or -tBu, and is optionally substituted with one or more substituents —$W^1$.

(158) A compound according to any one of (1) to (153), wherein each —$R^{7A}$, if present, is independently -Me, -Et, -nPr, -iPr, -nBu, -iBu, -sBu, or -tBu.

(159) A compound according to any one of (1) to (153), wherein each —$R^{7A}$, if present, is independently -Me, -Et, -nPr, or -iPr, and is optionally substituted with one or more substituents —$W^1$.

(160) A compound according to any one of (1) to (153), wherein each —$R^{7A}$, if present, is independently -Me, -Et, -nPr, or -iPr.

(161) A compound according to any one of (1) to (153), wherein each —$R^{7A}$, if present, is independently -Me or -Et, and is optionally substituted with one or more substituents —$W^1$.

(162) A compound according to any one of (1) to (153), wherein each —$R^{7A}$, if present, is independently -Me or -Et.

(163) A compound according to any one of (1) to (153), wherein each —$R^{7A}$, if present, is -Me, and is optionally substituted with one or more substituents —$W^1$.

(164) A compound according to any one of (1) to (153), wherein each —$R^{7A}$, if present, is -Me.

The Group —$R^{7B}$ (165) A compound according to any one of (1) to (164), wherein each —$R^{7B}$, if present, is independently cyclopropyl, cyclobutyl, cyclopentyl, or cyclohexyl, and is optionally substituted with one or more substituents —$W^2$.

(166) A compound according to any one of (1) to (164), wherein each —$R^{7B}$, if present, is independently cyclopropyl, cyclobutyl, cyclopentyl, or cyclohexyl.

(167) A compound according to any one of (1) to (164), wherein each —$R^{7B}$, if present, is independently cyclopentyl or cyclohexyl, and is optionally substituted with one or more substituents —$W^2$.

(168) A compound according to any one of (1) to (164), wherein each —$R^{7B}$, if present, is independently cyclopentyl or cyclohexyl.

(169) A compound according to any one of (1) to (164), wherein each —$R^{7B}$, if present, is cyclohexyl, and is optionally substituted with one or more substituents —$W^2$.

(170) A compound according to any one of (1) to (164), wherein each —$R^{7B}$, if present, is cyclohexyl.

The Group —$R^{7C}$ (171) A compound according to any one of (1) to (170), wherein each —$R^{7C}$, if present, is independently pyrrolidinyl, piperidinyl, morpholinyl, piperazinyl, tetrahydrofuranyl, tetrahydropyranyl, dixoanyl, azepanyl, or diazepanyl, and is optionally substituted with one or more substituents —$W^2$.

(172) A compound according to any one of (1) to (170), wherein each —$R^{7C}$, if present, is independently pyrrolidinyl, piperidinyl, morpholinyl, piperazinyl, tetrahydrofuranyl, tetrahydropyranyl, or dixoanyl, and is optionally substituted with one or more substituents —$W^2$.

(173) A compound according to any one of (1) to (170), wherein each —$R^{7C}$, if present, is independently pyrrolidinyl, piperidinyl, morpholinyl, or piperazinyl, and is optionally substituted with one or more substituents —$W^2$.

(174) A compound according to any one of (1) to (170), wherein each —$R^{7C}$, if present, is independently piperidinyl, and is optionally substituted with one or more substituents —$W^2$.

The Group —$R^{7D}$
(175) A compound according to any one of (1) to (174), wherein each —$R^{7D}$, if present, is phenyl, and is optionally substituted with one or more substituents —$W^3$.

(176) A compound according to any one of (1) to (174), wherein each —$R^{7D}$, if present, is phenyl.

(177) A compound according to any one of (1) to (174), wherein each —$R^{7D}$, if present, is naphthyl, and is optionally substituted with one or more substituents —$W^3$.

(178) A compound according to any one of (1) to (174), wherein each —$R^{7D}$, if present, is naphthyl.

The Group —$R^{7E}$
(179) A compound according to any one of (1) to (178), wherein each —$R^{7E}$, if present, is $C_{5-10}$ heteroaryl, and is optionally substituted with one or more substituents —$W^3$.

(180) A compound according to any one of (1) to (178), wherein each —$R^{7E}$, if present, is $C_{5-10}$ heteroaryl.

(181) A compound according to any one of (1) to (178), wherein each —$R^{7E}$, if present, is $C_{5-6}$ heteroaryl, and is optionally substituted with one or more substituents —$W^3$.

(182) A compound according to any one of (1) to (178), wherein each —$R^{7E}$, if present, is $C_{5-6}$ heteroaryl.

(183) A compound according to any one of (1) to (178), wherein each —$R^{7E}$, if present, is $C_{9\text{–}10}$ heteroaryl, and is optionally substituted, for example, with one or more substituents —$W^3$.

(184) A compound according to any one of (1) to (178), wherein each —$R^{7E}$, if present, is $C_{9\text{–}10}$ heteroaryl.

(185) A compound according to any one of (1) to (178), wherein each —$R^{7E}$, if present, is independently furanyl, thienyl, pyrrolyl, imidazolyl, pyrazolyl, oxazolyl, isoxazolyl, thiazolyl, isothiazolyl, triazolyl (e.g., 1H-[1,2,3]triazolyl, 2H-[1,2,3]triazolyl, 4H-[1,2,4]triazolyl, 1H-[1,2,4]triazolyl), oxadiazolyl (e.g., [1,2,3]oxadiazolyl, furazanyl, [1,3,4]oxadiazolyl, [1,2,4]oxadiazolyl), thiadiazolyl (e.g., [1,2,3]thiadiazolyl, [1,2,5]thiadiazolyl, [1,3,4]thiadiazolyl, [1,2,4]thiadiazolyl), tetrazolyl, pyridyl, pyrimidinyl, pyrazinyl, pyridazinyl, or triazinyl (e.g., [1,3,5]-triazinyl), and is optionally substituted with one or more substituents —$W^3$.

(186) A compound according to any one of (1) to (178), wherein each —$R^{7E}$, if present, is independently furanyl, thienyl, pyrrolyl, imidazolyl, pyrazolyl, oxazolyl, isoxazolyl, thiazolyl, isothiazolyl, pyridyl, pyrimidinyl, pyrazinyl, or pyridazinyl, and is optionally substituted, for example, with one or more substituents —$W^3$.

(187) A compound according to any one of (1) to (178), wherein each —$R^{7E}$, if present, is independently furanyl, thienyl, pyrrolyl, imidazolyl, pyrazolyl, oxazolyl, isoxazolyl, thiazolyl, or isothiazolyl, and is optionally substituted, for example, with one or more substituents —$W^3$.

(188) A compound according to any one of (1) to (178), wherein each —$R^{7E}$, if present, is independently pyridyl, pyrimidinyl, pyrazinyl, or pyridazinyl, and is optionally substituted, for example, with one or more substituents —$W^3$.

(189) A compound according to any one of (1) to (178), wherein each —$R^{7E}$, if present, is independently indolyl, indazolyl, benzofuranyl, benzothienyl, benzimidazolyl, benzothiazolyl, benzoxazolyl, benzoisoxazolyl, quinolinyl, isoquinolinyl, cinnolinyl, quinazolinyl, phthalazinyl, or quinoxalinyl, and is optionally substituted, for example, with one or more substituents —$W^3$.

(190) A compound according to any one of (1) to (178), wherein each —$R^{7E}$, if present, is benzothiazolyl, and is optionally substituted, for example, with one or more substituents —$W^3$.

The Group —$W^1$
(191) A compound according to any one of (1) to (190), wherein each —$W^1$, if present, is independently: —F, —Cl, —Br, —I, —$CF_3$, —OH, —$OR^{W1}$, —$OCF_3$, —$NH_2$, —$NHR^{W1}$, —$NR^{W1}_2$, pyrrolidino, piperidino, morpholino, piperazino, or N—($R^{W1}$)-piperazino.

(192) A compound according to any one of (1) to (190), wherein each —$W^1$, if present, is independently: —F, —Cl, —Br, —I, —$CF_3$, —OH, —$OR^{W1}$, or —$OCF_3$.

The Group —$R^{W1}$
(193) A compound according to any one of (1) to (192), wherein each —$R^{W1}$, if present, is independently linear or branched saturated $C_{1-4}$ alkyl, phenyl, or —$CH_2$-phenyl, wherein each phenyl is optionally substituted with one or more groups selected from —F, —Cl, —Br, —I, —$R^{W11}$, —$CF_3$, —OH, —$OR^{W11}$, and —$OCF_3$, wherein each —$R^{W11}$ is independently linear or branched saturated $C_{1-4}$ alkyl.

(194) A compound according to any one of (1) to (192), wherein each —$R^{W1}$, if present, is independently linear or branched saturated $C_{1-4}$ alkyl, phenyl, or —$CH_2$-phenyl.

(195) A compound according to any one of (1) to (192), wherein each —$R^{W1}$, if present, is independently linear or branched saturated $C_{1-4}$ alkyl.

(196) A compound according to any one of (1) to (192), wherein each —$R^{W1}$, if present, is independently -Me, -Et, -nPr, -iPr, -nBu, -iBu, -sBu, or -tBu.

(197) A compound according to any one of (1) to (192), wherein each —$R^{W1}$, if present, is independently -Me, -Et, -nPr, or -iPr.

(198) A compound according to any one of (1) to (192), wherein each —$R^{W1}$, if present, is independently -Me or -Et.

(199) A compound according to any one of (1) to (192), wherein each —$R^{W1}$, if present, is -Me.

The Group —$R^{W11}$
(200) A compound according to any one of (1) to (199), wherein each —$R^{W11}$, if present, is independently linear or branched saturated $C_{1-4}$ alkyl.

(201) A compound according to any one of (1) to (199), wherein each —$R^{W11}$, if present, is independently -Me, -Et, -nPr, -iPr, -nBu, -iBu, -sBu, or -tBu.

(202) A compound according to any one of (1) to (199), wherein each —$R^{W11}$, if present, is independently -Me, -Et, -nPr, or -iPr.

(203) A compound according to any one of (1) to (199), wherein each —$R^{W11}$, if present, is independently -Me or -Et.

(204) A compound according to any one of (1) to (199), wherein each —$R^{W11}$, if present, is -Me.

The Group —$W^2$
(205) A compound according to any one of (1) to (204), wherein each —$W^2$, if present, is independently: —F, —Cl, —Br, —I, —$CF_3$, —OH, —$OR^{W2}$, —$OCF_3$, —$NH_2$, —$NHR^{W2}$, —$NR^{W2}_2$, pyrrolidino, piperidino, morpholino, piperazino, or N—($R^{W2}$)-piperazino.

(206) A compound according to any one of (1) to (204), wherein each —$W^2$, if present, is independently: —F, —Cl, —Br, —I, —$CF_3$, —OH, —$OR^{W2}$, or —$OCF_3$.

The Group —$R^{W2}$
(207) A compound according to any one of (1) to (206), wherein each —$R^{W2}$, if present, is independently linear or branched saturated $C_{1-4}$ alkyl, phenyl, or —$CH_2$-phenyl, wherein each phenyl is optionally substituted with one or more groups selected from —F, —Cl, —Br, —I, —$R^{W22}$, —$CF_3$, —OH, —$OR^{W22}$, and —$OCF_3$, wherein each —$R^{W22}$ is independently linear or branched saturated $C_{1-4}$ alkyl.

(208) A compound according to any one of (1) to (206), wherein each —$R^{W2}$, if present, is independently linear or branched saturated $C_{1-4}$ alkyl, phenyl, or —$CH_2$-phenyl.

(209) A compound according to any one of (1) to (206), wherein each —$R^{W2}$, if present, is independently linear or branched saturated $C_{1-4}$ alkyl.

(210) A compound according to any one of (1) to (206), wherein each —$R^{W2}$, if present, is independently -Me, -Et, -nPr, -iPr, -nBu, -iBu, -sBu, or -tBu.

(211) A compound according to any one of (1) to (206), wherein each —$R^{W2}$, if present, is independently -Me, -Et, -nPr, or -iPr.

(212) A compound according to any one of (1) to (206), wherein each —$R^{W2}$, if present, is independently -Me or -Et.

(213) A compound according to any one of (1) to (206), wherein each —$R^{W2}$, if present, is -Me.

The Group —$R^{W22}$ (214) A compound according to any one of (1) to (213), wherein each —$R^{W22}$, if present, is independently linear or branched saturated $C_{1-4}$ alkyl.

(215) A compound according to any one of (1) to (213), wherein each —$R^{W22}$, if present, is independently -Me, -Et, -nPr, -iPr, -nBu, -iBu, -sBu, or -tBu.

(216) A compound according to any one of (1) to (213), wherein each —$R^{W22}$, if present, is independently -Me, -Et, -nPr, or -iPr.

(217) A compound according to any one of (1) to (213), wherein each —$R^{W22}$, if present, is independently -Me or -Et.

(218) A compound according to any one of (1) to (213), wherein each —$R^{W22}$, if present, is -Me.

The Group —$W^3$ (219) A compound according to any one of (1) to (218), wherein each —$W^3$, if present, is independently: —F, —Cl, —Br, —I, —$CF_3$, —OH, —$OR^{W3}$, —$OCF_3$, —$NH_2$, —$NHR^{W3}$, —$NR^{W3}_2$, pyrrolidino, piperidino, morpholino, piperazino, or N—($R^{W3}$)-piperazino.

(220) A compound according to any one of (1) to (218), wherein each —$W^3$, if present, is independently: —F, —Cl, —Br, —I, —$CF_3$, —OH, —$OR^{W3}$, or —$OCF_3$.

The Group —$R^{W3}$ (221) A compound according to any one of (1) to (220), wherein each —$R^{W3}$, if present, is independently linear or branched saturated $C_{1-4}$ alkyl, phenyl, or —$CH_2$-phenyl, wherein each phenyl is optionally substituted with one or more groups selected from —F, —Cl, —Br, —I, —$R^{W33}$, —$CF_3$, —OH, —$OR^{W33}$, and —$OCF_3$, wherein each —$R^{W33}$ is independently linear or branched saturated $C_{1-4}$ alkyl.

(222) A compound according to any one of (1) to (220), wherein each —$R^{W3}$, if present, is independently linear or branched saturated $C_{1-4}$ alkyl, phenyl, or —$CH_2$-phenyl.

(223) A compound according to any one of (1) to (220), wherein each —$R^{W3}$, if present, is independently linear or branched saturated $C_{1-4}$ alkyl.

(224) A compound according to any one of (1) to (220), wherein each —$R^{W3}$, if present, is independently linear or branched saturated $C_{1-4}$ alkyl.

(225) A compound according to any one of (1) to (220), wherein each —$R^{W3}$, if present, is -Me.

The Group —$R^{W33}$ (226) A compound according to any one of (1) to (225), wherein each —$R^{W33}$, if present, is independently linear or branched saturated $C_{1-4}$ alkyl.

(227) A compound according to any one of (1) to (225), wherein each —$R^{W33}$, if present, is independently -Me, -Et, -nPr, -iPr, -nBu, -iBu, -sBu, or -tBu.

(228) A compound according to any one of (1) to (225), wherein each —$R^{W33}$, if present, is independently -Me, -Et, -nPr, or -iPr.

(229) A compound according to any one of (1) to (225), wherein each —$R^{W33}$, if present, is independently -Me or -Et.

(230) A compound according to any one of (1) to (225), wherein each —$R^{W33}$, if present, is -Me.

The Group —$R^3$ (231) A compound according to any one of (1) to (230), wherein —$R^3$ is —$R^{3A}$.

(232) A compound according to any one of (1) to (230), wherein —$R^3$ is —$R^{3B}$.

The Group —$R^{3A}$ (233) A compound according to any one of (1) to (232), wherein —$R^{3A}$, if present, is independently -Me, -Et, -nPr, -iPr, -nBu, -iBu, -sBu, or -tBu, n-pentyl, t-pentyl, neo-pentyl, iso-pentyl, sec-pentyl, 3-pentyl, 1-hexyl, 2-hexyl, 3-hexyl, 3-methyl-1-pentyl, 4-methyl-1-pentyl, 4-methyl-2-pentyl, 4-methyl-3-pentyl, 2-methyl-2-pentyl, 2-methyl-1-pentyl, 2-methyl-2-pentyl, 3,3-dimethyl-1-butyl, 3,3-dimethyl-2-butyl, 3-methyl-1-pentyl, 3-methyl-2-pentyl, 3-methyl-3-pentyl, 2,2-dimethyl-1-butyl, 2,3-dimethyl-1-butyl, or 2,3-dimethyl-2-butyl.

(234) A compound according to any one of (1) to (232), wherein —$R^{3A}$, if present, is independently linear or branched saturated $C_{1-4}$ alkyl.

(235) A compound according to any one of (1) to (232), wherein —$R^{3A}$, if present, is independently -Me, -Et, -nPr, -iPr, -nBu, -iBu, -sBu, or -tBu.

(236) A compound according to any one of (1) to (232), wherein —$R^{3A}$, if present, is independently -Me, -Et, -nPr, or -iPr.

(237) A compound according to any one of (1) to (232), wherein —$R^{3A}$, if present, is -iPr.

The Group —$R^{3B}$ (238) A compound according to any one of (1) to (237), wherein —$R^{3B}$, if present, is independently cyclopropyl, cyclobutyl, cyclopentyl, or cyclohexyl.

(239) A compound according to any one of (1) to (237), wherein —$R^{3B}$, if present, is independently cyclopropyl or cyclobutyl.

(240) A compound according to any one of (1) to (237), wherein —$R^{3B}$, if present, is cyclopropyl.

(241) A compound according to any one of (1) to (237), wherein —$R^{3B}$, if present, is cyclobutyl.

The Group —$R^2$ (242) A compound according to any one of (1) to (241), wherein —$R^2$ is —H.

(243) A compound according to any one of (1) to (241), wherein —$R^2$ is —$R^{2A}$. The Group —$R^{2A}$ (244) A compound according to any one of (1) to (243), wherein —$R^{2A}$, if present, is independently —F, —Cl, —Br, —I, —$R^{2AA}$, —$CF_3$, —OH, —$OR^{2AA}$, —$OCF_3$, —$NH_2$, —$NHR^{2AA}$, —$NR^{2AA}_2$, pyrrolidino, piperidino, morpholino, piperazino, or N—($R^{2AA}$)-piperazino.

(245) A compound according to any one of (1) to (243), wherein —$R^{2A}$, if present, is independently —F, —Cl, —Br, —I, —$R^{2AA}$, —OH, or —$OR^{2AA}$.

(246) A compound according to any one of (1) to (243), wherein —$R^{2A}$, if present, is independently —F, —Cl, —Br, or —I.

The Group —$R^{2AA}$ (247) A compound according to any one of (1) to (246), wherein each —$R^{2AA}$, if present, is independently linear or branched saturated $C_{1-4}$ alkyl.

(248) A compound according to any one of (1) to (246), wherein each —$R^{2AA}$, if present, is independently -Me, -Et, -nPr, -iPr, -nBu, -iBu, -sBu, or -tBu.

(249) A compound according to any one of (1) to (246), wherein each —$R^{2AA}$, if present, is independently -Me, -Et, -nPr, or -iPr.

(250) A compound according to any one of (1) to (246), wherein each —$R^{2AA}$, if present, is independently -Me or -Et.

(251) A compound according to any one of (1) to (246), wherein each —$R^{2AA}$, if present, is -Me.

The Group —$R^6$ (252) A compound according to any one of (1) to (251), wherein —$R^6$ is —H.

(253) A compound according to any one of (1) to (251), wherein —$R^6$ is —$R^{6A}$.

The Group —$R^{6A}$ (254) A compound according to any one of (1) to (253), wherein —$R^{6A}$, if present, is independently —F, —Cl, —Br, —I, —$R^{6AA}$, —$CF_3$, —OH, —$OR^{6AA}$, —$OCF_3$, —$NH_2$, —$NHR^{6AA}$, —$NR^{6AA}_2$, pyrrolidino, piperidino, morpholino, piperazino, or N—($R^{6AA}$)-piperazino.

(255) A compound according to any one of (1) to (253), wherein —$R^{6A}$, if present, is independently —F, —Cl, —Br, —I, —$R^{6AA}$, —OH, or —$OR^{6AA}$.

(256) A compound according to any one of (1) to (253), wherein —$R^{6A}$, if present, is independently —F, —Cl, —Br, or —I.

The Group —$R^{6AA}$ (257) A compound according to any one of (1) to (256), wherein each —$R^{6AA}$, if present, is independently linear or branched saturated $C_{1-4}$ alkyl.

(258) A compound according to any one of (1) to (256), wherein each —$R^{6AA}$, if present, is independently -Me, -Et, -nPr, -iPr, -nBu, -iBu, -sBu, or -tBu.

(259) A compound according to any one of (1) to (256), wherein each —$R^{6AA}$, if present, is independently -Me, -Et, -nPr, or -iPr.

(260) A compound according to any one of (1) to (256), wherein each —$R^{6AA}$, if present, is independently -Me or -Et.

(261) A compound according to any one of (1) to (256), wherein each —$R^{6AA}$, if present, is -Me.

Specific Compounds (262) A compound according to (1), selected from compounds of the following formulae and pharmaceutically acceptable salts, hydrates, and solvates thereof:

| Compound No. | Structure |
|---|---|
| PPDA-001 | 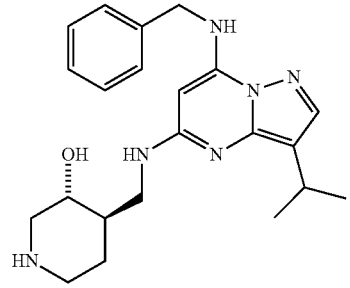 [SMILES: CC(C)c1cnn2c(NCc3ccccc3)cc(NC[C@H]3CCNC[C@@H]3O)nc12] |
| PPDA-002 | 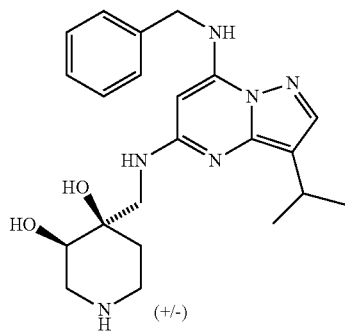 |
| PPDA-003 | 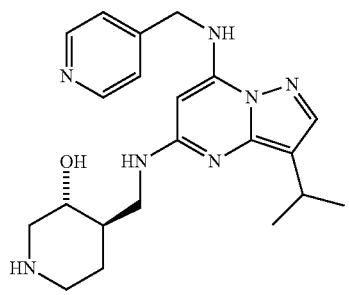 [SMILES: CC(C)c1cnn2c(NCc3ccncc3)cc(NC[C@H]3CCNC[C@@H]3O)nc12] |
| PPDA-004 | 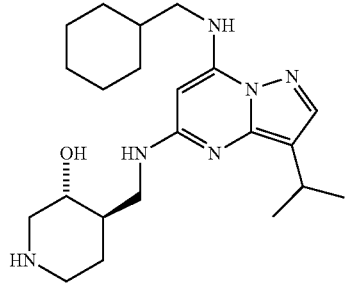 [SMILES: CC(C)c1cnn2c(NCC3CCCCC3)cc(NC[C@H]3CCNC[C@@H]3O)nc12] |
| PPDA-005 | 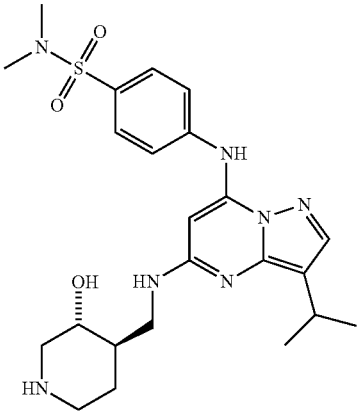 [SMILES: CC(C)c1cnn2c(Nc3ccc(S(=O)(=O)N(C)C)cc3)cc(NC[C@H]3CCNC[C@@H]3O)nc12] |

-continued
| Compound No. | Structure |
|---|---|
| PPDA-006 | 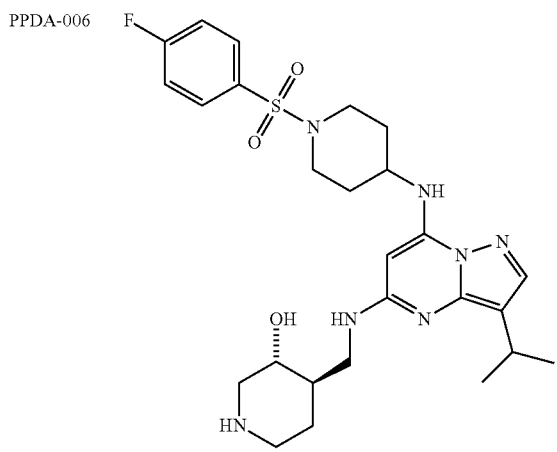 |
| PPDA-007 | 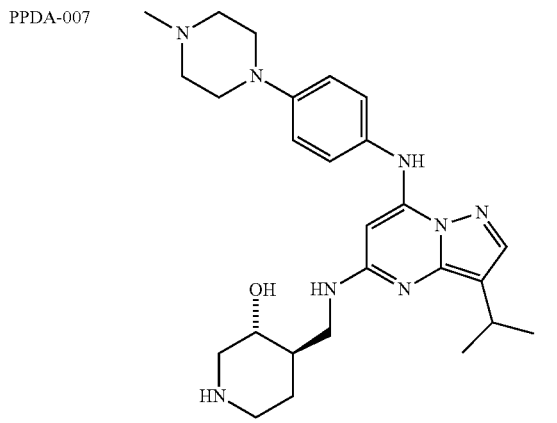 |
| PPDA-008 | 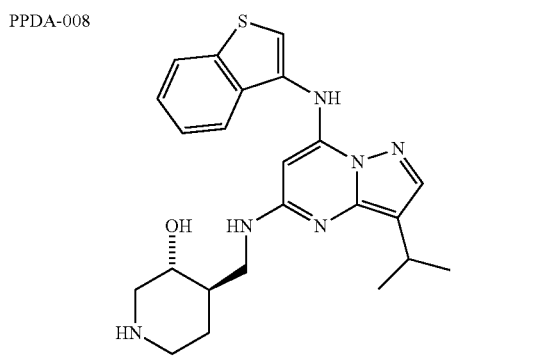 |
| PPDA-009 | 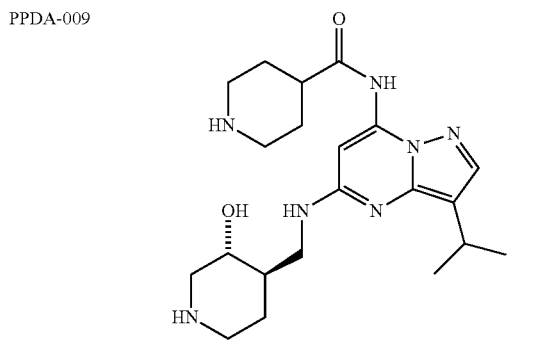 |
-continued
| Compound No. | Structure |
|---|---|
| PPDA-010 | 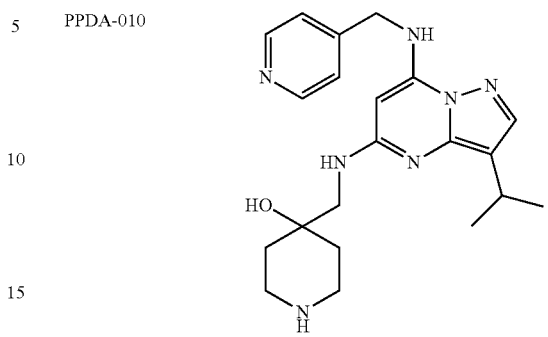 |
| PPDA-011 | 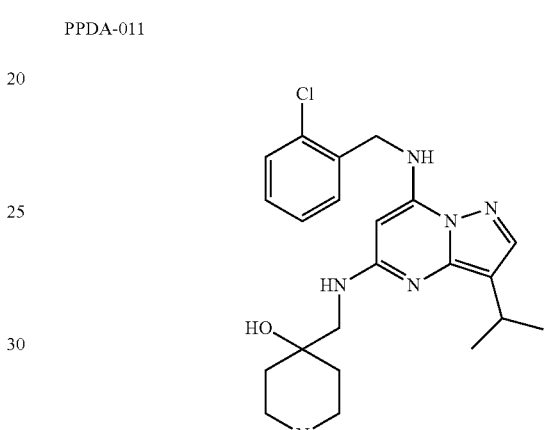 |
| PPDA-012 | 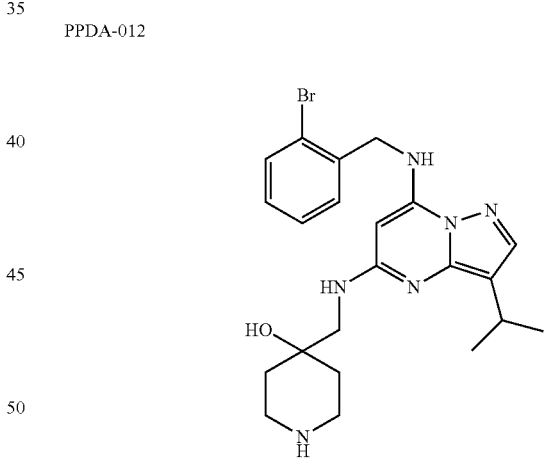 |
| PPDA-013 | 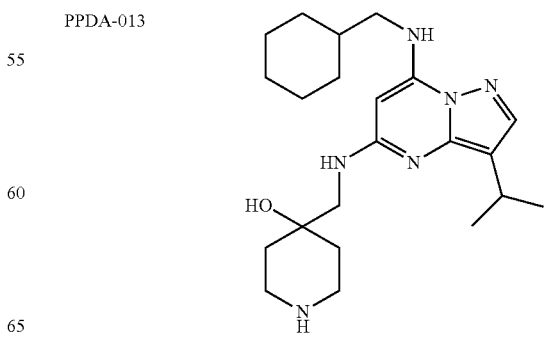 |

-continued

| Compound No. | Structure |
|---|---|
| PPDA-014 | (structure shown, +/-) |
| PPDA-015 | (structure shown) |
| PPDA-016 | (structure shown) |
| PPDA-017 | (structure shown) |
| PPDA-018 | (structure shown, +/-) |
| PPDA-019 | (structure shown, +/-) |
| PPDA-020 | (structure shown, +/-) |
| PPDA-021 | (structure shown, +/-) |
| PPDA-022 | (structure shown) |
| PPDA-023 | (structure shown) |

| Compound No. | Structure |
|---|---|
| PPDA-024 | 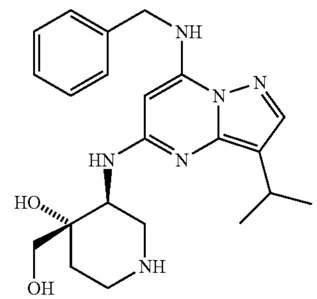 [SMILES: CC(C)c1cnn2c(NCc3ccccc3)cc(N[C@H]3CNCC[C@@]3(O)CO)nc12] |
| PPDA-025 | 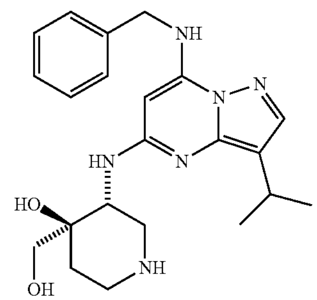 |
| PPDA-026 | 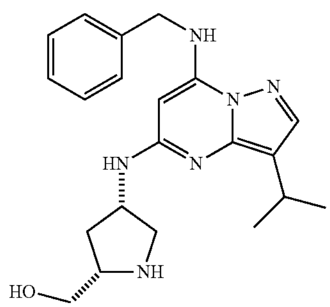 |
| PPDA-027 | 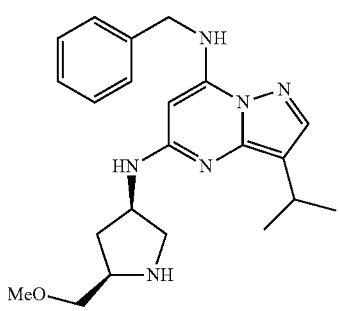 [SMILES: COC[C@H]1C[C@@H](Nc2cc(NCc3ccccc3)n3ncc(C(C)C)c3n2)CN1] |
| PPDA-028 | 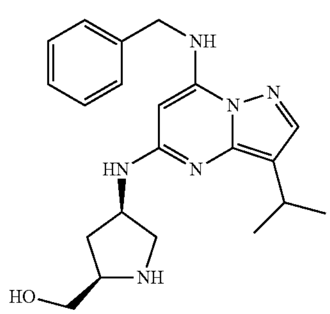 |
| PPDA-029 | |
| PPDA-030 | |
| PPDA-031 | |
| PPDA-032 | |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., —$R^2$, —$R^3$, —$R^{5X}$, —$R^{5Y}$, —$R^6$, —$R^7$, -$L^{5X}$-, -$L^{5XA}$-, —$R^{L5X}$, -Q, n, -J, m, —$R^Q$, —$R^J$, -$L^J$-, —$R^{QA}$, —$R^{5YA}$, —$R^{7X}$, —$R^{7A}$, —$R^{7B}$, —$R^{7C}$, —$R^{7D}$, —$R^{7E}$, -$L^7$-, —$W^1$, —$W^2$, —$W^3$, —$R^{W1}$, —$R^{W11}$, —$R^{W2}$, —$R^{W22}$, —$R^{W3}$, —$R^{W33}$, —$R^{3A}$, —$R^{3B}$, —$R^{2A}$, —$R^{2AA}$, —$R^{6A}$, —$R^{6AA}$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In this context, the skilled person will readily appreciate that certain combinations of groups (e.g., substituents) may give rise to compounds which may not be readily synthesized and/or are chemically unstable. In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to PPDA compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless otherwise specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to a equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diastereoisomeric, epimeric, atropic, stereoisomeric, tautomeric, conformational, or anomeric forms, including but not limited to, cis- and trans-forms; E- and Z-forms; c-, t-, and r- forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

A reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

However, reference to a specific group or substitution pattern is not intended to include other structural (or constitutional isomers) which differ with respect to the connections between atoms rather than by positions in space. For example, a reference to a methoxy group, —$OCH_3$, is not to be construed as a reference to its structural isomer, a hydroxymethyl group, —$CH_2OH$. Similarly, a reference specifically to ortho-chlorophenyl is not to be construed as a reference to its structural isomer, meta-chlorophenyl.

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro. A reference herein to one tautomer is intended to encompass both tautomers.

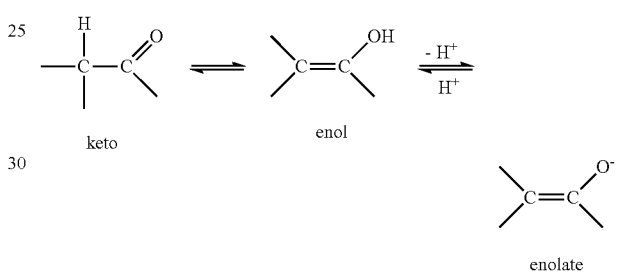

For example, 1H-pyridin-2-one-5-yl and 2-hydroxyl-pyridin-5-yl (shown below) are tautomers of one another. A reference herein to one is intended to encompass both.

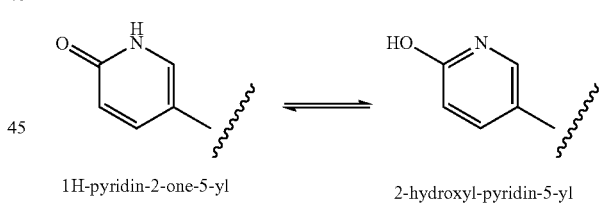

1H-pyridin-2-one-5-yl     2-hydroxyl-pyridin-5-yl

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group, which may be anionic (e.g., —COOH may be —COO⁻), then a salt may be formed with a suitable cation.

Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$ as well as the ammonium ion (i.e., $NH_4^+$). Examples of suitable organic cations include, but are not limited to substituted ammonium ions (e.g., $NH_3R^+$, $NH_2R^{2+}$, $NHR_3^+$, $NR_4^+$), for example, where each R is independently linear or branched saturated $C_{1-18}$alkyl, $C_{3-8}$cycloalkyl, $C_{3-8}$cycloalkyl-$C_{1-6}$alkyl, and phenyl-$C_{1-6}$alkyl, wherein the phenyl group is optionally substituted. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group, which upon protonation may become cationic (e.g., —$NH_2$ may become —$NH_3^+$), then a salt may be formed with a suitable anion.

For example, if a parent structure contains a cationic group (e.g., —$NMe_2^+$), or has a functional group, which upon protonation may become cationic (e.g., —$NH_2$ may become —$NH_3+$), then a salt may be formed with a suitable anion. In the case of a quaternary ammonium compound a counter-anion is generally always present in order to balance the positive charge. If, in addition to a cationic group (e.g., —$NMe_2^+$, —$NH_3^+$), the compound also contains a group capable of forming an anion (e.g., —COOH), then an inner salt (also referred to as a zwitterion) may be formed.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyloxybenzoic, acetic, trifluoroacetic, ascorbic, aspartic, benzoic, camphorsulfonic, cinnamic, citric, edetic, 1,2-ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Examples of suitable counter-ions which are especially suitable for quaternary ammonium compounds (e.g., those with a —$NMe_2^+$ group) include 1-adamantanesulfonate, benzenesulfonate, bisulfate, bromide, chloride, iodide, methanesulfonate, methylsulfate, 1,5-napthalene-bis-sulfonate, 4-nitrobenzenesulfonate, formate, tartrate, tosylate, trifluoroacetate, trifluoromethylsulfonate, sulphate. Again, if the compound also contains a group capable of forming an anion (e.g., —COOH), then an inner salt may be formed.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well-known chemical methods are employed to reversibly render unreactive a functional group, which otherwise would be reactive, under specified conditions. In a chemically protected form, one or more reactive functional groups are in the form of a protected or protecting group (alternatively as a masked or masking group or a blocked or blocking group). By protecting a reactive functional group, reactions involving other unprotected reactive functional groups can be performed, without affecting the protected group; the protecting group may be removed or the masking group transformed, usually in a subsequent step, without substantially affecting the remainder of the molecule. See, for example, *Protective Groups in Organic Synthesis* (T. Green and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)$CH_3$, —OAc).

For example, an aldehyde or ketone group may be protected as an acetal (R—CH(OR)$_2$) or ketal ($R^2C(OR)_2$), respectively, in which the carbonyl group (>C=O) is converted to a 1,1-diether (>C(OR)$_2$), by reaction with, for example, a primary alcohol in the presence of an acid. The aldehyde or ketone group is readily regenerated, for example, by hydrolysis using water in the presence of acid.

For example, an amine group may be protected, for example, as an amide (—NRCO—R) or a urethane (—NRCO—OR), for example, as: an acetamide (—NHCO—$CH_3$); a benzyloxy amide (—NHCO—$OCH_2C_6H_5$, —NH-Cbz); as a t-butoxy amide (—NHCO—$OC(CH_3)_3$, —NH-Boc); a 2-biphenyl-2-propoxy amide (—NHCO—$OC(CH_3)_2C_6H_4C_6H_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH—Psec); or, in suitable cases (e.g., cyclic amines), as a nitroxide radical (>N—O.).

For example, a carboxylic acid group may be protected as an ester for example, as: an $C_{1-7}$ alkyl ester (e.g., a methyl ester; a t-butyl ester); a $C_{1-7}$ haloalkyl ester (e.g., a 2,2,2-trihaloethyl ester); a 2-tri($C_{1-7}$alkyl)silyl-ethyl ester; or a $C_{5-20}$ aryl-$C_{1-7}$ alkyl ester (e.g., a benzyl ester; a nitrobenzyl ester); or as an amide or hydrazide, for example, as acetamide or a N,N,N'-trimethylhydrazide.

For example, a thiol group may be protected as a thioether (—SR), for example, as: a benzyl thioether; an acetamidomethyl ether (—S—CH$_2$NHC(=O)CH$_3$).

Prodrugs

It may be convenient or desirable to prepare, purify, and/or handle the compound in the form of a prodrug. The term "prodrug," as used herein, pertains to a compound, which yields the desired active compound in vivo. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound, which, upon further chemical reaction, yields the active compound (for example, as in antibody directed enzyme prodrug therapy (ADEPT), gene directed enzyme prodrug therapy (GDEPT), lipid directed enzyme prodrug therapy (LIDEPT), etc.). For example, the prodrug may be a sugar derivative or other glycoside conjugate, or may be an amino acid ester derivative.

Compositions

One aspect of the present invention pertains to a composition (e.g., a pharmaceutical composition) comprising a PPDA compound, as described herein, and a pharmaceutically acceptable carrier, diluent, or excipient.

Another aspect of the present invention pertains to a method of preparing a composition (e.g., a pharmaceutical composition) comprising mixing a PPDA compound, as described herein, and a pharmaceutically acceptable carrier, diluent, or excipient.

Uses

The PPDA compounds described herein are useful in the treatment of, for example, proliferative disorders (as "antiproliferative agents"), cancer (as "anti-cancer agents"), viral infections (as "anti-viral agents"), neurodegenerative diseases (as "anti-neurodegenerative agents"), etc.

Use in Methods of Inhibiting CDK

One aspect of the present invention pertains to a method of inhibiting CDK (e.g., CDK1, CDK2, CDK4, CDK5, CDK6, CDK7, CDK8, CDK9, CDK10, CDK11, CDK12, CDK13, etc.) function (e.g., in a cell), in vitro or in vivo, comprising contacting the cell with an effective amount of a PPDA compound, as described herein.

One of ordinary skill in the art is readily able to determine whether or not a candidate compound inhibits CDK (e.g., CDK1, CDK2, CDK4, CDK5, CDK6, CDK7, CDK8, CDK9, CDK10, CDK11, CDK12, CDK13, etc.). For example, suitable assays are described herein or are known in the art.

In one embodiment, the method is performed in vitro.

In one embodiment, the method is performed in vivo.

In one embodiment, the PPDA compound is provided in the form of a pharmaceutically acceptable composition.

Any type of cell may be treated, including adipose, lung, gastrointestinal (including, e.g., bowel, colon), breast (mammary), ovarian, prostate, liver (hepatic), kidney (renal), bladder, pancreas, brain, and skin.

For example, a sample of cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Inhibiting Cell Proliferation, etc.

The PPDA compounds described herein, e.g., (a) regulate (e.g., inhibit) cell proliferation;

(b) inhibit cell cycle progression; (c) promote apoptosis; or (d) a combination of one or more of these.

One aspect of the present invention pertains to a method of regulating (e.g., inhibiting) cell proliferation (e.g., proliferation of a cell), inhibiting cell cycle progression, promoting apoptosis, or a combination of one or more these, in vitro or in vivo, comprising contacting a cell with an effective amount of a PPDA compound, as described herein.

In one embodiment, the method is a method of regulating (e.g., inhibiting) cell proliferation (e.g., proliferation of a cell), in vitro or in vivo, comprising contacting a cell with an effective amount of a PPDA compound, as described herein.

In one embodiment, the method is performed in vitro.

In one embodiment, the method is performed in vivo.

In one embodiment, the PPDA compound is provided in the form of a pharmaceutically acceptable composition.

Any type of cell may be treated, including lung, gastrointestinal (including, e.g., bowel, colon), breast (mammary), ovarian, prostate, liver (hepatic), kidney (renal), bladder, pancreas, brain, and skin.

One of ordinary skill in the art is readily able to determine whether or not a candidate compound regulates (e.g., inhibits) cell proliferation, etc. For example, assays, which may conveniently be used to assess the activity offered by a particular compound are described herein.

For example, a sample of cells (e.g., from a tumour) may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to a PPDA compound, as described herein, for use in a method of treatment of the human or animal body by therapy, for example, for use a method of treatment of a disorder (e.g., a disease) as described herein.

Use in the Manufacture of Medicaments

Another aspect of the present invention pertains to use of a PPDA compound, as described herein, in the manufacture of a medicament, for example, for use in a method of treatment, for example, for use a method of treatment of a disorder (e.g., a disease) as described herein.

In one embodiment, the medicament comprises the PPDA compound.

Methods of Treatment

Another aspect of the present invention pertains to a method of treatment, for example, a method of treatment of a disorder (e.g., a disease) as described herein, comprising administering to a subject in need of treatment a therapeutically-effective amount of a PPDA compound, as described herein, preferably in the form of a pharmaceutical composition.

Disorders Treated

In one embodiment (e.g., for use in methods of therapy, of use in the manufacture of medicaments, of methods of treatment), the treatment is treatment of: a disorder (e.g., a disease) that is associated with CDK; a disorder (e.g., a disease) resulting from an inappropriate activity of a CDK; a disorder (e.g., a disease) that is associated with CDK mutation; a disorder (e.g., a disease) that is associated with CDK overexpression; a disorder (e.g., a disease) that is associated with upstream pathway activation of CDK; a disorder (e.g., a disease) that is ameliorated by the inhibition (e.g., selective inhibition) of CDK.

In one embodiment (e.g., for use in methods of therapy, of use in the manufacture of medicaments, of methods of treatment), the treatment is treatment of: a proliferative disorder; cancer; a viral infection (e.g., HIV); a neurodegenerative disorder (e.g., Alzheimer's disease, Parkinson's disease); ischaemia; a renal disease; or a cardiovascular disorder (e.g., atherosclerosis).

Disorders Treated—Disorders Associated with CDK

In one embodiment (e.g., for use in methods of therapy, of use in the manufacture of medicaments, of methods of treatment), the treatment is treatment of a disorder (e.g., a disease) that is associated with CDK (e.g., CDK1, CDK2, CDK4, CDK5, CDK6, CDK7, CDK8, CDK9, CDK10, CDK11, CDK12, CDK13, etc.).

In one embodiment, the treatment is treatment of: a disorder (e.g., a disease) resulting from an inappropriate activity of a CDK (e.g., CDK1, CDK2, CDK4, CDK5, CDK6, CDK7, CDK8, CDK9, CDK10, CDK11, CDK12, CDK13, etc.).

In one embodiment, the treatment is treatment of: a disorder (e.g., a disease) that is associated with CDK mutation; CDK overexpression (e.g., as compared to corresponding normal cells; e.g., wherein the overexpression is by a factor of 1.5, 2, 3, 5, 10, 20 or 50); or upstream pathway activation of CDK.

In one embodiment, the treatment is treatment of a disorder (e.g., a disease) that is ameliorated by the inhibition (e.g., selective inhibition) of CDK (e.g., CDK1, CDK2, CDK4, CDK5, CDK6, CDK7, CDK8, CDK9, CDK10, CDK11, CDK12, CDK13, etc.).

Disorders Treated—Proliferative Disorders

In one embodiment (e.g., for use in methods of therapy, of use in the manufacture of medicaments, of methods of treatment), the treatment is treatment of a proliferative disorder.

The term "proliferative disorder," as used herein, pertains to an unwanted or uncontrolled cellular proliferation of excessive or abnormal cells which is undesired, such as neoplastic or hyperplastic growth.

In one embodiment, the treatment is treatment of: a proliferative disorder characterised by benign, pre-malignant, or malignant cellular proliferation.

In one embodiment, the treatment is treatment of: hyperplasia; a neoplasm; a tumour (e.g., a histocytoma, a glioma, an astrocyoma, an osteoma); cancer; psoriasis; a bone disease; a fibroproliferative disorder (e.g., of connective tissues); pulmonary fibrosis;

atherosclerosis; or smooth muscle cell proliferation in the blood vessels (e.g., stenosis or restenosis following angioplasty).

Disorders Treated—Cancer

In one embodiment (e.g., of use in methods of therapy, of use in the manufacture of medicaments, of methods of treatment), the treatment is treatment of cancer.

In one embodiment, the treatment is treatment of cancer metastasis.

Included among cancers are:

(1) Carcinomas, including tumours derived from stratified squamous epithelia (squamous cell carcinomas) and tumours arising within organs or glands (adenocarcinomas). Examples include breast, colon, lung, prostate, ovary.

(2) Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and haemangioendothelioma (blood vessels); liposarcoma (adipose tissue); glioma and astrocytoma (neurogenic connective tissue found in the brain); myxosarcoma (primitive embryonic connective tissue); mesenchymous and mixed mesodermal tumour (mixed connective tissue types).

(3) Myeloma.

(4) Haematopoietic tumours, including: myelogenous and granulocytic leukaemia (malignancy of the myeloid and granulocytic white blood cell series); lymphatic, lymphocytic, and lymphoblastic leukaemia (malignancy of the lymphoid and lymphocytic blood cell series); polycythaemia vera (malignancy of various blood cell products, but with red cells predominating).

(5) Lymphomas, including: Hodgkin and Non-Hodgkin lymphomas.

(6) Mixed Types, including, e.g., adenosquamous carcinoma; mixed mesodermal tumour; carcinosarcoma; teratocarcinoma.

For example, in one embodiment, the treatment is treatment of breast cancer.

In one embodiment, the cancer is characterised by, or further characterised by, cancer stem cells.

In one embodiment, the cancer is associated with CDK (e.g., CDK1, CDK2, CDK4, CDK5, CDK6, CDK7, CDK8, CDK9, CDK10, CDK11, CDK12, CDK13, etc.), especially CDK7.

In one embodiment, the cancer is characterised by, or further characterised by, inappropriate activity of CDK (e.g., CDK1, CDK2, CDK4, CDK5, CDK6, CDK7, CDK8, CDK9, CDK10, CDK11, CDK12, CDK13, etc.), especially CDK7.

In one embodiment, the cancer is characterised by, or further characterised by, overexpression of CDK (e.g., CDK1, CDK2, CDK4, CDK5, CDK6, CDK7, CDK8, CDK9, CDK10, CDK11, CDK12, CDK13, etc.), especially CDK7.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of cell migration (the spread of cancer cells to other parts of the body), the inhibition of invasion (the spread of tumour cells into neighbouring normal structures), the promotion of apoptosis (programmed cell death), death by necrosis, or induction of death by autophagy. The compounds described herein may be used in the treatment of the cancers described herein, independent of the mechanisms discussed herein.

Disorders Treated—Viral Infection

In one embodiment (e.g., for use in methods of therapy, of use in the manufacture of medicaments, of methods of treatment), the treatment is treatment of a viral infection.

In one embodiment, the treatment is treatment of a viral infection by:
(Group I:) a dsDNA virus, e.g., an adenovirus, a herpesvirus, a poxvirus;
(Group II:) a ssDNA virus, e.g., a parvovirus;
(Group III:) a dsRNA virus, e.g., a reovirus;
(Group IV:) a (+)ssRNA virus, e.g., a picornavirus, a togavirus;
(Group V:) a (−)ssRNA virus, e.g., an orthomyxovirus, a rhabdovirus;
(Group VI:) a ssRNA-RT virus, e.g., a retrovirus; or
(Group VII:) a dsDNA-RT virus, e.g., a hepadnavirus.

As used above: ds: double strand; ss: +strand; (+)ssRNA: +strand RNA; (−)ssRNA: -strand RNA; ssRNA-RT: (+strand)RNA with DNA intermediate in life-cycle.

In one embodiment, the treatment is treatment of: human immunodeficiency virus (HIV); hepatitis B virus (HBV); hepatitis C virus (HCV); human papilloma virus (HPV); cytomegalovirus (CMV); or Epstein-Barr virus (EBV); human herpesvirus 8 (HHV) associated with Kaposi sarcoma; Coxsackievirus B3; Borna virus; influenza virus.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment includes the prophylaxis of cancer, reducing the incidence of cancer, alleviating the symptoms of cancer, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents. Examples of treatments and therapies include chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more (e.g., 1, 2, 3, 4, etc.) additional therapeutic agents, as described below.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Examples of additional agents/therapies that may be co-administered/combined with treatment with the PPDA compounds described herein include the following:

an aromatase inhibitor, for example, exemestane (also known as Aromasin), letrozole (also known as Femara), anastrozole (also known as Arimidex), etc.;

an anti-estrogen, for example, faslodex (also known as Fulvestrant and 101182780), tamoxifen (also known as Nolvadex), hydroxytamoxifen, etc.;

a Her2 blocker, for example, herceptin, pertuzumab, lapatinib, etc.;

a cytotoxic chemotherapeutic agent, for example, a taxane (e.g., paclitaxel also known as Taxol; docetaxel also known as Taxotere), cyclophosphamide, an antimetabolite (e.g., carboplatin, capecitabine, gemcitabine, doxorubicin, epirubicin, 5-fluorouracil, etc.), etc.

Thus, in one embodiment, the treatment further comprises treatment (e.g., simultaneous or sequential treatment) with a further active agent which is, e.g., an aromatase inhibitor, an anti-estrogen, a Her2 blocker, a cytotoxic chemotherapeutic agent, etc.

Combination Therapy with an Aromatase Inhibitor and/or an Anti-Estrogen

Estrogen receptor α (ERα) is expressed in 70% of breast tumours and is recognised as the major driver of breast cancer development and progression in these cases. Consequently, ERα is the predominant target for adjuvant therapies in ERα-positive breast cancer. Inhibition of its activity with anti-estrogens and by inhibition of estrogen biosynthesis (e.g., using aromatase inhibitors), reduces relapse and improves patient survival (see, e.g., Osborne, 1998; Cuzick et al., 2010). Tamoxifen (Nolvadex) is an anti-estrogen that acts by competing with estrogen for binding to the estrogen receptor, to inhibit ERα activity. Importantly, many patients with ERα-positive breast cancer relapse on these hormonal therapies, resistant tumours mostly remaining ERα-positive (see, e.g., Ali et al., 2002; Johnston et al., 2003; Ali et al, 2011; Osborne et al., 2011).

Tamoxifen is an exemplifier of the class of anti-estrogen known as selective estrogen receptor modulators (SERMs), which are anti-estrogenic in the breast, but often have estrogen-like activities in other tissues, such as the cardiovascular system, and bone. Tamoxifen has been used widely as first line adjuvant agent for the treatment of ERα-positive breast cancer in pre- and post-menopausal women. Fulvestrant (Faslodex) is an anti-estrogen that competes with estrogen for binding to ERα to prevent its activation, but also promotes down-regulation of the ERα protein. As such, fulvestrant is an exemplifier of the class of anti-estrogens known as selective estrogen recepto downregulators (SERD). Fulvestrant is primarily used in the treatment of ERα-positive breast cancer patients who experience recurrence following treatment with first-line adjuvant agents such as tamoxifen.

Aromatase is a cytochrome P450 enzyme that catalyses the limiting step in conversion of androgens to estrogens. Clinically, anastrozole (Arimidex) and letrozole (Femara) are competitive inhibitors of the aromatase complex, whilst exemestane (Aromasin) is an irreversible inhibitor of aromatase. Aromatse inhibitors act by inhibiting estrogan biosynthesis and thereby levels of circulating estrogens and consequently by limiting estrogen availability they prevent ERα activation.

Estrogen binding to ERα protein occurs in the ligand (hormone) binding domain (LBD), which is C-terminal to the DNA binding domain (DBD), to promote ERα dimerisation, nuclear localisation and binding to DNA in regulatory regions of target genes, to regulate the expression of said target genes. Phosphorylation of ERα provides a key mechanism for regulating ERα activity, including DNA binding and transcription activation. In particular, ERα phosphorylation at serine-118 in a region N-terminal to the DBD that is important for transcription activation by ERα (known as transcription activation function 1 (AF-1), is one of the earlies events in ERα activation. Serine-118 phophorylation is mediated by estrogen stimulated recruitment of the transcription factor complex, TFIIH, which includes CDK7. Estrogen-stimulated TFIIH recruitment to the estrogen-bound LBD allows CDK7-mediated phosphorylation of serine-118, to promote ERα activity. CDK7 over-expression can promote ERα activity under conditions of low estrogen levels, as engendered by aromatse inhibitors, and lead to activation of the tamoxifen-bound ERα (see, e.g., Ali et al., 1993; Chen et al., 2000; Chen et al., 2002).

These findings provide the basis for the use of a PPDA compound, as described herein, in combination with an aromatase inhibitor or an anti-estrogen, for the treatment of breast cancer patients. Such a combination therapy would be especially useful in the treatment of breast cancer patients following emergence of resistance to the aromatase inhibitor or anti-estrogen. Such a combination therapy would also permit the use of reduced amounts and/or concentrations of the PPDA compound, the anti-estrogen, and/or the aromatase inhibitor, in order to reduce toxicity.

Studies demonstrating the synergistic effects of the combination of a particular PPDA compound (PPDA-001, also referred to herein as ICEC0942) with an anti-estrogen (4-hydroxytamoxifen or Faslodex) in the estrogen-responsive ERα-positive MCF-7 breast cancer cell line are described below. The agents acts co-operatively to inhibit the growth of breast cancer cells.

MCF-7 cells purchased from ATCC (USA) were routinely passaged in DMEM, supplemented with 10% fetal calf serum (FCS) and kept in a 37° C. incubator with 5% CO2.

The growth assay for both cell lines was performed in the appropriate media using the exact same protocol as described here. For the growth assay, 5000 cells were seeded into each well of 96-well plates in DMEM containing 10% FCS. MCF-7 cells were grown over a 12-day period in the presence of PPDA-001/ICEC0942 (100 nmol/L) and 4-hydroxytamoxifen (1 nmol/L) or Faslodex (1 nmol/L). Vehicle refers to the addition of an equal volume of the solvent (ethanol) in which 4-hydroxytamoxifen (100 nmol/L) and Faslodex (100 nmol/L) were prepared. 4-hydroxytamoxifen and Faslodex were prepared at a concentration of 100 µmol/L in ethanol, and so were diluted in culture medium at 1 µL per 1 mL of medium (1:1000 dilution), to give a final concentration of 100 nmol/L. At each time point, plates were removed for an SRB assay. For this assay, cells were fixed by the addition of 100 µL/well of ice-cold 40% trichloroacetic acid (TCA). The plates were left for 1 hour at 4° C., washed in water, and then 100 µL of 0.4% (w/v) sulforhodamine (SRB; Sigma-Aldrich, UK) prepared in 1% acetic acid was added. Plates were washed in 1% acetic acid to remove excess SRB reagent, air dried, and bound dye was solubilized by the addition of 100 µL of 10 mM tris base. The plates were read at 492 nm using a plate reader. Relative growth was plotted relative to the OD492 reading for cells at treatment time t=0 (n=5).

Figure 4:
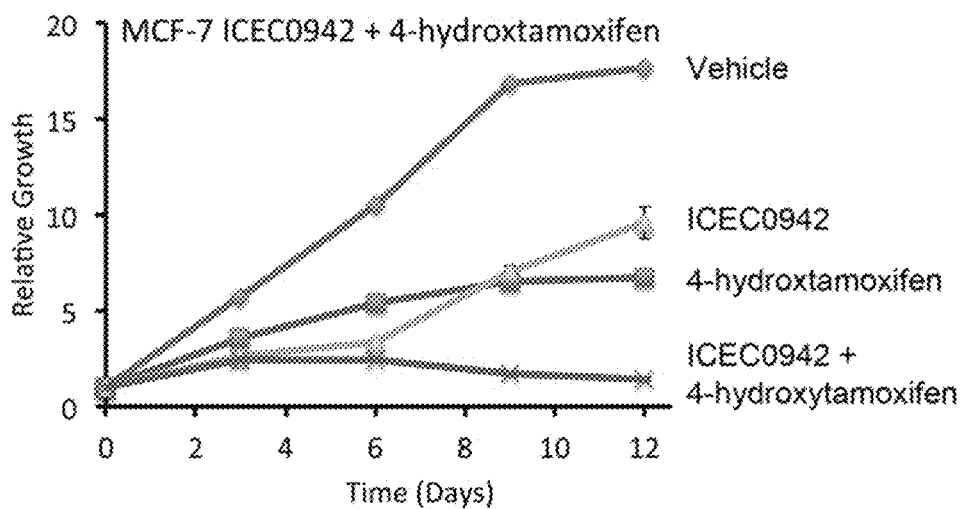
FIG. 4, which is a graph of relative growth (mean growth ±standard errors of the mean) as function of time for treatment with: (a) vehicle; (b) PPDA-001/ICEC0942; (c) 4-hydroxytamoxifen; and (d) PPDA-001/ICEC0942 with 4-hydroxytamoxifen. As shown, co-treatment greatly enhances the growth inhibition observed for each drug alone.

The results for 4-hydroxytamoxifen are illustrated in FIG. 4, which is a graph of relative growth (mean growth ±standard errors of the mean) as function of time for treatment with: (a) vehicle; (b) PPDA-001/ICEC0942; (c) 4-hydroxytamoxifen; and (d) PPDA-001/ICEC0942 with 4-hydroxytamoxifen. As shown, co-treatment greatly enhances the growth inhibition observed for each drug alone.

Figure 5:
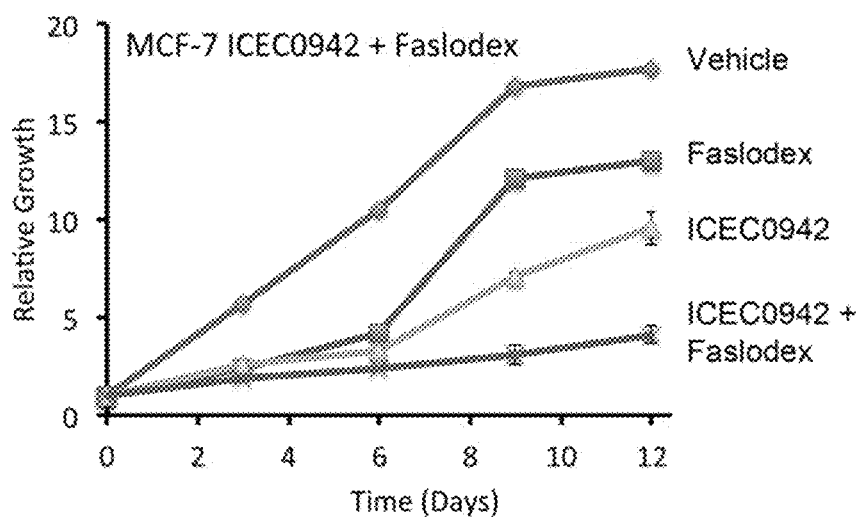
FIG. 5, which is a graph of relative growth (mean growth ±standard errors of the mean) as function of time for treatment with: (a) vehicle; (b) PPDA-001/ICEC0942; (c) Faslodex; and (d) PPDA-001/ICEC0942 with Faslodex. As shown, co-treatment greatly enhances the growth inhibition observed for each drug alone.

The results for Faslodex are illustrated in FIG. 5, which is a graph of relative growth (mean growth ±standard errors of the mean) as function of time for treatment with: (a) vehicle; (b) PPDA-001/ICEC0942; (c) Faslodex; and (d) PPDA-001/ICEC0942 with Faslodex. As shown, co-treatment greatly enhances the growth inhibition observed for each drug alone.

MCF-7 cells cultured in DMEM supplemented with 10% FCS were treated with 1 µmol/L PPDA-001/ICEC0942 for the time period shown. As PPDA-001/ICEC0942 was solubilized in DMSO, an equal volume of DMSO was added as a control. Cell lysates were prepared by the addition of RIPA buffer (Sigma-Aldrich, cat no: R0278). Immunoblotting was carried out using standard methods (see, e.g., Harlow & Lane, 1988, Antibodies: A Laboratory Manual, Cold Spring Harbor Laboratory Press, USA), with antibodies for the protein or phosphorylation mark indicated. β-actin was used as control for protein loading. The various primary antibodies and their dilutions are shown in the following table. The second antibody was HRP-coupled Goat anti Mouse or Rabbit IgG.

| Antibody | Company / Catalog Number | 1° Antibody Dilution | 2° Antibody Dilution |
| --- | --- | --- | --- |
| ERα (6F11) | Vector Laboratories (VP-E613) | 1:1000 | 1:2500 |
| ERα (phospho-Ser118) | Santa Cruz (SC-101675) | 1:500 | 1:2500 |
| RNA Poll II (phospho-Ser2) | Abcam (Ab5095) | 1:500 | 1:2500 |
| RNA Poll II (phospho-Ser5) | Abcam (Ab5131) | 1:500 | 1:2500 |
| RNA Poll II | Abcam (Ab5408) | 1:500 | 1:2500 |
| CDK2 (phospho-T160) | Abanova (PAB0438) | 1:500 | 1:2500 |
| CDK2 | Cell Signaling (2546) | 1:500 | 1:2500 |
| CDK1 (phospho-T161) | Cell Signaling (9114) | 1:500 | 1:2500 |

-continued

| Antibody | Company / Catalog Number | 1° Antibody Dilution | 2° Antibody Dilution |
|---|---|---|---|
| CDK1 | Cell Signaling (9112) | 1:500 | 1:2500 |
| β-Actin | Abcam (Ab2380) | 1:500 | 1:2500 |

Figure 6:
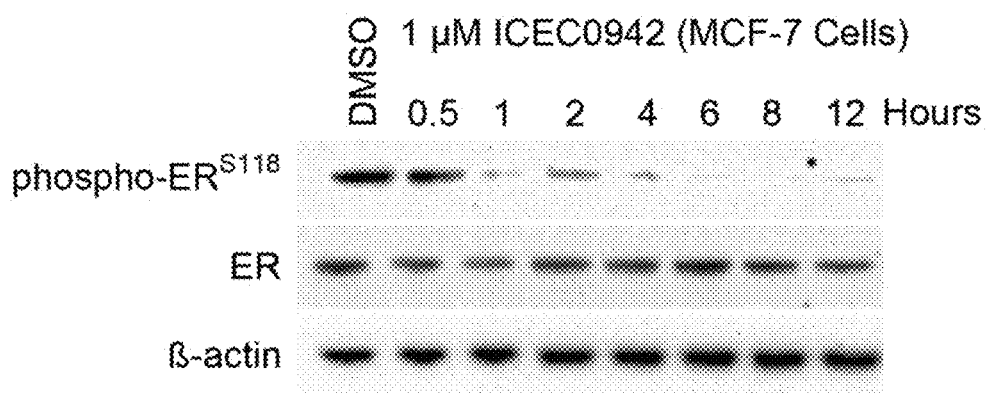
FIG. 6 shows immunoblot gels for the bands for phospho-$ER^{S118}$, ER, and β-actin, as a function of time, for cell lysates from MCF-7 cells treated with 1 μmol/L PPDA-001/ICEC0942. As shown in the figure, PPDA-001/ICEC0942 inhibits phosphorylation of ER at serine-118 (phospho-$ER^{S118}$).

FIG. 6 shows immunoblot gels for the bands for phospho-$ER^{S118}$, ER, and β-actin, as a function of time, for cell lysates from MCF-7 cells treated with 1 μmol/L PPDA-001/ICEC0942. As shown in the figure, PPDA-001/ICEC0942 inhibits phosphorylation of ER at serine-118 (phospho-$ER^{S118}$).

Figure 7:
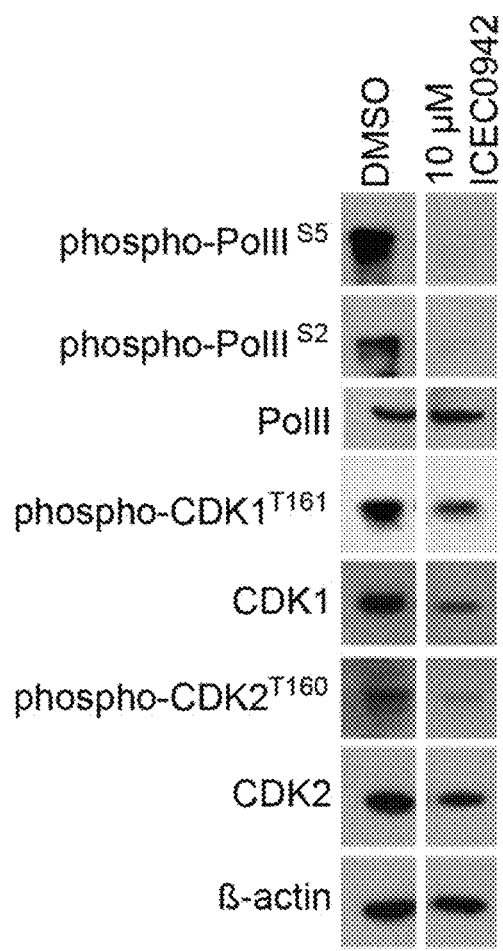
FIG. 7 shows immunoblot gels for cell lysates from MCF-7 cells treated for 24 hours with 10 μmol/L PPDA-001/ICEC0942.

FIG. 7 shows immunoblot gels for cell lysates from MCF-7 cells treated for 24 hours with 10 μmol/L PPDA-001/ICE00942.

Thus, in one embodiment, the treatment further comprises treatment (e.g., simultaneous or sequential treatment) with a further active agent which is an aromatase inhibitor, for example, exemestane (also known as Aromasin), letrozole (also known as Femara), or anastrozole (also known as Arimidex). In one embodiment, the disorder is breast cancer (e.g., breast cancer which is resistant to said aromatase inhibitor).

Also, in one embodiment, the treatment further comprises treatment (e.g., simultaneous or sequential treatment) with a further active agent which is an anti-estrogen, for example, faslodex (also known as Fulvestrant and 101182780), tamoxifen (also known as Nolvadex), or hydroxytamoxifen. In one embodiment, the disorder is breast cancer (e.g., breast cancer which is resistant to said anti-estrogen).

Other Uses

The PPDA compounds described herein may also be used as cell culture additives to inhibit CDK (e.g., CDK1, CDK2, CDK4, CDK5, CDK6, CDK7, CDK8, CDK9, CDK10, CDK11, CDK12, CDK13, etc.).

The PPDA compounds described herein may also be used as part of an in vitro assay, for example, in order to determine whether a candidate host is likely to benefit from treatment with the compound in question.

The PPDA compounds described herein may also be used as a standard, for example, in an assay, in order to identify other active compounds, other CDK (e.g., CDK1, CDK2, CDK4, CDK5, CDK6, CDK7, CDK8, CDK9, CDK10, CDK11, CDK12, CDK13, etc.) inhibitors, etc.

Kits

One aspect of the invention pertains to a kit comprising (a) a PPDA compound as described herein, or a composition comprising a PPDA compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The PPDA compound or pharmaceutical composition comprising the PPDA compound may be administered to a subject by any convenient route of administration, whether systemically/peripherally or topically (i.e., at the site of desired action).

Examples of routes of administration include oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for a PPDA compound to be administered alone, it is preferable to present it as a pharmaceutical formulation (e.g., composition, preparation, medicament) comprising at least one PPDA compound, as described herein, together with one or more other pharmaceutically acceptable ingredients well known to those skilled in the art, including pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising mixing at least one PPDA compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier, which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or mixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection) include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes, which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the PPDA compounds, and compositions comprising the PPDA compounds, can vary from patient to patient. Determining the optimal dosage will generally involve the balancing of the level of therapeutic benefit against any risk or deleterious side effects. The selected dosage level will depend on a variety of factors including the activity of the particular PPDA compound, the route of administration, the time of administration, the rate of excretion of the PPDA compound, the duration of the treatment, other drugs, compounds, and/or materials used in combination, the severity of the disorder, and the species, sex, age, weight, condition, general health, and prior medical history of the patient. The amount of PPDA compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the PPDA compound is in the range of about 10 µg to about 250 mg (more typically about 100 µg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

Chemical Syntheses

Melting points were determined using a Reichert-Thermovar hot-stage apparatus and are uncorrected. IR spectra were recorded as thin films with the absorption bands reported in wave number ($cm^{-1}$).

$^1$H NMR spectra were recorded at 400 MHz or at 500 MHz. Chemical shifts are reported as δ-values in ppm relative to the $CDCl_3$ peak (δH 7.26), to the $CD_3OD$ peak (δH 3.31), and to the $DMSO-d_6$ peak (δH 2.54). Coupling constants (J) recorded in Hertz (Hz) and quoted to the nearest 0.5 Hz.

Optical Rotations were recorded with a path length of 1 dm, using the 589.3 mn D-line of sodium. Concentrations (c) are quoted in g/100 mL.

All reactions were carried out with magnetic stirring and if air or moisture sensitive, in flame-dried or oven-dried glassware under nitrogen or argon. Syringes, used to transfer reagents and solvents, were purged with nitrogen or argon prior to use. Reaction temperatures other than room temperature were recorded as the bath temperature unless otherwise stated.

All solvents and reagents were used as commercially supplied, unless otherwise stated. $Et_2O$, THF, PhMe and $CH_2Cl_2$ were redistilled from $Na-Ph_2CO$, $Na-Ph_2CO$, Na and $CaH_2$ respectively.

Thin layer chromatography was performed on pre-coated aluminum backed silica gel F254 glass plates. The chromatogram was visualized under UV light and/or by staining using aqueous potassium permanganate or aqueous acidic vanillin followed by heating with a heat gun.

Flash column chromatography was performed using silica gel, particle size 40-63 µm (eluents are given in parenthesis).

General Synthesis

The general synthetic route towards the target compounds is illustrated in the following scheme. The three main side chains ($R^1$, $R^2$ and $R^3$) can be greatly varied.

2- Synthesis of the Aromatic Cores

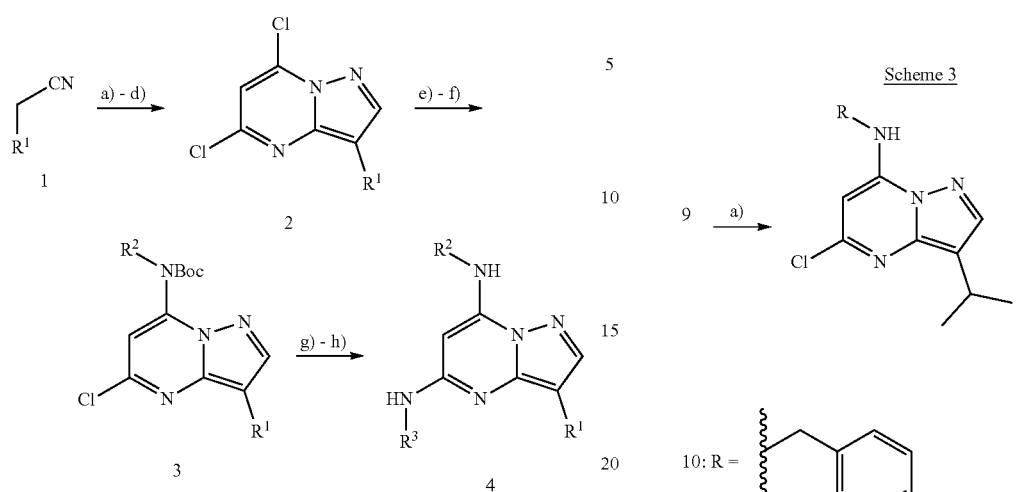

a) HCO₂Et, LiN(iso-Pr)₂, -78° C. to room temperature.
b) N₂H₄•H₂O, acetic acid, EtOH.
c) Na, EtOH, diethyl malonate, reflux.
d) N,N-dimethylaniline, POCl₃, reflux.
e) R² —NH₂, Et₃N, EtOH, reflux.
f) Boc₂O, DMAP, Et₃N, THF, room temperature.
g) R³ —NH₂, Pd₂(dba)₃, rac-BINAP, NaO$^t$Bu, toluene, 95° C.
h) 5M HCl/MeOH.

1—Synthesis of the Aromatic Dichloro-Heterocyclic Compound 9

The synthesis of the dichloride 9 was carried out in a manner similar to published methods. See, e.g., Jogalekar et al., 2008.

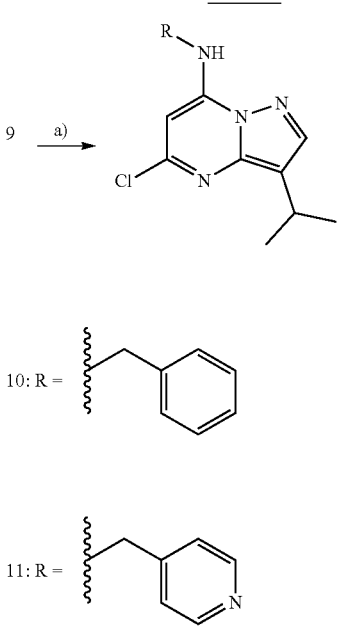

a) HCO₂Et, LiN(iso-Pr)₂, -78° C. to room temperature.
b) N₂H₄•H₂O, acetic acid, EtOH.
c) Na, EtOH, diethyl malonate, reflux, 35% (3 steps).
d) N,N-dimethylaniline, POCl₃, reflux, 81%.

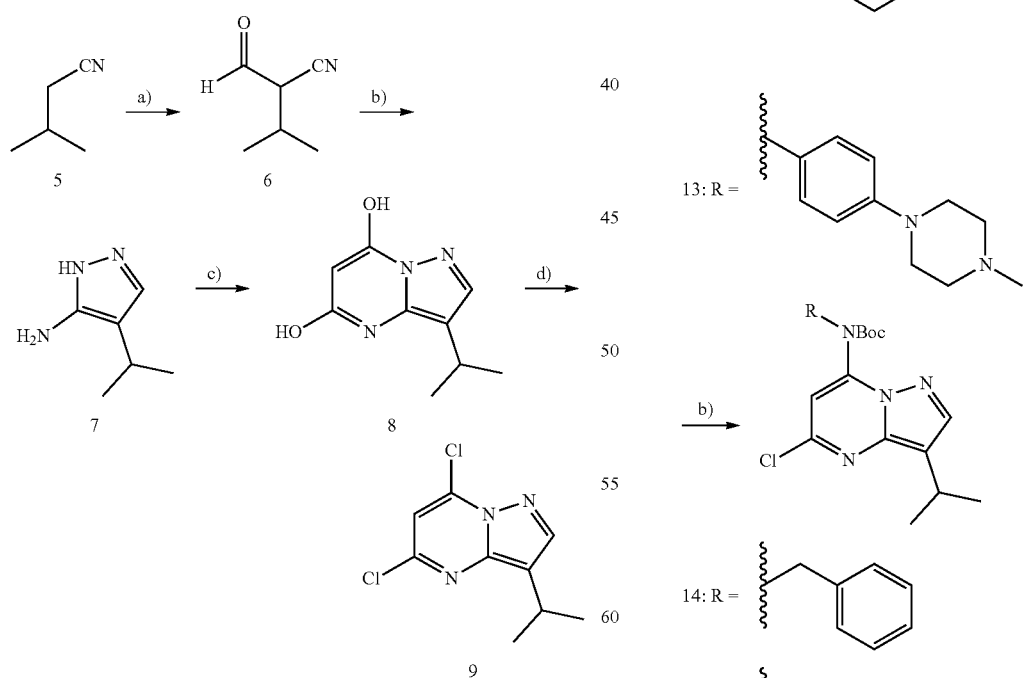

57

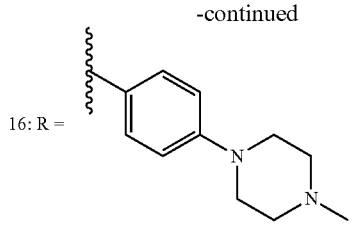

16: R = a)
10: benzylamine, EtOH, reflux, 97%.
11: 4-picolylamine, EtOH, reflux, 99%.
12: tert-butyl 4-carbamoylpiperidine-1-carboxylate, NaH, DMF, room temperature, 60%.
13: 4-(4-methylpiperazin-1-yl)aniline, NaH, DMF, 50 °C., 66%.
b)
14: Boc₂O, DMAP, THF, room temperature, 96%.
15: Boc₂O, DMAP, THF, room temperature, 92%.
16: Boc₂O, DMAP, 1,4-dioxane, 96%.

2.1—General Procedure A—Substitution of Chloride 9

A solution containing 3-iso-propyl-5,7-dichloropyrazolo[1,5-a]pyrimidine 9 (2.17 mmol) and the amine (4.56 mmol) in EtOH (20 mL) was heated at reflux for 3 h. The reaction mixture was cooled to room temperature and concentrated in vacuo. The remaining residue was purified by flash column chromatography (MeOH:EtOAc) to yield the desired product in analytically pure form.

2.2—Synthesis of the Aromatic Cores

Synthesis 1

N-Benzyl-5-chloro-3-iso-propylpyrazolo[1,5-a]pyrimidin-7-amine (10)

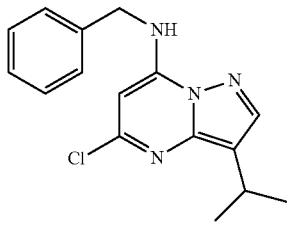 [SMILES: CC(C)c1cnn2c(NCc3ccccc3)cc(Cl)nc12]

Following general procedure A, 9 (500 mg, 2.17 mmol) and benzylamine (0.52 mL, 4.78 mmol) were allowed to react in EtOH (20 mL). The title compound was obtained as a white solid (630 mg, 97%) after flash column chromatography (hexane:EtOAc 6:1).

M.p.=74° C. (CHCl₃); $^1$H NMR (300 MHz, CDCl₃) δ 7.82 (m, 1H), 7.32 (m, 5H), 7.01 (m, 1H), 5.90 (m, 1H), 4.53 (m, 2H), 3.27 (sept, J=6.9 Hz, 1H), 1.32 (d, J=6.9 Hz, 6H); $^{13}$C (CDCl₃, 300 MHz) δ 150.1, 146.8, 144.1, 141.5, 135.7, 129.0, 128.1, 127.1, 116.9, 84.6, 46.0, 23.4, 23.3; HRMS (CI) calc. for $C_{16}H_{17}ClN_4$ (M+H$^+$): 301.1220, found: 301.1230; Anal. calc. for $C^{16}H_{17}ClN_4$: C, 63.89, H, 5.70, N, 18.63, found: C, 63.95, H, 5.78, N, 18.59.

58

Synthesis 2

5-Chloro-3-iso-propyl-N-(pyridin-4-ylmethyl) pyrazolo[1,5-a]pyrimidin-7-amine (11)

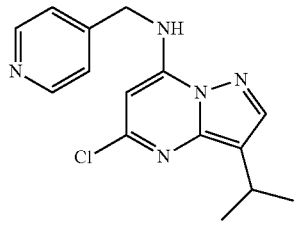 [SMILES: CC(C)c1cnn2c(NCc3ccncc3)cc(Cl)nc12]

Following general procedure A, 9 (460 mg, 2.0 mmol) and 4-picolylamine (0.407 mL, 4.0 mmol) were allowed to react in EtOH (4 mL). The title compound was obtained as a pale yellow solid (601 mg, 99%) after flash column chromatography (hexane:EtOAc gradient 7:3 to 1:1).

$^{13}$C NMR (100 MHz, CDCl₃) δ 150.4, 150.0, 146.9, 145.3, 144.2, 141.8, 121.5, 117.2, 84.8, 44.8, 23.4; HRMS (ESI) calc. for $C_{15}H_{16}ClN_5$ (M+H$^+$): 302.1185, found: 302.1172.

Synthesis 3 tert-Butyl 4-((5-chloro-3-iso-propylpyrazolo[1,5-a]pyrimidin-7-yl)carbamoyl)piperidine-1-carboxylate (12)

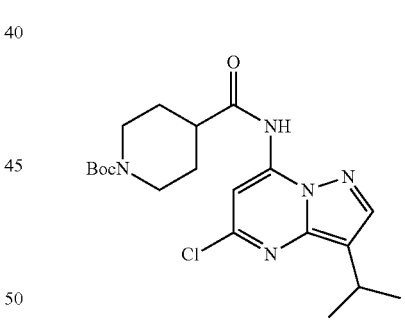

tert-Butyl-4-carbamoylpiperidine-1-carboxylate (1 g, 4.37 mmol) was dissolved in dry DMF (4 mL) and treated with NaH (60% wt., 175 mg, 4.37 mmol) at room temperature for 1 h. The mixture was treated with 9 (1.0 g, 4.37 mmol). The title compound was obtained as a white solid (1.1 g, 60%) after flash column chromatography (hexane:EtOAc 8:2).

IR (neat): $v_{max}$=3141, 1705, 1541; $^1$H NMR (400 MHz, CDCl₃) δ 9.31 (s, 1H), 7.80 (s, 1H), 7.57 (s, 1H), 4.28-4.07 (m, 2H), 3.26-3.11 (m, 1H), 2.79 (br. s., 2H), 2.70-2.59 (m, 1H), 1.92 (d, J=11.2 Hz, 2H), 1.76-1.64 (m, 2H), 1.40 (s, 9H), 1.26 (d, J=6.8 Hz, 6H); $^{13}$C NMR (101 MHz, CDCl₃) δ=173.1, 170.9, 154.4, 150.1, 143.5, 141.4, 139.5, 118.0, 94.5, 79.7, 60.1, 43.9, 42.6, 28.2, 28.0, 23.3, 23.1.

Synthesis 4

5-Chloro-3-iso-propyl-N-(4-(4-methylpiperazin-1-yl)phenyl)pyrazolo[1,5-a]pyrimidin-7-amine (13)

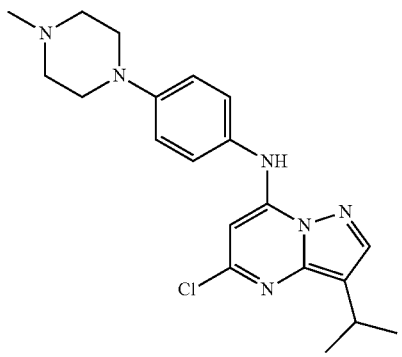 [SMILES: CC(C)c1cnn2c(Nc3ccc(N4CCN(C)CC4)cc3)cc(Cl)nc12]

NaH (60% wt., 125 mg, 3.14 mmol) was added with stirring to a solution of 4-(4-methylpiperazin-1-yl)aniline (see, e.g., Sengupta et al., 2012) (60 g, 3.14 mmol) in THF (15 mL). After 10 min, a solution of 9 (0.72 g, 3.14 mmol) in DMF (2 mL) was added and the mixture was heated to 50° C. for 3 h. The title compound was obtained as a white solid (80 mg, 66%) after flash column chromatography (CH$_2$Cl$_2$/MeOH 9:1).

$R_f$=0.36 (9:1 CH$_2$Cl$_2$/MeOH); IR (neat): $v_{max}$=3324, 1609, 1577 cm$^{-1}$; $^1$H NMR (CDCl$_3$, 400 MHz) δ 7.97 (s, 1H), 7.90 (s, 1H), 7.26-7.22 (m, 2H), 7.02-6.98 (m, 2H), 6.07 (s, 1H), 3.33 (sept, J=6.7 Hz, 1H), 3.28 (dd, J=6.3, 3.9 Hz, 4H), 2.62 (dd, J=6.3, 3.9 Hz, 4H), 2.39 (s, 3H), 1.35 (d, J=6.9 Hz, 6H); HRMS (ESI) Calcd. for C$_{20}$H$_{25}$N$_6$Cl [M+H]+, 385.1907, found 385.1909.

2.3—General Procedure B—Boc Protection

Boc$_2$O (0.73 mmol) was added with stirring to a solution of the amino-heterocycle (0.52 mmol) and 4-dimethylaminopyridine (DMAP) (0.31 mmol) in dry THF (2 mL) at 0° C. After 16 h at room temperature, the reaction mixture was diluted with EtOAc, washed with water twice and saturated aqueous NaHCO$_3$, dried over MgSO$_4$, filtered and concentrated under reduced pressure. Purification by flash column chromatography (hexane:Et$_2$O) afforded the desired product in analytically pure form.

2.4—Synthesis of the Boc-Protected Aromatic Cores

Synthesis 5 tert-Butyl benzyl(5-chloro-3-iso-propyl pyrazolo[1,5-a]pyrimidin-7-yl)carbamate (14)

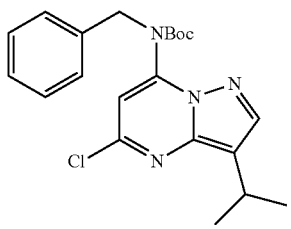 [SMILES: CC(C)c1cnn2c(N(Cc3ccccc3)C(=O)OC(C)(C)C)cc(Cl)nc12]

Following general procedure B, 10 (300 mg, 1 mmol), Boc$_2$O (284 mg, 1.3 mmol) and DMAP (24 mg, 0.2 mmol) were allowed to react in THF (6 mL). The title compound was obtained as a pale yellow solid (385 mg, 96%) after flash column chromatography (hexane:EtOAc 20:1).

M.p.=93-94° C. (EtOAc); IR (neat): $v_{max}$=1727, 1612, 1518, 1454, 1154, 699 cm$^{-1}$; $^{13}$C NMR (300 MHz, CDCl$_3$) δ 152.6, 147.9, 144.9, 144.0, 142.5, 136.7, 128.5, 127.7, 127.6, 118.2, 106.1, 82.9, 51.3, 27.8, 23.5, 23.3; HRMS (CI) calc. for C$_{21}$H$_{25}$ClN$_4$O$_2$ (M+H$^+$): 401.1744, found: 401.1747; Anal. calc. for C$_{21}$H$_{25}$ClN$_4$O$_2$: C, 62.91, H, 6.29, N, 13.98, found: C, 62.87, H, 6.19, N, 13.94.

Synthesis 6 tert-Butyl (5-chloro-3-iso-propylpyrazolo[1,5-a]pyrimidin-7-yl)(pyridin-4-ylmethyl) carbamate (15)

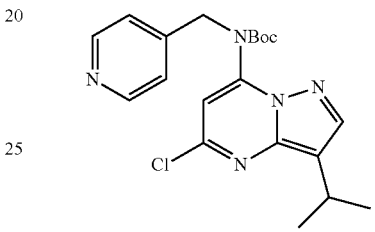

Following general procedure B, 11 (560 mg, 1.85 mmol), Boc$_2$O (565 mg, 2.59 mmol) and DMAP (67 mg, 0.55 mmol) were allowed to react in THF (10 mL). The title compound was obtained as a pale yellow solid (688 mg, 92%) after flash column chromatography (hexane:EtOAc 4:1).

IR (neat): $v_{max}$=1724, 1610, 1560, 1516, 1367, 1305, 1150, 1103, 877, 730 cm$^{-1}$; $^1$H NMR (400 MHz, CDCl$_3$) δ 8.51 (d, J=5.0 Hz, 2H), 7.97 (s, 1H), 7.20 (d, J=5.0 Hz, 2H), 6.57 (s, 1H), 4.98 (s, 2H), 3.25 (sept, J=6.9 Hz, 1H), 1.32 (s, 9H), 1.30 (d, J=6.9 Hz, 6H); $^{13}$C NMR (100 MHz, CDCl$_3$) δ 152.2, 149.8, 147.7, 145.8, 144.9, 143.8, 142.5, 121.9, 118.2, 105.3, 83.2, 50.6, 27.6, 23.4, 23.1; HRMS (ESI) calc. for C$_{20}$H$_{24}$ClN$_5$O$_2$ (M+H$^+$): 402.1698, found: 402.1697.

Synthesis 7 tert-Butyl 5-chloro-3-iso-propylpyrazolo[1,5-a]pyrimidin-7-yl(4-(4-methylpiperazin-1-yl)phenyl)carbamate (16)

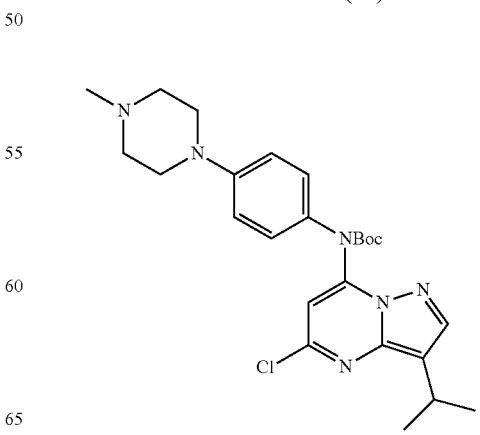

Following general procedure B, 13 (0.67 g, 1.74 mmol), Boc$_2$O (0.76 g, 3.48 mmol) and DMAP (21 mg, 0.174 mmol) were allowed to react in 1,4-dioxane (8 mL). The title compound was obtained as a pale yellow solid (806 mg, 96%) after flash column chromatography (CH$_2$Cl$_2$:MeOH 20:1).

R$_f$=0.50 (9:1 CH$_2$Cl$_2$/MeOH); IR (neat): ν$_{max}$=1735, 1608, 1511, 1147 cm$^{-1}$; $^{13}$C NMR (CDCl$_3$, 100 MHz) δ 152.1, 150.7, 148.1, 145.3, 145.1, 142.8, 131.4, 127.6, 118.2, 116.1, 105.5, 83.1, 55.0, 48.7, 46.2, 27.9, 23.6, 23.5; HRMS (ESI) Calcd. for C$_{25}$H$_{33}$N$_6$O$_2$Cl [M+H]$^+$, 485.2432, found 485.2421.

3—Synthesis of the Pyrrolidine and Piperidine Intermediates 3.1—Synthesis of Pyrrolidine 22

Scheme 4

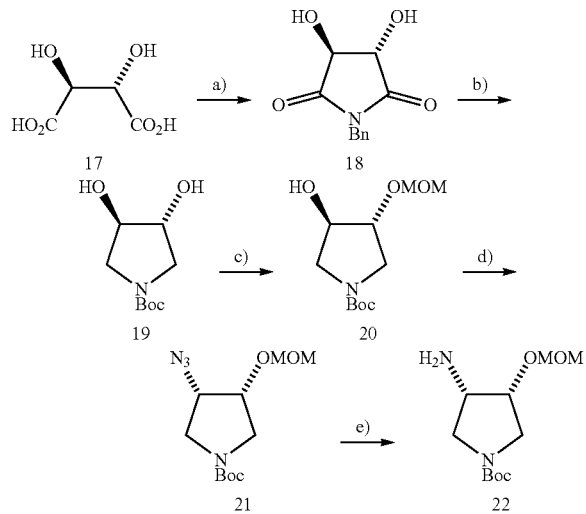

a) benzylamine, xylene, Dean-Stark, 160° C., 81%.
b) i) LiAlH$_4$, THF, 0° C. to reflux; ii) H$_2$, Pd/C, MeOH, Boc$_2$O, 72% (2 steps).
c) NaH, MOMCl, THF, 0° C. to room temperature, 75%.
d) i) MsCl, Et$_3$N, 0° C., ii) NaN$_3$, DMF, 100° C., 81% (2 steps).
e) H$_2$, Pd/C, MeOH, 98%.

Synthesis 8

(3S,4S)-1-Benzyl-3,4-dihydroxypyrrolidine-2,5-dione (18)

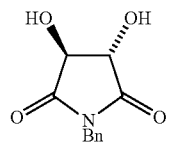

Benzylamine (3.7 mL, 33 mmol) and D-(+)-tartaric acid 17 (5 g, 33 mmol) in xylene (25 mL) were heated at reflux (160° C.) under vigorously stirring for 6 h using a Dean-Stark apparatus. The reaction mixture was cooled to room temperature, filtered and the residue was washed with acetone. Recrystallization from absolute ethanol (35 mL) gave the title compound (6 g, 81%) as a white solid. See, e.g., Nagel et al., 1984.

[α]$^{20}_D$=−139 (c 1.0, MeOH); m.p.=198° C.; $^1$H NMR (400 MHz, DMSO-d$_6$) δ 7.24-7.35 (m, 5H), 6.31 (d, J=5.4 Hz, 2H), 4.58 (d, J=14.8 Hz, 1H), 4.52 (d, J=14.8 Hz, 1H), 4.38 (d, J=5.4 Hz, 2H); $^{13}$C NMR (100 MHz, DMSO-d$_6$) δ 174.7, 136.1, 128.7, 127.6, 74.6, 41.3.

Synthesis 9

(3R,4R)-tert-Butyl 3,4-dihydroxypyrrolidine-1-carboxylate (19)

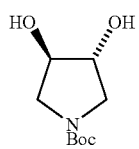

LiAlH$_4$ (2 M in THF, 18.5 mL, 37 mmol) was slowly added with stirring to a solution of 18 (3 g, 13.6 mmol) in THF (90 mL) at 0° C. The reaction mixture was heated at reflux for 16 h, cooled to 0° C. and slowly quenched with H$_2$O (1.48 mL), aqueous NaOH (15% wt. in H$_2$O, 1.48 mL) and H$_2$O (4.5 mL). The reaction mixture was filtered through Celite, washed with hot THF (50 mL) and the filtrate was concentrated in vacuo to give crude (3R,4R)-1-benzyl-3,4-dihydroxypyrrolidine as a pale yellow solid, which was used for the next step without further purification.

The crude benzylpyrrolidine in MeOH (35 ml) was allowed to react with Boc$_2$O (3.26 g, 15 mmol) and Pd/C (10% wt., 300 mg) and stirred under an atmosphere of hydrogen for 16 h. The mixture was filtered through Celite, concentrated under reduced pressure and the residue was recrystallized from hot EtOAc (25 mL) yielding 19 (2.0 g, 72%) as pale yellow crystals. See, e.g., Nagel et al., 1984.

R$_f$=0.22 (CH$_2$Cl$_2$:MeOH 19:1); $^1$H NMR (400 MHz, CDCl$_3$) δ 3.94 (brt, J=3.3 Hz, 2H), 3.67 (dd, J=12.0, 4.9 Hz, 1H), 3.63 (dd, J=12.0, 5.0 Hz, 1H), 3.42 (dd, J=12.0, 2.3 Hz, 2H), 3.37 (dd, J=12.1, 2.3 Hz, 2H), 1.44 (s, 9H); $^{13}$C NMR (400 MHz, CDCl$_3$) δ 153.9, 80.5, 64.2, 63.4, 48.8, 48.5, 28.4; MS (ESI): m/z 204 (M+H$^+$).

Synthesis 10

(3R,4R)-tert-Butyl 3-hydroxy-4-(methoxymethoxy)-pyrrolidine-1-carboxylate (20)

NaH (60% wt., 5.87 mmol, 235 mg) and MOMCl (445 μL, 5.87 mmol) were added with stirring to a solution of 19 (993 mg, 4.89 mmol) in dry THF (25 mL) at 0° C. The solution was allowed to reach room temperature and stirred for 5 h. Saturated aqueous NH$_{4}$O$_{1}$ (10 mL) was added and the aqueous layer was extracted with EtOAc (3×10 mL). The combined organic layers were washed with brine, dried over MgSO$_4$, filtered and concentrated under reduced pressure. The residue was purified by flash column chromatography (CH$_2$Cl$_2$:MeOH 19:1) to give the title compound (910 mg, 75%) as a pale yellow oil.

R$_f$=0.42 (CH$_2$Cl$_2$:MeOH 19:1); [α]$^{20}$$_D$=−45 (c 0.88, CH$_2$Cl$_2$); $^1$H NMR (400 MHz, CDCl$_3$) δ 4.68 (d, J=7.2 Hz, 1H), 4.66 (d, J=7.6 Hz, 1H), 4.18 (dd, J=9.6, 4.0 Hz, 1H), 3.94 (brs, 1H), 3.63 (brs, 2H), 3.38 (s, 3H), 3.26-3.35 (m, 2H), 1.43 (s, 9H); $^{13}$C NMR (100 MHz, CDCl$_3$) δ 154.7, 96.1, 82.3, 79.7, 74.1, 55.8, 51.3, 49.6, 28.6; HRMS (CI) calc. for C$_{11}$H$_{21}$NO$_5$ (M+H$^+$): 248.1498, found: 248.1494; Anal. calc. for C$_{11}$H$_{21}$NO$_5$: C, 53.43, H, 8.56, N, 5.66, found: C, 53.56, H, 8.62, N, 5.70.

Synthesis 11

(3S,4R)-tert-Butyl 3-azido-4-(methoxy-methoxy)-pyrrolidine-1-carboxylate (21)

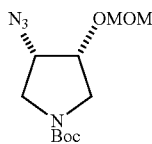

Et$_3$N (1.05 mL, 7.5 mmol) and methanesulfonyl chloride (440 μL, 5.6 mmol) were added with stirring to a solution of 20 (920 mg, 3.72 mmol) in CH$_2$Cl$_2$ (20 mL) at 0° C. The reaction mixture was stirred at 0° C. for 40 min, quenched with saturated aqueous NaHCO$_3$ (10 mL) and extracted with CH$_2$Cl$_2$ (3×10 mL). The combined organic layers were washed with brine, dried over MgSO$_4$, filtered and concentrated under reduced pressure. The resulting orange oil was used for the next step without further purification.

The crude oil was dissolved in dry DMF (20 mL), sodium azide (1.2 g, 18.6 mmol) was added and the resulting suspension was heated at 100° C. for 48 h, cooled to room temperature and diluted with water (10 mL) and Et$_2$O (10 mL). The aqueous layer was extracted with Et$_2$O (3×10 mL) and the combined organic layers were washed with water and brine, dried over MgSO$_4$, filtered and concentrated under reduced pressure. The residue was purified by flash column chromatography (hexane:Et$_2$O 2:3) to yield azide 21 (825 mg, 81%) as a colorless oil.

R$_f$=0.33 (hexane:Et$_2$O 2:3); [α]$^{20}$$_D$=−34 (c 1.07, CH$_2$Cl$_2$); IR (neat): v$_{max}$=2102, 1692, 1399, 1365, 1117, 995 cm$^{-1}$; $^1$H NMR (400 MHz, CDCl$_3$) δ 4.73 (d, J=7.0 Hz, 1H), 4.71 (d, J=7.0 Hz, 1H), 4.25-4.31 (m, 1H), 3.89-3.95 (m, 1H), 3.53-3.60 (m, 2H), 3.37-3.50 (m, 2H), 3.42 (s, 3H), 1.45 (s, 9H); $^{13}$C NMR (100 MHz, CDCl$_3$) δ 154.31, 96.1, 80.0, 76.6, 60.8, 55.9, 49.6, 48.0, 28.5; HRMS (CI) calc. for C$_{11}$H$_{20}$N$_4$O$_5$ (M+H$^+$): 273.1563, found 273.1569; Anal. calc. for C$_{11}$H$_{20}$N$_4$O$_5$: C, 48.52, H, 7.40, N, 20.58, found: C, 48.45, H, 7.31, N, 20.50.

Synthesis 12

(3S,4R)-tert-Butyl 3-amino-4-(methoxy-methoxy)-pyrrolidine-1-carboxylate (22)

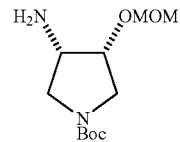

Azide 21 (100 mg, 0.37 mmol) in methanol (5 mL) was stirred and allowed to react with Pd/C (10% wt., 20 mg) under an atmosphere of hydrogen for 40 min. The mixture was filtered through Celite and the filtrate was concentrated under reduced pressure. The residue was purified by flash column chromatography (CH$_2$Cl$_2$:MeOH:30% wt. aqueous ammonia 92.75:7:0.25) to give 22 (89 mg, 98%) as a colorless oil.

R$_f$=0.40 (CH$_2$Cl$_2$:MeOH:30% wt aqueous ammonia 92.75:7:0.25); [α]$^{20}$$_D$=−21 (c 1.0, CH$_2$Cl$_2$); $^1$H NMR (400 MHz, CDCl$_3$) δ 4.62-4.69 (m, 2H), 3.96 (q, J=7.2 Hz, 1H), 3.48-3.55 (m, 2H), 3.40-3.46 (m, 2H), 3.34 (s, 3H), 2.98-3.10 (m, 1H), 1.55 (brs, 2H), 1.39 (s, 9H); $^{13}$C NMR (100 MHz, CDCl$_3$) δ 154.7, 96.0, 79.4, 77.6, 55.7, 53.8, 51.3, 50.0, 28.5; HRMS (CI) calc. for C$_{11}$H$_{22}$N$_2$O$_4$ (M+H$^+$): 247.1658, found 247.1653; Anal. calc. for C$_{11}$H$_{22}$N$_2$O$_4$: C, 53.64, H, 9.00, N, 11.37, found: C, 53.58, H, 8.96, N, 11.31.

3.2- Synthesis of Amine 31

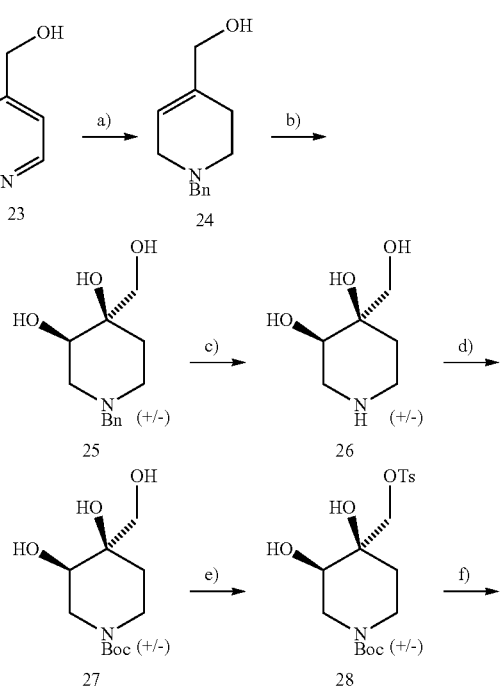

Scheme 5

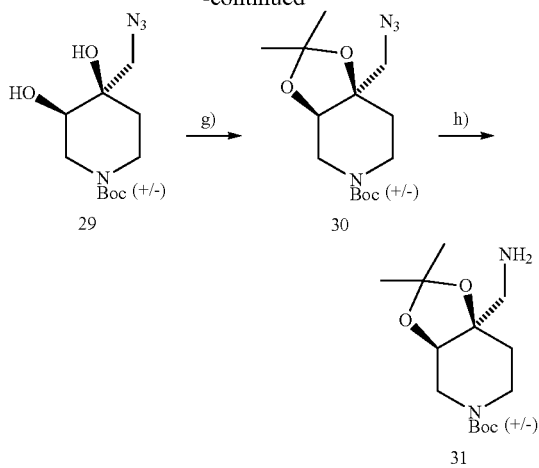

a) i) benzyl chloride, MeCN, reflux; ii) NaBH₄, MeOH, -20° C., 79% (2 steps).
b) K₂Os₂(OH)₄, (DHQD)₂PHAL, MeSO₂NH₂, K₂CO₃, ᵗBuOH/H₂O (1:1).
c) H₂, Pd/C, MeOH, 50 °C., 99%.
d) Boc₂O, CH₂Cl₂:MeOH (4:1), 81%.
e) TsCl, pyridine, 50%.
f) NaN₃, DMF, 60°C., 92%.
g) 2,2-dimethoxypropane, TsOH, aetone, 87%.
h) H₂, Pd/C, MeOH, 97%.

Synthesis 13

(1-Benzyl-1,2,3,6-tetrahydropyridin-4-yl)methanol (24)

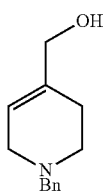

4-Pyridinemethanol (25.0 g, 229 mmol) was suspended in MeCN (250 mL) and benzyl chloride (31.5 ml, 275 mmol) was slowly added. The reaction was heated at reflux for 3 h, cooled to room temperature and concentrated under reduced pressure. The red residue was dissolved in methanol (350 mL) and cooled to −35° C. Sodium borohydride (17.4 g, 485 mmol) was added portionwise, maintaining the internal temperature below −20° C. Once the addition was complete the mixture was stirred for 30 min and quenched by the dropwise addition of water (50 mL). The mixture was concentrated under reduced pressure, diluted with CH₂Cl₂ (10 mL) and water (10 mL). The aqueous layer was extracted with CH₂Cl₂ (3×15 mL) and the combined organic layers were washed with brine, dried over MgSO₄ and concentrated under reduced pressure. The crude product was purified by flash column chromatography (hexane:EtOAc gradient 2:3 to 0:1) to yield 24 (32.0 g, 69%) as a white solid. See, e.g., Gijsen et al., 2008.

$^1$H NMR (400 MHz, CDCl₃) δ 7.30 (5H, m), 5.54 (1H, m), 4.68 (t, J=5.6 Hz, 1H), 3.83 (brd, J=5.5 Hz, 2H), 3.53 (2H, s), 2.87 (2H, m), 2.50 (t, J=5.7 Hz, 2H), 2.02 (2H, m); $^{13}$C NMR (100 MHz, CDCl₃) δ 139.1 137.1, 129.1, 128.6, 127.3, 118.9, 64.7, 62.3, 52.5, 49.8, 26.6.

Synthesis 14

1-Benzyl-4-(hydroxymethyl)piperidine-3,4-diol (25)

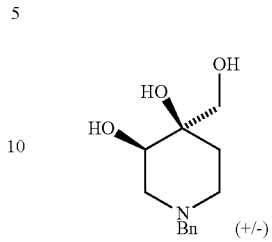

A pre-mixed clear solution of K₃Fe(CN)₆ (4.90 g, 15.0 mmol), K₂CO₃ (2.06 g, 15.0 mmol), (DHQD)₂PHAL (123 mg, 0.16 mmol), K₂OsO₂(OH)₄ (29.1 mg, 0.079 mmol) and MeSO₂NH₂ (476 mg, 5.00 mmol) in ᵗBuOH and H₂O (50 mL, 1:1) was cooled to 0° C. and tetrahydropyridine 24 (1.02 g, 5.00 mmol) was added. After stirring for 12 h at 0° C., sodium sulfite was added (30 g) and the reaction mixture was diluted with H₂O (20 mL). After 1 h vigorous stirring at room temperature, the reaction mixture was extracted with CH₂Cl₂ (3×10 mL). The combined organic extracts were dried over MgSO₄ and concentrated under reduced pressure. Purification by flash column chromatography (CH₂Cl₂: MeOH: concentrated aqueous NH₃ gradient 98:2:0.5 to 90:10:0.5) afforded 25 (485 mg, 41%) as an orange oil. See, e.g., Kolb et al., 1994.

$R_f$=0.20 (CH₂Cl₂:MeOH 19:1); IR (neat): $v_{max}$=3342, 1454, 1300, 1102, 1075, 1045, 1007, 963, 746, 698 cm$^{-1}$; $^1$H NMR (400 MHz, CDCl₃) δ 7.36-7.26 (m, 5H), 3.83 (dd, J=8.9, 4.1 Hz, 1H), 3.67-3.51 (m, 4H), 3.49 (s, 1H), 3.16 (brs, 2H), 2.71 (dd, J=10.9, 3.5 Hz, 1H), 2.53-2.34 (m, 3H), 1.69-1.57 (m, 2H); $^{13}$C NMR (100 MHz, CDCl₃) δ 137.3, 129.3, 128.3, 127.3, 71.0, 70.4, 68.7, 62.4, 54.9, 48.4, 31.5; HRMS (ESI) calc. for C₁₃H₁₉NO₃ (M+H⁺): 238.1443, found: 238.1445.

Synthesis 15

4-(Hydroxymethyl)piperidine-3,4-diol (26)

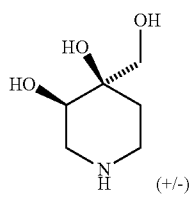

Triol 25 (440 mg, 1.85 mmol) was dissolved in MeOH (3 ml) and treated with Pd/C (15% wt., 22 mg) and stirred under an atmosphere of hydrogen for 10 h at 50° C. The mixture was filtered through Celite and the filtrate was concentrated under reduced pressure giving amine 26 (270 mg, 99%).

IR (neat): $v_{max}$=3273, 1646, 1533, 1420, 1272, 1052, 971, 856, 818 cm$^{-1}$; $^1$H NMR (400 MHz, CD₃OD) δ 3.61 (dd, J=10.1, 5.0 Hz, 1H), 3.59 (d, J=10.9 Hz, 1H), 3.43 (d, J=10.9 Hz, 1H), 3.35 (s, 2H), 2.88-2.70 (m, 4H), 1.64-1.61 (m, 2H), 1.69-1.57 (m, 2H); $^{13}$C NMR (100 MHz, CD₃OD) δ 73.1, 69.8, 67.9, 48.3, 41.7, 33.9; HRMS (CI) calc. for $C_6H_{13}NO_3$ (M+H+): 148.0974, found: 148.0974.

Synthesis 16 tert-Butyl-3,4-dihydroxy-4-(hydroxymethyl) piperidine-1-carboxylate (27)

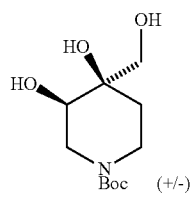 [SMILES: CC(C)(C)OC(=O)N1CC[C@@](O)(CO)[C@H](O)C1]

Boc$_2$O (370 mg, 1.70 mmol) and MeOH (0.5 mL) were added with stirring to a solution of amine 26 (250 mg, 1.70 mmol) in CH$_2$Cl$_2$ (2 mL) and the reaction mixture was stirred for 3 h at room temperature. The solvent was removed under reduced pressure and purification by flash column chromatography (CH$_2$Cl$_2$: MeOH gradient 19:1 to 9:1) afforded 27 (342 mg, 81%) of carbamate 27 as a white solid.

$R_f$=0.30 (CH$_2$Cl$_2$:MeOH 19:1); IR (neat): $v_{max}$=3335, 1664, 1425, 1366, 1274, 1250, 1156, 1057, 988, 960 cm$^{-1}$; $^1$H NMR (400 MHz, CDCl$_3$) δ 3.98-3.95 (m, 1H), 3.83 (brs, 1H), 3.72 (d, J=11.1 Hz, 1H), 3.57 (d, J=11.1 Hz, 1H), 3.11 (brs, 4H), 2.96 (dd, J=12.4, 10.6 Hz, 1H), 1.68-1.65 (m, 1H), 1.52-1.41 (m, 2H), 1.47 (s, 9H); $^{13}$C NMR (100 MHz, CDCl$_3$) δ 154.9, 80.2, 71.1, 70.5, 69.8, 44.8, 39.0, 31.7, 28.4; HRMS (CI) calc. for $C_{11}H_{21}NO_5$ (M+H+): 248.1498, found: 248.1503.

Synthesis 17 tert-Butyl 3,4-dihydroxy-4-((4-toluenesulfonyloxy)-methyl)piperidine-1-carboxylate (28)

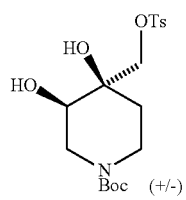 [SMILES: Cc1ccc(S(=O)(=O)OC[C@]2(O)CCN(C(=O)OC(C)(C)C)C[C@H]2O)cc1]

pTsCl (246 mg, 1.29 mmol) was added with stirring to a solution of triol 27 (290 mg, 1.17 mmol) in dry pyridine (2.4 mL). The reaction mixture was stirred for 14 h at room temperature, poured onto water and extracted with CH$_2$Cl$_2$ (3×3 mL). The combined organic extracts were dried over MgSO$_4$, filtered and concentrated under reduced pressure. Purification by flash column chromatography (hexane:EtOAc gradient 7:3 to 1:1) gave the sulfonate 28 (237 mg, 50%) as a white solid.

$R_f$=0.57 (hexane:EtOAc 2:3); m.p.=110° C.; IR (neat): $v_{max}$, =3411, 1686, 1427, 1359, 1255, 1183, 1169, 1070, 1054, 972, 840, 814, 667 cm$^{-1}$; $^1$H NMR (400 MHz, CDCl$_3$) δ 7.80 (d, J=8.3 Hz, 2H), 7.38 (d, J=8.3 Hz, 2H), 4.07 (d, J=10.1 Hz, 1H), 4.06 (brs, 1H), 3.90 (d, J=10.1 Hz, 1H), 3.70 (dd, J=10.5, 5.4 Hz, 1H), 3.89 (brs, 1H), 3.02 (brs, 2H), 2.88 (brs, 1H), 2.61 (brs, 1H), 2.49 (s, 3H), 1.71-1.59 (m, 2H), 1.48 (s, 9H); $^{13}$C NMR (100 MHz, CDCl$_3$) δ 154.6, 145.3, 132.3, 130.0, 128.0, 80.1, 72.7, 70.9, 66.7, 44.1, 38.9, 31.7, 28.4, 21.7; HRMS (ESI) calc. for $C_{18}H_{27}NO_7S$ (M+Na+): 424.1406, found: 424.1399.

Synthesis 18 tert-Butyl 4-(azidomethyl)-3,4-dihydroxy-piperidine-1-carboxylate (29)

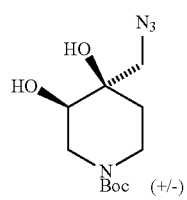 [SMILES: CC(C)(C)OC(=O)N1CC[C@@](O)(CN=[N+]=[N-])[C@H](O)C1]

NaN$_3$ (109 mg, 1.68 mmol) was added with stirring to a solution of 4-toluenesulfonate 28 (225 mg, 0.560 mmol) in dry DMF (5.6 mL). The reaction mixture was stirred for 12 h at 60° C., cooled to room temperature and H$_2$O (25 mL) was added. The reaction mixture was extracted with Et$_2$O (3×10 mL) and the combined organic extracts were washed with brine, dried over MgSO$_4$, filtered and concentrated under reduced pressure. Purification by flash column chromatography (hexane:Et$_2$O 7:3 to 1:4) yielded azide 29 (140 mg, 92%) as a colorless oil.

$R_f$=0.29 (hexane:EtOAc 3:2); IR (neat): $v_{max}$=3386, 2101, 1664, 1426, 1367, 1275, 1246, 1152, 1068, 873, 763 cm$^{-1}$; $^1$H NMR (400 MHz, CDCl$_3$) δ 4.02-4.01 (m, 1H), 3.83 (brs, 1H), 3.63-3.59 (m, 1H), 3.49 (d, J=12.2 Hz, 1H), 3.37 (d, J=12.2 Hz, 1H), 3.09 (brt, J=11.3 Hz, 1H), 2.99-2.51 (brs, 2H), 2.92 (t, J=11.5 Hz, 1H), 1.79 (d, J=14.0 Hz, 1H), 1.63-1.47 (m, 1H), 1.47 (s, 9H); $^{13}$C NMR (100 MHz, CDCl$_3$) δ 154.8, 80.3, 71.9, 68.2, 58.2, 44.8, 39.2, 32.5, 28.4; HRMS (CI) calc. for $C_{11}H_{20}N_4O_4$ (M+NH4+): 290.1828, found: 290.1831.

Synthesis 19 tert-Butyl 7a-(azidomethyl)-2,2-dimethyl-tetrahydro-[1,3]dioxolo[4,5-c]pyridine-5(6H)-carboxylate (30)

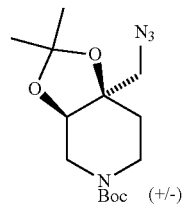 [SMILES: CC(C)(C)OC(=O)N1CC[C@]2(CN=[N+]=[N-])OC(C)(C)O[C@@H]2C1]

Azide 29 (130 mg, 0.48 mmol) was dissolved in acetone and dimethoxypropane (1:1; 6 mL) and pTsOH (9 mg, 0.05 mmol) was added. The reaction mixture was stirred at room temperature for 2 h and concentrated under reduced pressure. The residue was purified by flash column chromatography (hexane:EtOAc 1:1) giving azide 30 (130 mg, 87%) as a colorless oil.

$R_f$=0.6 (hexane:EtOAc 1:1); $^1$H NMR (400 MHz, CDCl$_3$) δ 4.20-4.08 (m, 2H), 3.62-3.20 (m, 4H), 3.10-3.02 (m, 1H), 1.88 (m, 1H), 1.51-1.44 (m, 16H); HRMS (ESI) calc. for $C_{14}H_{23}N_4O_4$ (M+Na$^+$): 311.1719, found: 311.1702.

Synthesis 20 tert-Butyl 7a-(aminomethyl)-2,2-dimethyl-tetrahydro-[1,3]dioxolo[4,5-c]pyridine-5(6H-1)-carboxylate (31)

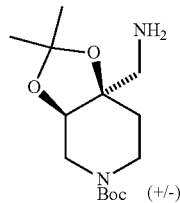

Azide 30 (80 mg, 0.26 mmol) was dissolved in MeOH (5 mL), and stirred and allowed to react with Pd/C (10% wt., 60 mg) under a hydrogen atmosphere for 3 h. The mixture was filtered through Celite, washed with MeOH and concentrated under reduced pressure to afford amine 31 (72 mg, 0.25 mmol, 97%) as a colorless oil which was used in the next step without further purification.

$R_f$=0.25 (CH$_2$Cl$_2$:MeOH 19:1).

3.3—Synthesis of Piperidine 38

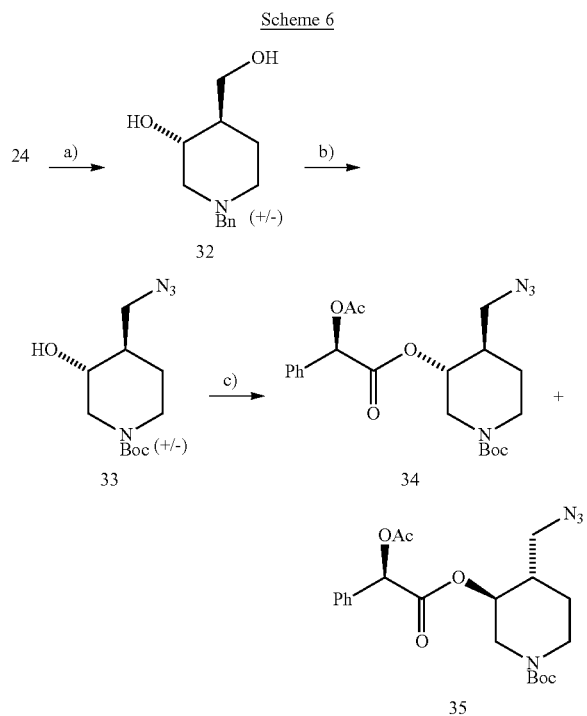

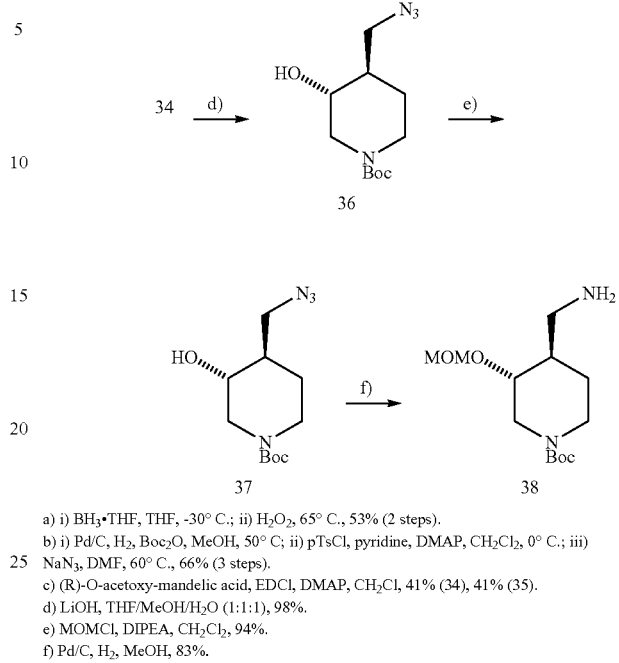

a) i) BH$_3$•THF, THF, -30° C.; ii) H$_2$O$_2$, 65° C., 53% (2 steps).
b) i) Pd/C, H$_2$, Boc$_2$O, MeOH, 50° C; ii) pTsCl, pyridine, DMAP, CH$_2$Cl$_2$, 0° C.; iii) NaN$_3$, DMF, 60° C., 66% (3 steps).
c) (R)-O-acetoxy-mandelic acid, EDCI, DMAP, CH$_2$Cl, 41% (34), 41% (35).
d) LiOH, THF/MeOH/H$_2$O (1:1:1), 98%.
e) MOMCl, DIPEA, CH$_2$Cl$_2$, 94%.
f) Pd/C, H$_2$, MeOH, 83%.

Synthesis 21

1-Benzyl-4-(hydroxymethyl)piperidin-3-ol (32)

Tetrahydropyridine 24 (2.00 g, 9.85 mmol) was dissolved in THF (19 ml) and cooled to -30° C. Borane.THF complex (1 M in THF, 19.0 ml, 19.0 mmol) was added dropwise and the mixture allowed to warm to room temperature overnight. The solution was cooled to -10° C. and quenched by addition of water (0.5 mL). Hydrogen peroxide (30% in water, 1.24 ml) and sodium hydroxide (3 M in water, 1.37 ml) were simultaneously added dropwise. Sodium hydroxide (50% in water, 2.5 ml) was added and the mixture heated at reflux for 4 h. The reaction mixture was cooled to room temperature and the white precipitate removed by filtration. The filtrate was concentrated under reduced pressure, taken up in CH$_2$Cl$_2$ and water, poured onto saturated aqueous NaHCO$_3$ (10 mL). The aqueous layer was extracted with CH$_2$Cl$_2$ (3×10 mL) and the combined organic layers were washed with brine, dried over Na$_2$SO$_4$ and concentrated in vacuo. The product was purified by trituration from i-Pr$_2$O to yield 41 (1.14 g, 53%). See, e.g., Gijsen et al., 2008.

$^1$H NMR (400 MHz, CDCl$_3$) δ 7.32 (m, 5H), 3.72 (m, 3H), 3.02 (dd, J=10.7, 4.4 Hz, 1H), 2.85 (md, J=11.1 Hz,

1H), 2.63 (s, 1H), 2.19 (brs, 1H), 2.00 (td, J=11.6, 2.5 Hz, 1H), 1.89 (t, J=10.2 Hz, 1H), 1.59 (m, 3H), 1.28 (qd, J=12.8, 4.2 Hz, 1H); $^{13}$C NMR (100 MHz, CDCl$_3$) δ 138.0, 129.2, 128.2, 127.1, 73.1, 68.0, 62.7, 60.0, 52.6, 44.5, 26.1.

Synthesis 22 tert-Butyl 4-(azidomethyl)-3-hydroxy-piperidine-1-carboxylate (33)

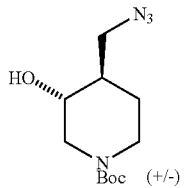 [SMILES: CC(C)(C)OC(=O)N1CC[C@H](CN=[N+]=[N-])[C@@H](O)C1]

Piperidine 32 (2.62 g, 11.9 mmol) and Pd/C (10% wt., 263 mg) were suspended in MeOH (25.0 ml) and Boc$_2$O (3.89 g, 17.8 mmol) was added. The atmosphere was replaced by hydrogen and the mixture heated to 50° C. overnight. The suspension was cooled to room temperature, filtered first through Celite and subsequently through a plug of silica to yield the title compound (2.74 g, 99%), which was used in the next step without further purification.

Crude tert-butyl-3-hydroxy-4-(hydroxymethyl) piperidine-1-carboxylate (414 mg, 1.78 mmol) was dissolved in CH$_2$Cl$_2$ (1 ml) and pyridine (1 ml) and cooled to 0° C. pTsCl (358 mg, 1.87 mmol) was added portionwise followed by DMAP (1.00 mg, 0.008 mmol). The mixture was stirred for 48 h, diluted with CH$_2$Cl$_2$ (5 mL) and poured onto hydrochloric acid (0.5 M, 5 mL). The aqueous layer was extracted with CH$_2$Cl$_2$ (3×3 mL) and the combined organic layers were washed with brine, dried over MgSO$_4$ and concentrated under reduced pressure. The product was purified by flash column chromatography (hexane:EtOAc gradient 1:9 to 1:1) to yield tert-butyl 3-hydroxy-4-(toluene-4-sulfonyloxymethyl)piperidine-1-carboxylate (493 mg, 72%), which was used directly without further purification.

tert-butyl-3-hydroxy-4-(toluene-4-sulfonyloxy-methyl) piperidine-1-carboxylate (425 mg, 1.10 mmol) was dissolved in DMF (10 ml) and NaN$_3$ (86.0 mg 1.32 mmol) was added. The mixture was heated to 60° C. overnight, cooled to room temperature and poured onto brine. The aqueous layer was extracted with Et$_2$O (3×3 mL) and the combined organic layers were washed with brine, dried over MgSO$_4$ and concentrated under reduced pressure. The product was purified by flash column chromatography (hexane:EtOAc gradient 9:1 to 3:1) to yield azide 33 (253 mg, 99%).

$^1$H NMR (500 MHz, DMSO-d$_6$) δ 4.58 (brs, 1H), 4.02 (ddd, J=12.9, 5.1, 1.8 Hz, 1H), 3.89 (dddd, J=13.2, 4.5, 2.7, 1.8 Hz, 1H), 3.56 (dd, J=12.4, 3.8 Hz, 1H), 3.35 (dd, J=12.2, 6.8 Hz, 1H), 3.19 (td, J=9.7, 4.8 Hz, 1H), 2.68 (ddd, J=13.2, 12.3, 3.0 Hz, 1H), 2.48 (m, 1H), 1.73 (dq, J=13.3, 3.0 Hz, 1H), 1.56 (m, 1H), 1.42 (s, 9H), 1.22 (qd, J=12.0, 4.5 Hz, 1H); $^{13}$C NMR (125 MHz, DMSO-d$_6$) δ 153.3, 78.0, 66.4, 52.5, 49.4, 42.8, 42.3, 27.5, 26.7.

Synthesis 23

(3R,4R)-tert-Butyl 3-((R)-2-acetoxy-2-phenyl-acetoxy)-4-(azidomethyl)piperidine-1-carboxylate (34)

(3S,4S)-tert-Butyl 3-((R)-2-acetoxy-2-phenyl-acetoxy)-4-(azidomethyl)piperidine-1-carboxylate (35)

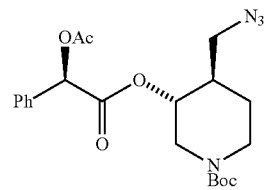

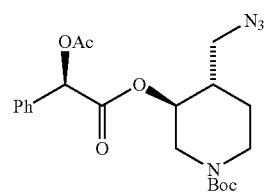

Azide 33 (7.13 g, 29.0 mmol), (R)—O-acetoxy-mandelic acid (6.75 g, 34.7 mmol) and DMAP (354 mg, 2.90 mmol) were dissolved in CH$_2$Cl$_2$ (100 mL). EDCl (6.66 g, 34.7 mmol) was added and the reaction mixture was stirred for 16 h. Reaction was quenched by addition of water (150 mL). The phases were separated and the aqueous phase was extracted with CH$_2$Cl$_2$ (3×100 mL). The combined organic phases were dried over MgSO$_4$ and concentrated under reduced pressure. The diastereoisomeric mixture was separated by preparative HPLC to afford 34 (5.02 g, 41%) and 35 (5.00 g, 41%) as colorless oils.

34: R$_f$=0.41 (hexane:Et$_2$O 1:1); [α]$^{25}$$_D$=−51.6 (c 2.0, CH$_2$Cl$_2$); $^1$H NMR (400 MHz, CDCl$_3$) δ 7.45-7.44 (m, 2H), 7.40-7.38 (m, 3H), 5.82 (brs, 1H), 4.65 (brs, 1H), 4.02 (brs, 2H), 3.48 (d, 1H, J=11.8 Hz), 3.22 (dd, J=12.4, 7.2 Hz, 1H), 2.64 (t, J=12.5 Hz, 1H), 2.44 (t, J=11.3 Hz, 1H), 2.20 (s, 3H), 1.87-1.77 (m, 2H), 1.41 (s, 10H); $^{13}$C NMR (100 MHz, CDCl$_3$) δ 170.7, 168.3, 154.4, 133.3, 129.6, 129.0, 127.6, 80.4, 74.7, 70.2, 52.6, 46.0, 42.8, 41.3, 28.4, 27.8, 20.8; HRMS (ESI) calc. for C$_{21}$H$_{28}$N$_4$O$_6$ (M+Na$^+$): 455.1907, found: 455.1896.

35: R$_f$=0.38 (hexane/Et$_2$O 1:1); [α]$^{25}$$_D$=−86.1 (c 2.0, CHCl$_3$); $^1$H NMR (400 MHz, CDCl$_3$) δ 7.47-7.45 (m, 2H), 7.40-7.39 (m, 3H), 5.88 (s, 1H), 4.53 (bs, 1H), 4.27 (bs, 1H), 4.01 (bs, 1H), 2.88 (d, J=11.4 Hz, 1H), 2.72 (dd, J=12.1, 6.9 Hz, 1H), 2.64 (t, J=11.9 Hz, 1H), 2.19 (s, 3H), 1.73-1.59 (m, 3H), 1.44 (s, 9H), 1.31 (dq, J=12.4, 4.3 Hz, 1H); $^{13}$C NMR (100 MHz, CDCl$_3$) δ 170.3, 168.0, 154.4, 133.8, 129.6, 129.0, 127.7, 80.3, 74.4, 70.6, 52.1, 46.5, 42.7, 41.0, 28.4, 27.6, 20.8; HRMS (ESI) calc. for C$_{21}$H$_{28}$N$_4$O$_6$ (M+Na$^+$): 455.1907, found: 455.1905.

Synthesis 24

(3R,4R)-tert-Butyl 4-(azidomethyl)-3-hydroxypiperidine-1-carboxylate (36)

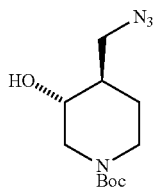

Mandelic ester 34 (5.00 g, 11.6 mmol) and LiOH.H$_2$O (1.21 g, 28.9 mmol) were dissolved in THF, MeOH and H$_2$O (1:1:1; 60 mL) and stirred for 2 h. The reaction mixture was diluted with water (100 mL) and extracted with EtOAc (4×50 mL). The combined organic phases were dried over MgSO$_4$ and concentrated under reduced pressure. The resultant alcohol 36 (2.91 g, 98%) was analytically pure and could be used without further purification.

[α]$^{25}_D$=+20.1 (c 4.0, MeOH); $^1$H NMR (500 MHz, DMSO-d$_6$) δ 4.58 (brs, 1H), 4.02 (ddd, J=12.9, 5.1, 1.8 Hz, 1H), 3.89 (dddd, J=13.2, 4.5, 2.7, 1.8 Hz, 1H), 3.56 (dd, J=12.4, 3.8 Hz, 1H), 3.35 (dd, J=12.2, 6.8 Hz, 1H), 3.19 (td, J=9.7, 4.8 Hz, 1H), 2.68 (ddd, J=13.2, 12.3, 3.0 Hz, 1H), 2.48 (m, 1H), 1.73 (dq, J=13.3, 3.0 Hz, 1H), 1.56 (m, 1H), 1.42 (s, 9H), 1.22 (dq, J=12.0, 4.5 Hz, 1H); $^{13}$C NMR (125 MHz, DMSO-d$_6$) δ 153.3, 78.0, 66.4, 52.5, 49.4, 42.8, 42.3, 27.5, 26.7.

Synthesis 25

(3R,4R)-tert-Butyl 4-(azidomethyl)-3-(methoxymethoxy)piperidine-1-carboxylate (37)

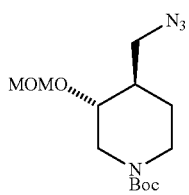

Di-iso-propylethylamine (0.224 mL, 1.29 mmol) and MOMCl (98 μL, 1.29 mmol) were added dropwise with stirring to a solution of alcohol 36 (165 mg, 0.644 mmol) in CH$_2$Cl$_2$ (5 mL) at 0° C. After 14 h at room temperature, the reaction mixture was poured onto saturated aqueous NH$_4$Cl (5 mL) and extracted with Et$_2$O (3×2 mL). The combined organic extracts were dried over MgSO$_4$, filtered and concentrated under reduced pressure. Purification by flash column chromatography (hexane:Et$_2$O gradient 4:1 to 1:1) to afforded azide 37 (144 mg, 74%) as a colorless oil.

R$_f$=0.69 (hexane:Et$_2$O 7:3); IR (neat): v$_{max}$=3286, 1693, 1421, 1366, 1278, 1153, 1140, 1101, 1037 cm$^{-1}$; $^1$H NMR (400 MHz, CDCl$_3$) δ 4.75 (d, J=6.8 Hz, 1H), 4.67 (d, J=6.8 Hz, 1H), 4.39 (brs, 1H), 4.08 (brs, 1H), 3.59 (dd, J=12.2, 3.3 Hz, 1H), 3.43 (s, 3H), 3.43-3.38 (m, 1H), 3.34 (td, J=10.0, 4.9 Hz, 1H), 2.70 (brt, J=12.5 Hz, 1H), 2.55 (brt, J=9.9 Hz, 1H), 1.84-1.79 (m, 1H), 1.76-1.67 (m, 1H), 1.47 (s, 9H), 1.40 (dq, J=12.5, 4.5 Hz, 1H); $^{13}$C NMR (100 MHz, CDCl$_3$) δ 154.5, 96.2, 79.9, 73.9, 55.8, 53.1, 47.7, 43.5, 42.4, 28.4, 28.0; HRMS (Cl) calc. for C$_{13}$H$_{24}$N$_4$O$_4$ (M+Na$^+$): 323.1695, found: 323.1693.

Synthesis 26

(3R,4R)-tert-Butyl 4-(aminomethyl)-3-(methoxymethoxy)piperidine-1-carboxylate (38)

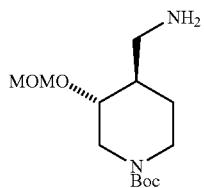

Pd/C (15% wt., 19.5 mg) was added to a degassed solution of azide 37 (130 mg, 0.433 mmol) in MeOH (2 mL). After 1.5 h under hydrogen atmosphere, the reaction mixture was filtered through Celite and concentrated under reduced pressure. Purification by flash column chromatography (CH$_2$Cl$_2$:MeOH: NH$_4$OH gradient 94:5:1 to 87.5:12.5:1) to afforded 38 (98.7 mg, 83%) as a colorless oil.

R$_f$=0.35 (CH$_2$Cl$_2$MeOH 9:1); IR (neat): v$_{max}$=1689, 1421, 1365, 1244, 1151, 1102, 1030, 917, 882 cm$^{-1}$; $^1$H NMR (400 MHz, CD$_3$OD) δ 4.73 (d, J=6.9 Hz, 1H), 4.66 (d, J=6.9 Hz, 1H), 4.29-4.26 (m, 1H), 4.00-3.96 (m, 1H), 3.39 (s, 3H), 3.25 (td, J=9.8, 4.6 Hz, 1H), 2.93 (dd, J=12.8, 4.7 Hz, 1H), 2.78 (brt, J=13.2 Hz, 1H) 2.75-2.56 (m, 1H), 2.58 (dd, J=12.8, 6.8H, 1H), 1.84-1.80 (m, 1H), 1.64-1.54 (m, 1H), 1.45 (s, 9H), 1.23 (m, 1H); $^{13}$C NMR (100 MHz, CD$_3$OD) δ 156.4, 97.4, 81.3, 77.2, 56.1, 49.5, 45.1, 44.5, 28.7; HRMS (Cl) calc. for C$_{13}$H$_{26}$N$_2$O$_4$ (M+H$^+$): 275.1971, found: 275.1970.

3.4—Synthesis of Piperidine 41

Scheme 7

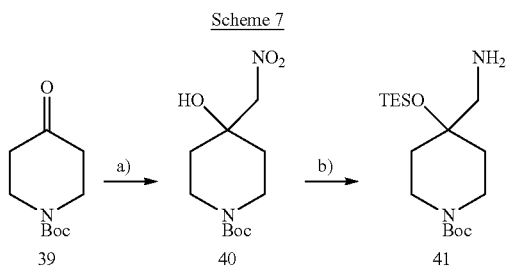

a) MeNO$_2$, Et$_3$N, 93%.
b) i) Et$_3$SiCl (TESCl), imidazole, DMF, 65° C.; ii) Pd/C, AcOH, H$_2$, MeOH, 40%.

Synthesis 27 tert-Butyl 4-hydroxy-4-(nitromethyl)-piperidine-1-carboxylate (40)

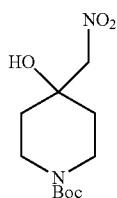

tert-Butyl-4-oxopiperidine-1-carboxylate 39 (10.0 g, 50.2 mmol) was added portion-wise with stirring to a solution of nitromethane (100 mL) and Et$_3$N (42.8 mL, 301 mmol) and the mixture was stirred for 4 days at room temperature. The reaction mixture was diluted with EtOAc (80 mL) and washed with water, saturated aqueous NH$_4$Cl and brine, dried over MgSO$_4$ and concentrated under reduced pressure to give the title compound (12.1 g, 93%) as a white solid. See, e.g., Bosmans et al., 2005.

$R_f$=0.10 (hexanes:EtOAc 4:1); m.p.=141° C.; IR (neat): $v_{max}$=3383, 1660, 1545 cm$^{-1}$; $^1$H NMR (CDCl$_3$, 400 MHz) δ 4.42 (s, 2H), 3.93-3.90 (m, 2H), 3.22-3.15 (m, 2H), 2.99 (brs, 1H), 1.68-1.65 (m, 2H), 1.61-1.57 (m, 2H), 1.45 (s, 9H); $^{13}$C NMR (100 MHz, CD$_3$OD) δ 154.6, 84.7, 79.9, 69.1, 40.0, 34.2, 28.4; HRMS (ESI) calc. for C$_{11}$H$_{20}$N$_2$O$_5$ (M+H$^+$): 260.1367, found: 260.1450.

Synthesis 28 tert-Butyl 4-(aminomethyl)-4-hydroxy-piperidine-1-carboxylate (41)

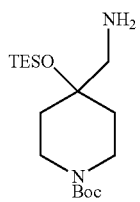

A stirred solution of piperidine 40 (200 mg, 0.77 mmol) and imidazole (260 mg, 3.82 mmol) in TESCl (1 mL) and DMF (0.5 mL) was heated at 70° C. After 20 h, the mixture was cooled to room temperature and treated with water (100 mL). Following an extraction with ethyl acetate (3×50 mL) the combined organic phases were washed with brine (1×50 mL), dried (MgSO$_4$) and concentrated in vacuo to give an oily yellow residue containing the TES ether intermediate. This material was used in the next step of the reaction sequence without further purification.

A stirred solution of the TES ether intermediate, in dry MeOH (5 mL), was treated with Pd/C (10% wt., 200 mg) and placed under an atmosphere of hydrogen at 22 bars. After 48 h, the ensuing mixture was filtered and the filtrate was concentrated in vacuo to give a yellow oil. Subjection of this material to flash chromatography (CH$_2$Cl$_2$:MeOH gradient 19:1 to 9:1) afforded the amine 41 (182 mg, 69%) as a colorless oil.

$R_f$=0.5 (EtOAc); IR (neat): $v_{max}$=3396, 2953, 2913, 2875, 1692, 1421, 1365, 1243, 1155, 1060 cm$^{-1}$; $^1$H NMR (CDCl$_3$, 400 MHz) δ 3.61-3.57 (m, 2H), 3.28 (ddd, J=13.2, 8.8, 4.3 Hz, 2H), 2.67 (s, 2H), 1.55-1.51 (m, 2H), 1.43 (s, 9H), 1.17 (s, 2H), 0.94 (t, J=7.9 Hz, 9H), 0.59 (q, J=7.9 Hz, 6H); $^{13}$C NMR (100 MHz, CD$_3$OD) δ 154.8, 79.3, 74.1, 51.5, 40.1, 35.0, 28.4, 7.2, 6.9; HRMS (ESI) calc. for C$_{17}$H$_{37}$N$_2$O$_3$Si (M+H$^+$): 345.2573, found: 345.2563.

3.5—Synthesis of Pyrrolidine 46

Scheme 8

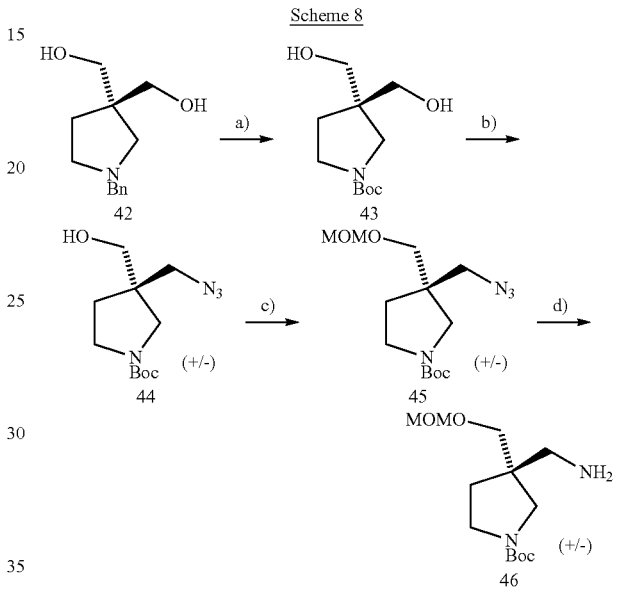

a) Pd/C, H$_2$, Boc$_2$O, MeOH, 50° C., 99%.
b) i) pTsCl, pyridine, DMAP, CH$_2$Cl$_2$; ii) NaN$_3$, DMF, 60° C., 53% (2 steps).
c) MOMCl, iso-Pr$_2$NEt, CH$_2$Cl$_2$, 0° C. to room temperature, 70%.
d) Pd/C, H$_2$, MeOH, 95%.

Synthesis 29 tert-Butyl 3,3-bis(hydroxymethyl)-pyrrolidine-1-carboxylate (43)

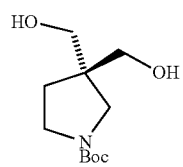

Pyrrolidine 42 (see, e.g., Xu et al., 2011) (2.62 g, 11.9 mmol) and Pd/C (10% wt., 263 mg) were suspended in MeOH (25.0 mL) and Boc$_2$O (3.89 g, 17.8 mmol) was added. The atmosphere was replaced by hydrogen and the mixture heated to 50° C. overnight. The suspension was cooled to room temperature and filtered first through Celite and subsequently through a small silica plug to yield carbamate 43 (2.74 g, 99%).

$R_f$=0.43 (CH$_2$Cl$_2$:MeOH:saturated aqueous NH$_3$ 10:1: 0.1); IR (neat): $v_{max}$=3394, 1666, 1610, 1574, 1477, 1415, 1366, 1254, 1149, 1107, 1039, 914, 879, 771, 731, 700, 646 cm$^{-1}$; $^1$H NMR (400 MHz, CDCl$_3$) δ 4.06 (brs, 1H), 3.91 (brs, 1H), 3.60 (s, 4H), 3.39-3.32 (m, 2H), 3.20-3.17 (m, 2H), 1.70 (t, J=7.2 Hz, 2H), 1.41 (s, 9H).

Synthesis 30 tert-Butyl 3-(azidomethyl)-3-(hydroxymethyl) pyrrolidine-1-carboxylate (44)

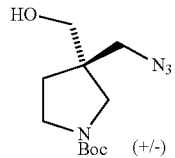 [SMILES: CC(C)(C)OC(=O)N1CC[C@@](CO)(CN=[N+]=[N-])C1]

Diol 43 (750 mg, 3.2 mmol) was dissolved in CH$_2$Cl$_2$ and pyridine (3.6 mL, 1:1). The mixture was cooled to 0° C. and treated with pTsCl (0.648 mg, 3.4 mmol) and DMAP (2 mg, 0.02 mmol). The mixture was stirred for 24 h at room temperature. The mixture was concentrated under reduced pressure, dissolved in DMF (15 ml), treated with NaN$_3$ (1.85 mg, 22.4 mmol) and the mixture was heated to 85° C. for 24 h. The mixture was re-cooled to room temperature, filtered and the filtrate was extracted with EtOAc and washed with brine. The combined organic layers were dried (Na$_2$SO$_4$) and concentrated under reduced pressure. The title azide was obtained as a colorless oil (434 mg, 53%) after flash column chromatography (hexane:EtOAc gradient 9:1 to 7:3).

$^1$H NMR (400 MHz, CDCl$_3$) δ 3.57 (d, J=3.7 Hz, 2H), 3.44 (m, 4H), 3.22 (td, J=18.1, 10.8 Hz, 2H), 2.17 (m, 1H), 1.78 (m, 1H), 1.45 (s, 9H); MS (CI): m/z 279.2 (M+Na$^+$).

Synthesis 31 tert-Butyl 3-(azidomethyl)-3-((methoxy-methoxy)methyl)pyrrolidine-1-carboxylate (45)

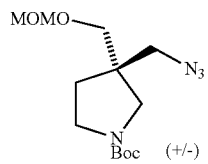

Azide 44 (650 mg, 2.54 mmol) was dissolved in CH$_2$Cl$_2$ (8 mL) and treated with iso-Pr$_2$NEt (1.8 mL, 10.33 mmol). The mixture was cooled to 0° C., allowed to react with MOMCl (0.6 mL, 7.9 mmol) and stirred at room temperature overnight. The title azide was obtained (535 mg, 70%) after flash column chromatography (hexane:EtOAc gradient 9:1 to 4:1).

$^1$H NMR (400 MHz, CDCl$_3$) δ 4.62 (s, 2H), 3.43 (m, 6H), 3.36 (s, 3H), 3.22 (m, 2H), 1.79 (s, 2H), 1.45 (m, 9H); $^{13}$C NMR (100 MHz, CDCl$_3$) δ 154.5, 96.6, 79.5, 69.2, 55.4, 54.7, 51.8, 44.4, 30.9, 30.3, 28.5.

Synthesis 32 tert-Butyl 3-(aminomethyl)-3-((methoxy-methoxy)methyl)pyrrolidine-1-carboxylate (46)

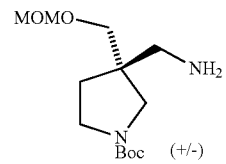

Azide 45 (460 mg, 15.3 mmol) in MeOH (8 mL) was allowed to react with Pd/C (10% wt., 50 mg) and stirred under an atmosphere of hydrogen for 2 h. The mixture was filtered through a membrane filter. The title amine was obtained as a colorless oil (400 mg, 95%), which was used without further purification.

$^1$H NMR (400 MHz, CDCl$_3$) δ 4.61 (s, 2H), 3.45 (m, 4H), 3.36 (s, 3H), 3.20 (m, 2H), 2.76 (m, 2H), 1.75 (m, 2H), 1.45 (s, 9H); $^{13}$C NMR (100 MHz, CDCl$_3$) δ 154.5, 96.6, 79.5, 70.1, 55.4, 54.7, 51.8, 44.4, 30.9, 30.3, 28.5; MS (ESI): m/z 275.2 (M+H$^+$).

3.6—Synthesis of Pyrrolidine 51

Scheme 9

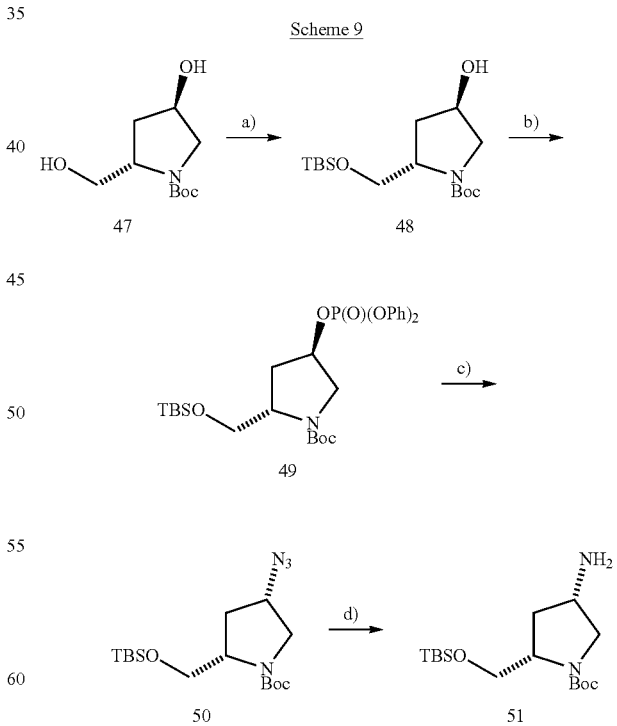

a) t-BuMe$_2$SiCl (TBSCl), imidazole, CH$_2$Cl$_2$, 63%.
b) (PhO)$_2$P(O)N$_3$ (DPPA), DBU, THF, 0° C. to room temperature, 91%.
c) NaN$_3$, DMF, 80° C., 46%.
d) Pd/C, H$_2$, MeOH, 81%.

Synthesis 33

(2S,4R)-tert-Butyl 2-((tert-butyldimethyl-silyloxy)methyl)-4-hydroxypyrrolidine-1-carboxylate (48)

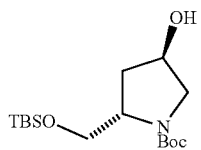 [SMILES: CC(C)(C)OC(=O)N1C[C@H](O)C[C@H]1CO[Si](C)(C)C(C)(C)C]

Imidazole (0.313 g, 4.6 mmol) and TBSCl (0.415 g, 2.76 mmol) were added to a solution of alcohol 47 (0.50 g, 2.30 mmol) in $CH_2Cl_2$ (5 mL) and the reaction mixture was stirred at room temperature for 24 h. The reaction mixture was poured onto water (5 mL), extracted with $Et_2O$ (5×5 mL) and the combined organic layers were washed with brine, dried over $MgSO_4$, and concentrated under reduced pressure. Purification by flash column chromatography (hexane:EtOAc gradient 2:1 to 1:1) gave 48 (0.480 g, 63%) as a clear oil. See, e.g., Vince et al., 1991.

$R_f$=0.33 (hexane:EtOAc 1:1); $[\alpha]^{23}_D$=−54.44 (c 1.15, $CHCl_3$); IR (neat): $v_{max}$=3427, 1696, 1670, 1399, 1252, 1165, 1109 cm$^{-1}$; HRMS (ESI) calc. for $C_{16}H_{34}NO_4Si$ (M+H$^+$): 332.2257, found: 332.2246.

Synthesis 34

(2S,4R)-tert-Butyl 2-((tert-butyldimethyl-silyloxy)methyl)-4-(diphenoxyphos-phoryloxy)pyrrolidine-1-carboxylate (49)

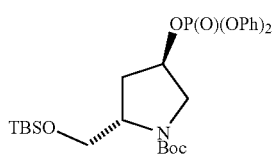

DPPA (0.327 mL, 1.52 mmol) and DBU (0.228 mL, 1.52 mmol) were added dropwise with stirring to a solution of alcohol 48 (0.420 g, 1.27 mmol) in THF (2.5 mL) at 0° C. and the mixture was allowed to warm to room temperature. After 24 h, the reaction mixture was diluted with $Et_2O$ (5 mL), poured onto saturated aqueous $NaHCO_3$ (5 mL) and extracted with $Et_2O$ (5×5 mL). The combined organic layers were washed with brine, dried over $MgSO_4$, and concentrated under reduced pressure. Purification by flash column chromatography (hexane:EtOAc 4:1) gave phosphate 49 (655 mg, 91%) as a clear oil.

$R_f$=0.64 (hexane:EtOAc 1:1); IR (neat): $v_{max}$=1695, 1488, 1397, 1187, 1162 cm$^{-1}$; HRMS (ESI) calc. for $C_{28}H_{43}NO_7SiP$ (M+H$^+$): 564.2546, found: 564.2563.

Synthesis 35

(2S,4S)-tert-Butyl-4-azido-2-((tert-butyl-dimethylsilyloxy)methyl)pyrrolidine-1-carboxylate (50)

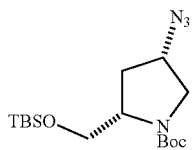 [SMILES: CC(C)(C)OC(=O)N1C[C@@H](N=[N+]=[N-])C[C@H]1CO[Si](C)(C)C(C)(C)C]

A suspension of phosphate 49 (0.655 g, 1.16 mmol) and $NaN_3$ (0.9 g, 11.6 mmol) in DMF (2 mL) was heated to 80° C. for 3 days. The reaction mixture was diluted with $Et_2O$ (10 mL), poured onto water (10 mL) and extracted with $Et_2O$ (6×5 mL). The combined organic layers were washed with water, brine, dried over $MgSO_4$ and concentrated under reduced pressure. Purification by flash column chromatography (hexane:EtOAc 8:1) gave azide 50 (188 mg, 46%) as a clear oil. See, e.g., Moriarty et al., 2001.

$R_f$=0.65 (hexane:EtOAc 4:1); $[\alpha]^{31}_D$=−13.14 (c 1.11, $CHCl_3$); IR (neat): $v_{max}$=2100, 1695, 1389, 1254, 1165 cm$^{-1}$; $^{13}$C NMR (100 MHz, DMSO-$d_6$, 353K) δ 153.0, 78.5, 62.7, 57.9, 57.0, 51.1, 31.7, 27.7, 25.3, 17.4, -5.8, -5.9; HRMS (ESI) calc. for $C_{16}H_{32}N_4O_3Si$ (M+H$^+$): 357.2322, found: 357.2318.

Synthesis 36

(2S,4S)-tert-Butyl 4-amino-2-((tert-butyl-dimethylsilyloxy)methyl)pyrrolidine-1-carboxylate (51)

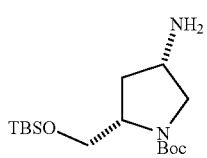

A solution of azide 50 (0.17 g, 0.477 mmol) in MeOH (2 mL) was added with stirring to a suspension of Pd/C (10% wt., 25 mg) in MeOH (1 mL) and the mixture was stirred for 2 h under an atmosphere of hydrogen. The flask was purged with $N_2$, the Pd/C filtered off and the filtrate was concentrated under reduced pressure. The crude product was filtered through a short plug of silica gel ($CHCl_3$:MeOH 9:1) to give amine 51 (128 mg, 81%) as a clear oil. See, e.g., Moriarty et al., 2001.

$R_f$=0.27 ($CHCl_3$:MeOH 9:1); $[\alpha]^{23}_D$=−27.1 (c 0.92, $CHCl_3$); IR (neat): $v_{max}$=3211, 1694, 1474, 1364, 1385, 1252 cm$^{-1}$; $^1$H NMR (400 MHz, DMSO-$d_6$, 353K) δ 3.75-3.67 (m, 3H), 3.43-3.52 (m, 2H), 2.99 (dd, J=10.9, 7.1 Hz, 1H), 2.25-2.31 (m, 1H), 1.76-1.85 (m, 1H), 1.40 (s, 9H), 0.89 (s, 9H), 0.05 (s, 6H); $^{13}$C NMR (100 MHz, DMSO-$d_6$, 353K) δ 153.0, 78.3, 63.3, 57.1, 51.9, 48.0, 34.3, 27.8, 17.5, -5.8; HRMS (ESI) calc. for $C_{16}H_{34}N_2O_3Si$ (M+H$^+$): 331.2417, found: 331.2413.

3.7—Synthesis of Piperidine 62

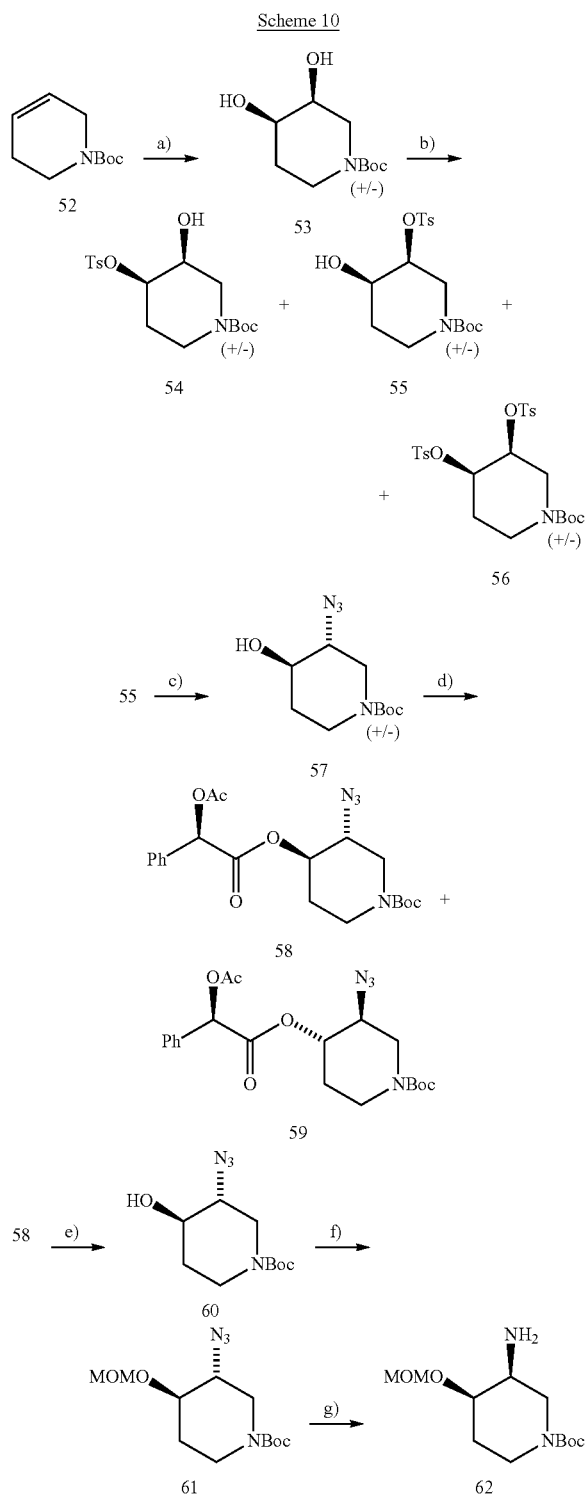

a) KOsO$_2$(OH)$_2$, THF/H$_2$O (4:1), 87%.
b) TsCl, Et$_3$N, CH$_2$Cl$_2$, 15% (54), 15% (55), 25% (56).
c) NaN$_3$, DMF, 60° C., 88%.
d) EDCI, DMAP, (R)-O-acetoxy-mandelic acid, CH$_2$Cl$_2$, 20% (58), 23% (59).
e) LiOH, THF/MeOH/H$_2$O (1:1:1), 99%.
f) MOMCl, iso-Pr$_2$NEt, CH$_2$Cl$_2$, 88%.
g) Pd/C, H$_2$, MeOH, 99%.

Synthesis 37 tert-Butyl 3,4-dihydroxypiperidine-1-carboxylate (53)

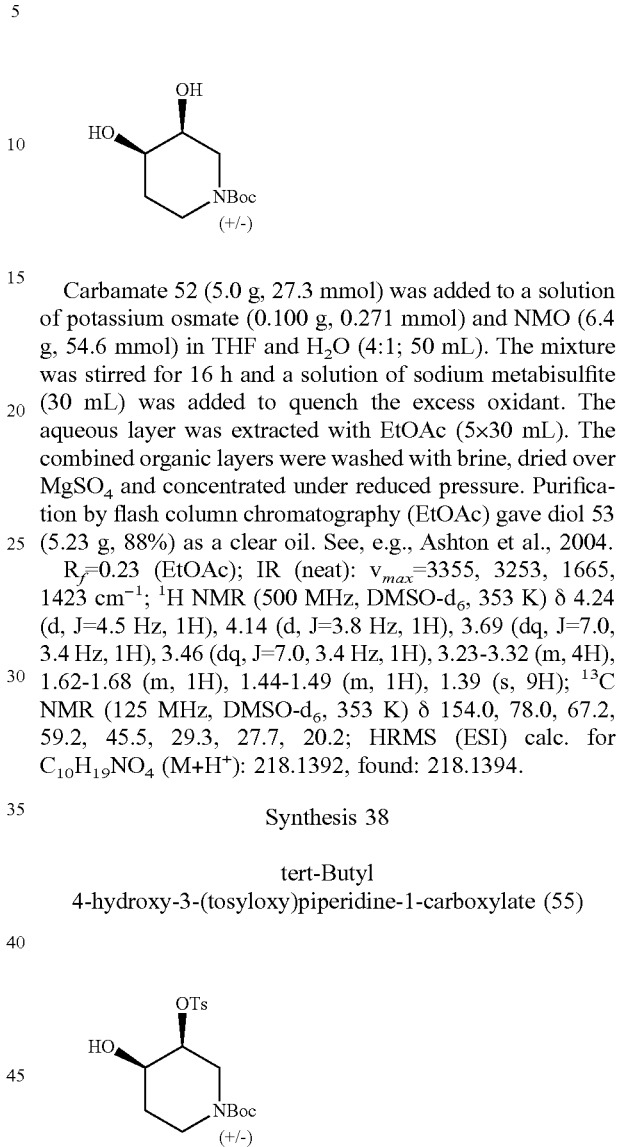

Carbamate 52 (5.0 g, 27.3 mmol) was added to a solution of potassium osmate (0.100 g, 0.271 mmol) and NMO (6.4 g, 54.6 mmol) in THF and H$_2$O (4:1; 50 mL). The mixture was stirred for 16 h and a solution of sodium metabisulfite (30 mL) was added to quench the excess oxidant. The aqueous layer was extracted with EtOAc (5×30 mL). The combined organic layers were washed with brine, dried over MgSO$_4$ and concentrated under reduced pressure. Purification by flash column chromatography (EtOAc) gave diol 53 (5.23 g, 88%) as a clear oil. See, e.g., Ashton et al., 2004.
R$_f$=0.23 (EtOAc); IR (neat): v$_{max}$=3355, 3253, 1665, 1423 cm$^{-1}$; $^1$H NMR (500 MHz, DMSO-d$_6$, 353 K) δ 4.24 (d, J=4.5 Hz, 1H), 4.14 (d, J=3.8 Hz, 1H), 3.69 (dq, J=7.0, 3.4 Hz, 1H), 3.46 (dq, J=7.0, 3.4 Hz, 1H), 3.23-3.32 (m, 4H), 1.62-1.68 (m, 1H), 1.44-1.49 (m, 1H), 1.39 (s, 9H); $^{13}$C NMR (125 MHz, DMSO-d$_6$, 353 K) δ 154.0, 78.0, 67.2, 59.2, 45.5, 29.3, 27.7, 20.2; HRMS (ESI) calc. for C$_{10}$H$_{19}$NO$_4$ (M+H$^+$): 218.1392, found: 218.1394.

Synthesis 38 tert-Butyl 4-hydroxy-3-(tosyloxy)piperidine-1-carboxylate (55)

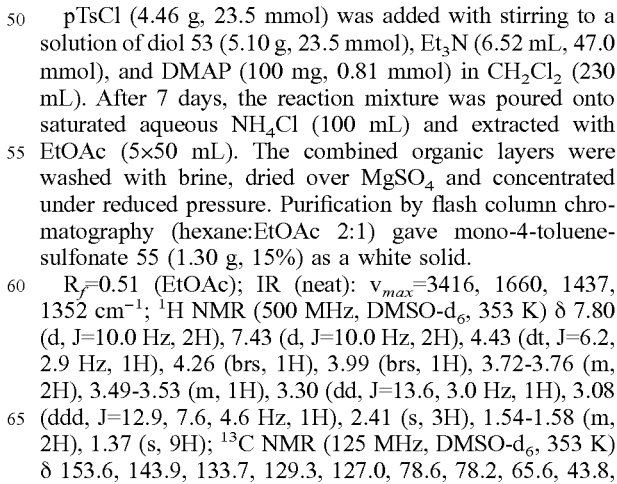

pTsCl (4.46 g, 23.5 mmol) was added with stirring to a solution of diol 53 (5.10 g, 23.5 mmol), Et$_3$N (6.52 mL, 47.0 mmol), and DMAP (100 mg, 0.81 mmol) in CH$_2$Cl$_2$ (230 mL). After 7 days, the reaction mixture was poured onto saturated aqueous NH$_4$Cl (100 mL) and extracted with EtOAc (5×50 mL). The combined organic layers were washed with brine, dried over MgSO$_4$ and concentrated under reduced pressure. Purification by flash column chromatography (hexane:EtOAc 2:1) gave mono-4-toluenesulfonate 55 (1.30 g, 15%) as a white solid.
R$_f$=0.51 (EtOAc); IR (neat): v$_{max}$=3416, 1660, 1437, 1352 cm$^{-1}$; $^1$H NMR (500 MHz, DMSO-d$_6$, 353 K) δ 7.80 (d, J=10.0 Hz, 2H), 7.43 (d, J=10.0 Hz, 2H), 4.43 (dt, J=6.2, 2.9 Hz, 1H), 4.26 (brs, 1H), 3.99 (brs, 1H), 3.72-3.76 (m, 2H), 3.49-3.53 (m, 1H), 3.30 (dd, J=13.6, 3.0 Hz, 1H), 3.08 (ddd, J=12.9, 7.6, 4.6 Hz, 1H), 2.41 (s, 3H), 1.54-1.58 (m, 2H), 1.37 (s, 9H); $^{13}$C NMR (125 MHz, DMSO-d$_6$, 353 K) δ 153.6, 143.9, 133.7, 129.3, 127.0, 78.6, 78.2, 65.6, 43.8, 29.2, 27.7, 20.5; HRMS (ESI) calc. for $C_{17}H_{25}NO_6S$ (M+Na$^+$): 394.1300, found: 394.1295.

Synthesis 39 tert-Butyl 3-azido-4-hydroxypiperidine-1-carboxylate (57)

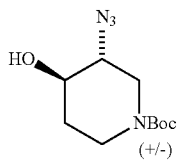
(+/-)

NaN$_3$ (1.11 g, 17.1 mmol) was added with stirring to a solution of 4-toluenesulfonate 55 (1.26 g, 3.41 mmol) in DMF (10 mL). After 3 days, the reaction mixture was poured onto water (20 mL) and extracted with EtOAc (4×20 mL). The combined organic layers were washed with brine, dried over MgSO$_4$ and concentrated under reduced pressure. Purification by flash column chromatography (EtOAc) gave azide 57 (730 g, 88%) as a clear oil.

$R_f$=0.29 (hexane:EtOAc 1:1); IR (neat): $v_{max}$=3427, 2103, 1666, 1420, 1366 cm$^{-1}$; $^1$H NMR (400 MHz, CDCl$_3$) δ 4.00 (dtd, J=13.7, 4.2, 1.8 Hz, 1H), 3.73 (t, J=6.2 Hz, 1H), 3.58 (brs, 1H), 3.28-3.32 (m, 1H), 2.83-2.87 (m, 1H), 2.64 (brs, 1H), 2.46 (t, J=6.2 Hz, 1H), 1.98 (dq, J=13.4, 3.8 Hz, 1H), 1.50 (s, 9H).

Synthesis 40

(3R,4R)-tert-Butyl 4-((R)-2-acetoxy-2-phenylacetoxy)-3-azidopiperidine-1-carboxylate (58)

(3S,4S)-tert-Butyl 4-((R)-2-acetoxy-2-phenylacetoxy)-3-azidopiperidine-1-carboxylate (59)

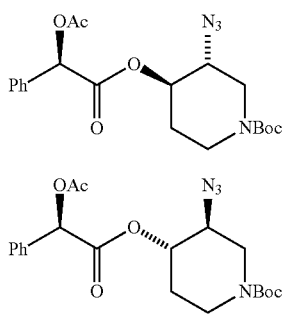

(R)—O-acetoxy-mandelic acid (0.795 g, 3.84 mmol), DMAP (31 mg, 0.256 mmol) and EDCl (0.733 g, 3.84 mmol) were added to a solution of azide 57 (0.620 g, 2.56 mmol) in CH$_2$Cl$_2$ (12 mL) and the reaction was stirred at ambient temperature. After 18 h the reaction mixture was poured on water (20 mL) and extracted with Et$_2$O (4×25 mL). The combined organic layers were washed with brine (20 mL), dried over MgSO$_4$, and concentrated under reduced pressure. The diastereoisomeric mixture was separated by preperative HPLC to afford ester 58 (218 mg, 20%) and ester 59 (250 mg, 23%) as clear oils.

58: $R_f$=0.38 (hexane:EtOAc 4:1); IR (neat): $v_{max}$=2105, 1742, 1692, 1420, 1366 cm$^{-1}$; $^1$H NMR (400 MHz, DMSO-d$_6$) δ 7.57-7.51 (m, 2H), 7.46-7.40 (m, 3H), 5.98 (s, 1H), 4.82 (td, J=7.9, 4.0 Hz, 1H), 3.90-3.65 (m, 2H), 3.35-3.00 (m, 3H), 2.16 (s, 3H), 1.81-1.73 (m, 1H), 1.40 (s, 9H), 1.32-1.21 (m, 1H); $^{13}$C NMR (100 MHz, DMSO-d$_6$) δ 170.4, 168.1, 154.0, 133.9, 129.7, 129.2, 128.1, 79.8, 74.5, 73.7, 72.8, 44.6, 28.3, 27.4, 20.7.

Synthesis 41

(3R,4R)-tert-Butyl 3-azido-4-hydroxy-piperidine-1-carboxylate (60)

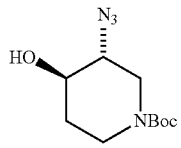

LiOH (55 mg, 1.3 mmol) was added to a solution of ester 58 in THF, H$_2$O and MeOH (1:1:1; 3 mL) and the mixture was stirred for 2 h. The reaction mixture was poured onto water (5 mL) and extracted with EtOAc (4×25 mL). The combined organic layers were washed with brine, dried over MgSO$_4$ and concentrated under reduced pressure. Purification by flash column chromatography (hexane:EtOAc 2:1) gave alcohol 60 as a clear oil (124 mg, 99%).

$R_f$=0.29 (hexane:EtOAc 1:1); IR (neat): $v_{max}$=3427, 2103, 1666, 1420, 1366 cm$^{-1}$; $^1$H NMR (400 MHz, CDCl$_3$) δ 4.00 (dtd, J=13.7, 4.2, 1.8 Hz, 1H), 3.73 (t, J=6.2 Hz, 1H), 3.58 (brs, 1H), 3.28-3.32 (m, 1H), 2.83-2.87 (m, 1H), 2.64 (brs, 1H), 2.46 (t, J=6.2 Hz, 1H), 1.98 (dq, J=13.4, 3.8 Hz, 1H), 1.50 (s, 9H); $^{13}$C NMR (100 MHz, CDCl$_3$) δ 154.4, 80.5, 72.0, 63.3, 45.3, 41.2, 32.0, 28.3.

Synthesis 42

(3R,4R)-tert-Butyl 3-azido-4-(methoxy-methoxy)piperidine-1-carboxylate (61)

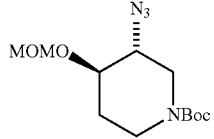

iso-Pr$_2$NEt (0.26 mL, 1.5 mmol) and MOMCl (0.075 mL, 1.0 mmol) were added with stirring to a solution of alcohol 60 (132 mg, 0.5 mmol) in CH$_2$Cl$_2$ (1 mL). After 18 h, additional iso-Pr$_2$NEt (0.26 mL, 1.5 mmol) and MOMCl (0.075 mL, 1.0 mmol) were added. After 24 h, saturated aqueous NaHCO$_3$ (5 mL) was added, the organic layer was separated and the aqueous layer was extracted with EtOAc (3×10 mL). The combined organic layers were washed with brine, dried over MgSO$_4$, and concentrated under reduced pressure. Purification by flash column chromatography (hexane:EtOAc 4:1) gave 61 (126 mg, 88%) as a clear oil.

$R_f$=0.47 (hexane:EtOAc 2:1); [α]$^{25}_D$=−9.7 (c 1.0, CHCl$_3$); IR (neat): $v_{max}$=2104, 1693, 1418, 1238, 1151 cm$^{-1}$; $^1$H NMR (500 MHz, CDCl$_3$) δ 4.75 (d, J=7.0 Hz, 1H), 4.73 (d, J=7.0 Hz, 1H), 4.08 (brs, 1H), 3.84 (dtd, J=13.7, 4.6, 1.7 Hz, 1H), 3.54 (ddd, J=11.6, 6.7, 2.3 Hz, 1H), 3.36-3.42 (m, 4H), 2.93 (brs, 2H), 2.02 (dtd, J=13.4, 4.7, 3.2 Hz, 1H), 1.47-1.53 (m, 1H), 1.45 (s, 9H); $^{13}$C NMR (CDCl$_3$, 125 MHz) δ 154.9, 95.5, 80.2, 61.0, 55.6, 45.4, 40.5, 30.1, 29.3, 28.4; HRMS (CI) calc. for $C_{12}H_{22}N_4O_4$ (M+H$^+$): 287.1719, found: 287.1725.

Synthesis 43

(3R,4R)-tert-Butyl 3-amino-4-(methoxy-methoxy)piperidine-1-carboxylate (62)

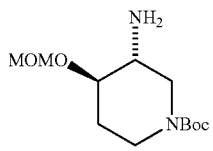

A solution of azide 61 (126 mg, 0.44 mmol) in MeOH (2 mL) was added to a suspension of Pd/C (15% wt., 50 mg) in methanol (1 mL). The reaction mixture was stirred under an atmosphere of hydrogen for 1 h, then filtered and concentrated under reduced pressure. Purification by flash column chromatography (CH$_2$Cl$_2$:MeOH 9:1) gave amine 62 (112 mg, 99%) as a clear oil.

$R_f$=0.25 (CH$_2$Cl$_2$:MeOH 9:1); [α]$^{25}_D$=+10.0 (c 1.0, CHCl$_3$); IR (neat): $v_{max}$=3376, 1689, 1421, 1241, 1165 cm$^{-1}$; $^1$H NMR (500 MHz, CDCl$_3$) δ 4.76 (d, J=6.9 Hz, 1H), 4.69 (d, J=6.9 Hz, 1H), 4.04 (s, 2H), 3.39 (s, 3H), 3.28-3.33 (m, 1H), 2.72-2.90 (m, 2H), 2.64 (t, J=11.7 Hz, 1H), 2.01 (ddd, J=9.5, 9.5, 5.0 Hz, 1H), 1.81 (s, 2H), 1.44-1.48 (m, 10H); $^{13}$C NMR (100 MHz, CDCl$_3$) δ 154.7, 95.7, 80.5, 79.8, 55.5, 52.4, 48.7, 42.1, 29.9, 28.4; HRMS (ESI) calc. for $C_{11}H_{24}N_2O_4$ (M+H$^+$): 261.1812, found: 261.1809.

4—Synthesis of the Target Compounds 4.1.1—General Procedure C Buchwald-Hartwig Coupling The heteroaryl chloride (0.50 mmol), Pd$_2$dba$_3$ (23.0 mg, 5 mol %), rac-BINAP (47.0 mg, 15 mol %), and NaOtBu (72.0 mg, 0.75 mmol), were suspended in toluene (1.8 mL). After 5 min of stirring, the pyrrolidine or piperidine (0.60 mmol) was added and the mixture heated for 16 h at 95° C. The reaction mixture was cooled to room temperature, filtered through celite and washed with EtOAc (10 mL) and poured onto brine (5 mL). The aqueous phase was extracted with ethyl acetate (3×10 mL) and the combined organic phases were dried over MgSO$_4$ and concentrated under reduced pressure. Purification by flash column chromatography (hexane:EtOAc) gave the corresponding product. See, e.g., Hong et al., 1997.

4.1.2—General Procedure D—Final Deprotection

The carbamate (0.15 mmol) was dissolved in MeOH and HCl (generated by treatment of MeOH (5 mL) with acetyl chloride (2.5 mL) at room temperature for 45 min) (5 M, 8 mL) and stirred at room temperature for 3 h. The solvent was removed under reduced pressure and the residue was purified by flash column chromatography (CH$_2$Cl$_2$:MeOH 9:1) to give the corresponding product.

4.2—Synthesis of PPDA-001

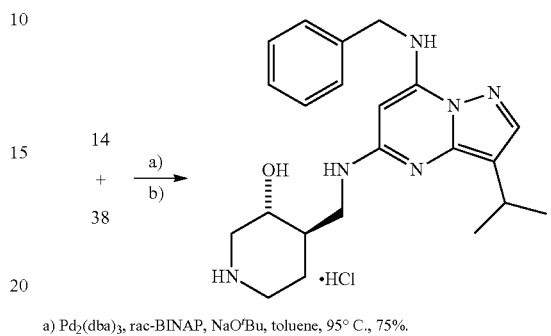

a) Pd$_2$(dba)$_3$, rac-BINAP, NaO$^t$Bu, toluene, 95° C., 75%.
b) 5M HCl/MeOH, 99%.

Synthesis 44

(3R,4R)-tert-butyl 4-(((7-(benzyl(tert-butoxycarbonyl)amino)-3-iso-propylpyrazolo[1,5-a]pyrimidin-5-yl)amino)methyl)-3-(methoxymethoxy)piperidine-1-carboxylate (63)

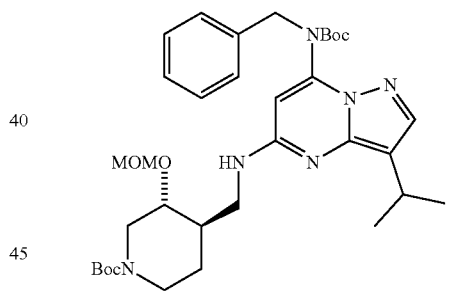

Following general procedure C, chloride 14 (1.28 g, 3.21 mmol), Pd$_2$dba$_3$ (147 mg, 0.160 mmol), rac-BINAP (300 mg, 0.480 mmol), sodium tert-butoxide (370 mg, 3.85 mmol) and amine 38 (870 mg, 3.21 mmol) were allowed to react in toluene (2 mL). Carbamate 63 was obtained as a pale yellow solid (1.48 g, 75%) after flash column chromatography (hexane:EtOAc 1:5).

$^1$H NMR δ (400 MHz, DMSO-d$_6$, 363 K) δ 7.65 (s, 1H), 7.26 (m, 5H), 6.69 (brt, J=5.4 Hz, 1H), 6.01 (s, 1H), 4.85 (s, 2H), 4.65 (d, J=6.5 Hz, 1H), 4.60 (d, J=6.5 Hz, 1H), 4.04 (m, 1H), 3.73 (dt, J=13.1, 4.2 Hz, 1H), 3.63 (dt, J=13.6, 5.6 Hz, 1H), 3.31 (m, 1H), 3.29 (s, 3H), 3.04 (sept, J=6.9 Hz, 1H), 2.77 (dd, J=12.9, 8.8 Hz, 1H), 1.79 (m, 2H), 1.41 (s, 9H), 1.34 (s, 9H), 1.30 (d, J=6.9 Hz, 6H), 1.24 (m, 1H); $^{13}$C NMR (100 MHz, DMSO-d$_6$, 363 K) δ 154.7, 153.4, 152.4, 145.4, 141.7, 140.0, 136.8, 127.5, 126.9, 126.5, 111.1, 96.7, 95.0, 80.5, 78.1, 74.0, 54.3, 50.7, 46.4, 41.8, 41.4, 40.4, 27.5, 27.1, 26.5, 22.8, 22.2.

Synthesis 45

(3R,4R)-4-(((7-(Benzylamino)-3-isopropylpyrazolo[1,5-a]pyrimidin-5-yl)amino)methyl)piperidin-3-ol hydrochloride (PPDA-001)

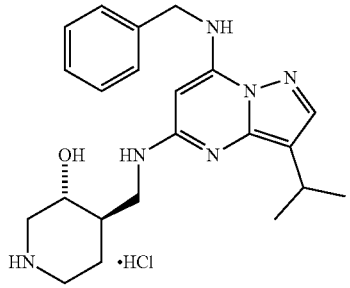 [SMILES: CC(C)c1cnn2c(NCc3ccccc3)cc(NC[C@H]3CCNC[C@@H]3O)nc12 ; Cl]

Following general procedure D, carbamates 63 (1.48 g, 2.41 mmol), was allowed to react with 5 M methanolic HCl. PPDA-001 was obtained as a white solid (1.04 g, 99%) after flash column chromatography (CH$_2$Cl$_2$:MeOH gradient 19:1 to 6:1).

$^1$H NMR (400 MHz, CD$_3$OD) δ 7.90 (s, 1H), 7.45 (d, J=7.2 Hz, 2H), 7.39 (t, J=7.7 Hz, 2H), 7.32 (t, J=7.2 Hz, 1H), 5.48 (s, 1H), 4.75 (brs, 2H), 3.73 (dt, J=10.2, 4.5 Hz, 1H), 3.60 (dd, J=14.1, 3.9 Hz, 1H), 3.50 (brs, 1H), 3.46 (dd, J=2.2, 4.2 Hz, 1H), 3.37 (dt, J=12.8, 2.8 Hz, 1H), 3.12 (sept, J=6.8 Hz, 1H), 2.96 (td, J=12.7, 2.9 Hz, 1H), 2.81 (dd, J=11.4, 11.1 Hz, 1H), 2.05 (m, 1H), 1.86 (m, 1H), 1.65 (m, 1H), 1.33 (d, J=6.8 Hz, 6H); $^{13}$C NMR (100 MHz, CD$_3$OD) δ 148.3, 142.2, 136.5, 128.6, 127.5, 127.0, 111.2, 65.3, 47.9, 45.3, 43.6, 43.0, 41.2, 24.5, 22.6, 22.2, 22.1.

4.3—Synthesis of PPDA-002

Scheme 12

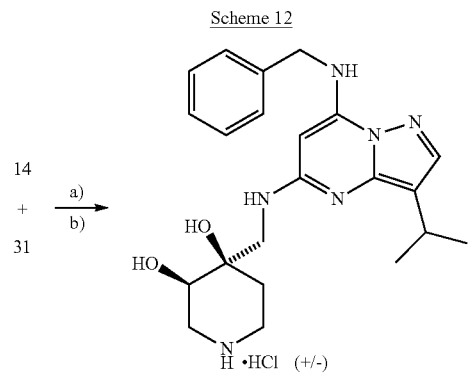

a) Pd$_2$(dba)$_3$, rac-BINAP, NaO$^t$Bu, toluene, 95° C., 41%.
b) 5M HCl/MeOH, 98%.

Synthesis 46

(3aR,7aR)-tert-Butyl 7a-((7-(benzyl(tert-butoxycarbonyl)amino)-3-iso-propyl-pyrazolo[1,5-a]pyrimidin-5-ylamino)methyl)-2,2-dimethyltetrahydro-[1,3]dioxolo[4,5-c]pyridine-5(6H)-carboxylate (64)

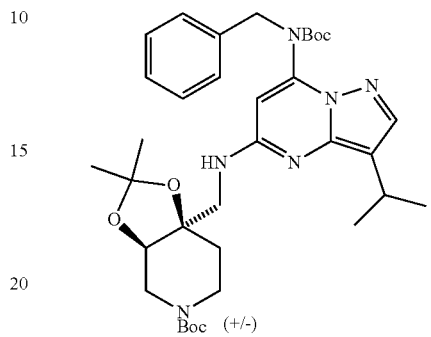

Following general procedure C, chloride 14 (89 mg, 0.22 mmol), Pd$_2$dba$_3$ (10 mg, 0.01 mmol), rac-BINAP (19 mg, 0.03 mmol), sodium tert-butoxide (53 mg, 0.55 mmol) and amine 31 (70 mg, 0.24 mmol) were allowed to react in toluene (2 mL). Carbamate 64 was obtained as a colorless oil (75 mg, 41%) after flash column chromatography (hexane: Et$_2$O gradient 7:3). The title compound (not analytically pure) was directly used for the next step.

Synthesis 47

(3R,4R)-4-((7-(Benzylamino)-3-iso-propyl-pyrazolo[1,5-a]pyrimidin-5-ylamino) methyl)piperidine-3,4-diol hydrochloride (PPDA-002)

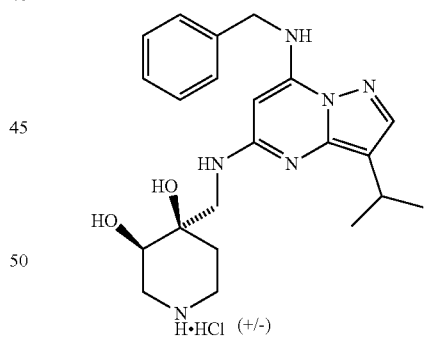

Following general procedure D, carbamate 64 (50 mg, 0.077 mmol), was allowed to react with 5 M methanolic HCl. PPDA-002 was obtained as a white solid (31 mg, 98%) after flash column chromatography (CH$_2$Cl$_2$:MeOH 4:1).

R$_f$=0.20 (CH$_2$Cl$_2$:MeOH 4:1); $^1$H NMR (CDCl$_3$, 400 MHz) δ 7.90 (s, 1H), 7.43-7.29 (m, 5H), 5.43 (s, 1H), 4.72 (s, 2H), 3.66 (td, J=10.3, 4.4 Hz, 1H), 3.59-3.54 (m, 1H), 3.48-3.34 (m, 3H), 3.07 (sept, J=6.9 Hz, 1H), 2.93 (td, J=12.6, 2.9 Hz, 1H), 2.77 (t, J=11.3 Hz, 1H), 2.05-2.00 (m, 1H), 1.86-1.78 (m, 1H), 1.63-1.53 (m, 1H), 1.31 (d, J=6.9 Hz, 6H); $^{13}$C NMR (100 MHz, CDCl$_3$) δ 156.6, 146.8, 145.3, 140.8, 136.9, 129.0, 128.0, 127.3, 112.9, 73.1, 71.5, 55.4, 53.5, 50.3, 46.1, 29.8, 23.9, 23.4.

4.4—Synthesis of PPDA-003

Scheme 13

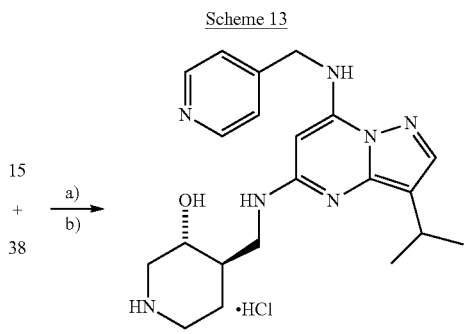

a) Pd$_2$(dba)$_3$, rac-BINAP, NaO$^t$Bu, toluene, 95° C., 66%.
b) 5M HCl/MeOH, 46%.

Synthesis 48

(3R,4R)-tert-Butyl 4-((7-(tert-butoxycarbonyl (pyridin-4-ylmethyl)amino)-3-iso-propyl pyrazolo[1,5-a]pyrimidin-5-ylamino)methyl)-3-(methoxymethoxy)piperidine-1-carboxylate (65)

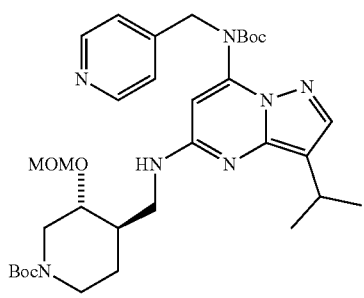

Following general procedure C, chloride 15 (91 mg, 0.22 mmol), Pd$_2$dba$_3$ (15 mg, 0.016 mmol), rac-BINAP (20 mg, 0.033 mmol), sodium tert-butoxide (32 mg, 0.33 mmol) and amine 38 (75 mg, 0.273 mmol) were allowed to react in toluene (1 mL). Carbamate 65 was obtained as a pale yellow solid (94 mg, 66%) after flash column chromatography (EtOAc).

R$_f$=0.30 (EtOAc); IR (neat): v$_{max}$=1692, 1643, 1523, 1154 cm$^{-1}$; $^1$H NMR (400 MHz, CDCl$_3$) δ 8.51 (d, J=6.0 Hz, 2H), 7.72 (s, 1H), 7.22 (d, J=6.0 Hz, 2H), 5.82 (s, 1H), 5.39 (t, J=5.9 Hz, 1H), 4.92 (s, 2H), 4.73 (d, J=6.8 Hz, 1H), 4.62 (d, J=6.8 Hz, 1H), 4.30 (brs, 1H), 4.02-3.90 (m, 1H), 3.69-3.63 (m, 1H), 3.49-3.40 (m, 1H), 3.37 (s, 3H), 3.36-3.29 (m, 1H), 3.10 (sept, J=6.9 Hz, 1H), 2.65 (t, J=12.8 Hz, 1H), 2.54 (s, 1H), 1.80-1.67 (m, 2H), 1.43 (s, 9H), 1.37 (s, 9H), 1.31 (d, J=6.9 Hz, 6H); $^{13}$C NMR (100 MHz, CDCl$_3$) δ 154.8, 154.5, 153.4, 149.8, 149.4, 147.0, 146.3, 142.5, 141.7, 128.5, 122.4, 113.4, 97.0, 96.1, 82.7, 79.8, 76.0, 60.4, 55.9, 50.7, 43.3, 42.3, 28.3, 28.0, 23.8, 23.1.

Synthesis 49

(3R,4R)-4-((3-iso-Propyl-7-(pyridin-4-ylmethylamino)pyrazolo[1,5-a]pyrimidin-5-ylamino)methyl)piperidin-3-ol hydrochloride (PPDA-003)

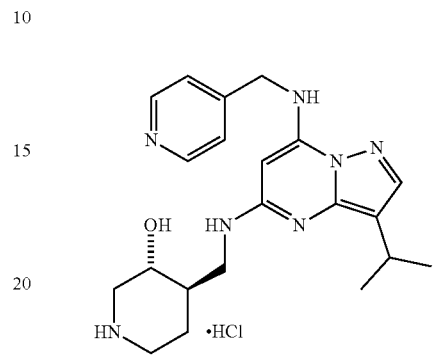

Following general procedure D, carbamate 65 (75 mg, 0.117 mmol), was allowed to react with 5 M methanolic HCl. PPDA-004 was obtained as a white solid (23 mg, 46%) after flash column chromatography (CH$_2$Cl$_2$:MeOH gradient 19:1 to 9:1).

R$_f$=0.20 (CHCl$_3$:MeOH 5:1); IR (neat): v$_{max}$=3278, 1717, 1643, 1584, 1156 cm$^{-1}$; $^1$H NMR (500 MHz, CD$_3$OD) δ 8.85 (d, J=6.2 Hz, 2H), 8.12 (d, J=6.1 Hz, 2H), 5.15 (s, 2H), 3.68 (td, J=10.1, 4.4 Hz, 1H), 3.58 (d, J=11.5 Hz, 1H), 3.53-3.42 (m, 1H), 3.40-3.32 (m, 2H), 3.16-3.07 (m, 1H), 2.96 (t, J=10.5 Hz, 1H), 2.76 (t, J=11.3 Hz, 1H), 2.66 (s, 3H), 2.08 (d, J=14.5 Hz, 1H), 1.85 (brs, 1H), 1.70-1.59 (m, 1H), 1.32 (d, J=6.9 Hz, 6H); $^{13}$C NMR (100 MHz, CD$_3$OD, 353 K) δ 160.3, 155.2, 151.1, 144.1, 142.9, 135.0, 126.6, 112.7, 66.7, 45.9, 45.3, 44.3, 42.4, 40.5, 25.9, 24.0, 23.5.

4.5—Synthesis of PPDA-007

Scheme 14

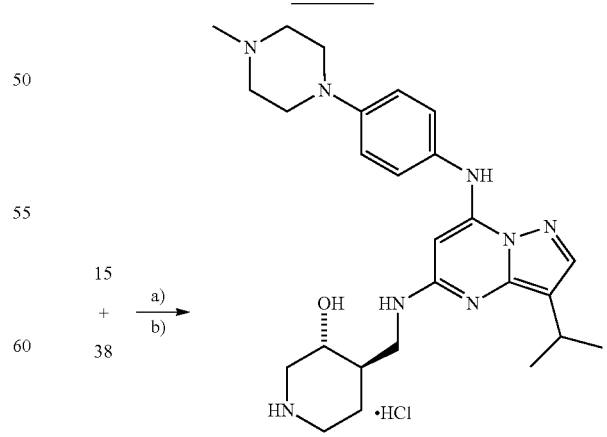

a) Pd$_2$(dba)$_3$, rac-BINAP, NaO$^t$Bu, toluene, 95° C., 48%.
b) 5M HCl/MeOH, 80%.

Synthesis 50

(3R,4R)-tert-Butyl 4-((7-(tert-butoxycarbonyl (4-(4-methylpiperazin-1-yl)phenyl)amino)-3-iso-propylpyrazolo[1,5-a]pyrimidin-5-ylamino)methyl)-3-(methoxymethoxy) piperidine-1-carboxylate (66)

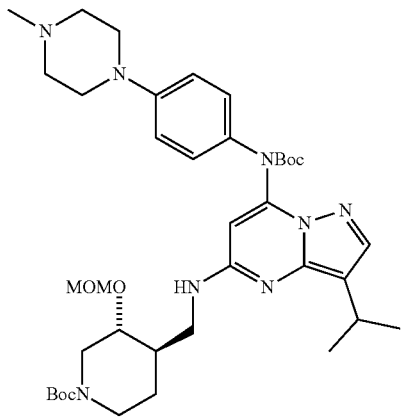

Following general procedure C, chloride 16 (100 mg, 0.20 mmol), Pd$_2$dba$_3$ (13 mg, 0.014 mmol), rac-BINAP (17 mg, 0.028 mmol), sodium tert-butoxide (29 mg, 0.30 mmol) and amine 38 (55 mg, 0.20 mmol) were allowed to react in toluene (2 mL). Carbamate 66 was obtained as a white solid (69 mg, 48%) after flash column chromatography (CH$_2$Cl$_2$: MeOH 20:1).

R$_f$=0.46 (20:1 CH$_2$Cl$_2$/MeOH); [α]$_D^{23}$+20.3 (c 1.0, CHCl$_3$); IR (neat): ν$_{max}$=3370, 1698, 1643, 1515, 1157 cm$^{-1}$; HRMS (ESI) Calcd. for O$_{38}$H$_{58}$N$_8$O$_6$ [M+H]$^+$, 723.4558, found 723.4548.

Synthesis 51

(3R,4R)-4-((3-iso-Propyl-7-(4-(4-methylpiperazin-1-yl)phenylamino)pyrazolo[1,5-a]pyrimidin-5-ylamino)methyl)piperidin-3-ol hydrochloride (PPDA-007)

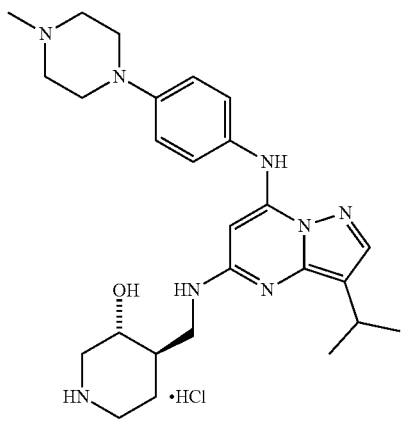 [SMILES: CC(C)c1cnn2c(Nc3ccc(N4CCN(C)CC4)cc3)cc(NC[C@H]3CCNC[C@@H]3O)nc12 ; Cl]

Following general procedure D, carbamate 66 (40 mg, 0.055 mmol), was allowed to react with 5 M methanolic HCl. PPDA-008 was obtained as a white solid (22 mg, 80%) after HPLC (water:acetonitrile gradient 95:5 to 40:60).

IR (neat): ν$_{max}$=3246, 2474, 1659, 1575 cm$^{-1}$; $^{13}$C NMR (CD$_3$OD, 125 MHz) δ 150.4, 148.8, 143.9, 137.9, 135.1, 130.0, 128.9, 127.9, 118.9, 115.7, 103.9, 66.7, 57.0, 54.6, 46.6, 44.9, 44.4, 43.6, 42.6, 40.4, 34.6, 27.4, 26.1, 25.7, 23.8, 23.6.

4.6—Synthesis of PPDA-009

Scheme 15

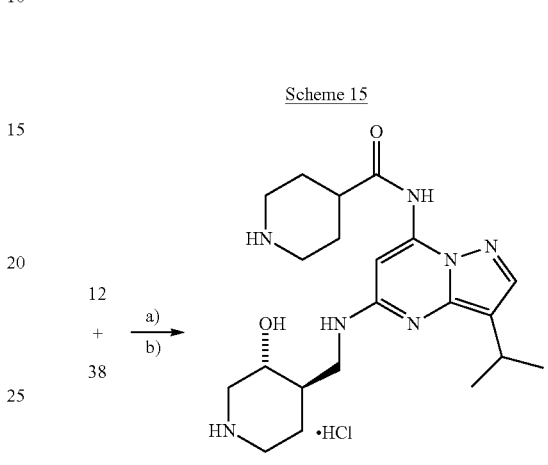

a) Pd$_2$(dba)$_3$, rac-BINAP, NaO$^t$Bu, toluene, 95° C., 61%.
b) 5M HCl/MeOH, 90%.

Synthesis 52

(3R,4R)-tert-Butyl 4-(((7-(1-(tert-butoxycarbonyl) piperidine-4-carboxamido)-3-iso-propylpyrazolo[1,5-a]pyrimidin-5-yl)amino)methyl)-3-(methoxymethoxy) piperidine-1-carboxylate (67)

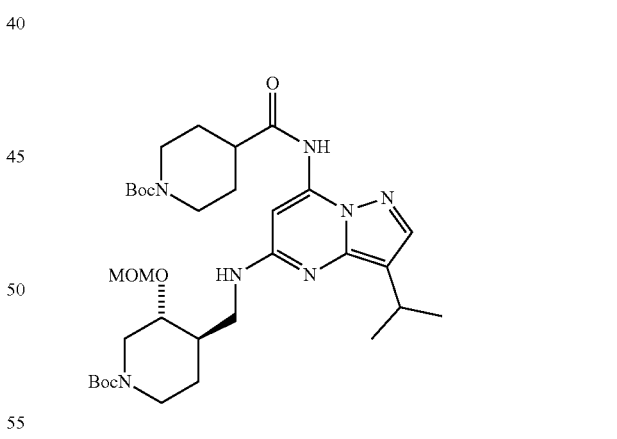

Following general procedure C, chloride 12 (230 mg, 0.546 mmol), Pd$_2$dba$_3$ (50 mg, 0.054 mmol), rac-BINAP (50 mg, 0.10 mmol), sodium tert-butoxide (61 mg, 0.82 mmol) and amine 38 (171 mg, 0.624 mmol) were allowed to react in toluene (2 mL). Carbamate 67 was obtained as a pale yellow solid (220 mg, 61%) after flash column chromatography (hexane:EtOAc 7:3).

$^1$H NMR (400 MHz, CDCl$_3$) δ 9.14 (s, 1H), 7.66 (s, 1H), 6.93 (s, 1H), 5.25 (brs, 1H), 4.82 (d, J=6.8 Hz, 1H), 4.69 (d, J=6.8 Hz, 1H), 4.23 (brs, 3H), 4.04 (brs, 1H), 3.75-3.64 (m, 1H), 3.64-3.51 (m, 1H), 3.49-3.33 (m, 4H), 3.13 (quin, J=6.8

Hz, 1H), 2.92-2.78 (m, 2H), 2.78-2.51 (m, 3H), 1.98 (d, J=11.7 Hz, 2H), 1.87-1.69 (m, 4H), 1.52-1.46 (m, 18H), 1.35 (d, J=6.8 Hz, 6H).

Synthesis 53

N-(5-((((3R,4R)-3-Hydroxypiperidin-4-yl)methyl) amino)-3-iso-propylpyrazolo[1,5-a]pyrimidin-7-yl) piperidine-4-carboxamide hydrochloride (PPDA-009)

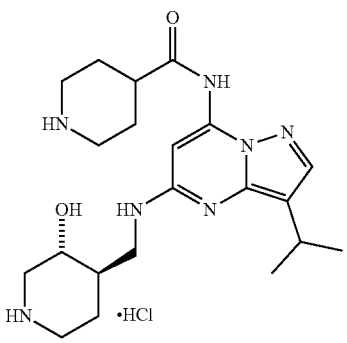 [SMILES: CC(C)c1cnn2c(NC(=O)C3CCNCC3)cc(NC[C@H]3CCNC[C@@H]3O)nc12 ; Cl]

Following general procedure D, carbamate 67 (100 mg, 0.15 mmol), was allowed to react with 5 M methanolic HCl. PPDA-010 was obtained as a white solid (64 mg, 90%) after flash column chromatography (CH$_2$Cl$_2$:MeOH gradient 10:0 to 85:15).

IR (neat): $v_{max}$=3284, 1730, 1639, 1584 cm$^{-1}$; $^1$H NMR (400 MHz, MeOD-d$_4$) δ 7.98 (brs, 1H), 7.39 (brs, 1H), 3.73 (d, J=8.3 Hz, 2H), 3.57-3.35 (m, 4H), 3.26-2.97 (m, 5H), 2.86 (t, J=10.8 Hz, 1H), 2.26-2.16 (m, 3H), 2.13 (brs, 1H), 2.07-1.91 (m, 3H), 1.73 (brs, 1H), 1.33 (d, J=6.4 Hz, 6H).

4.7—Synthesis of PPDA-010

Scheme 16

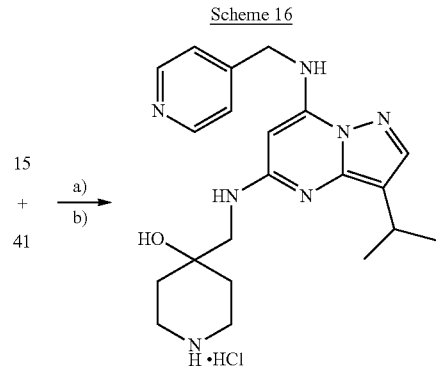

a) Pd$_2$(dba)$_3$, rac-BINAP, NaO$^t$Bu, toluene, 95° C., 28%.
b) 5M HCl/MeOH, 70% (2 steps).

Synthesis 54 tert-Butyl 4-(((7-((tert-butoxycarbonyl) (pyridin-4-ylmethyl)amino)-3-iso-propylpyrazolo[1,5-a]pyrimidin-5-yl)amino)methyl)-4-((triethylsilyl)oxy)piperidine-1-carboxylate (68)

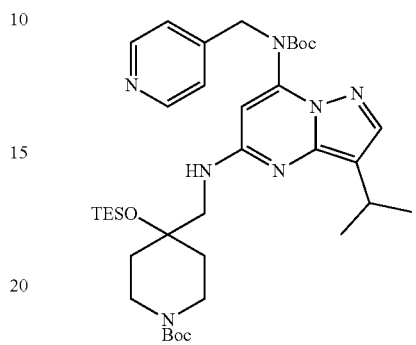

Following general procedure C, chloride 15 (1.182 g, 2.94 mmol), Pd$_2$dba$_3$ (119 mg, 0.13 mmol), rac-BINAP (249 mg, 0.40 mmol), sodium tert-butoxide (385 mg, 4.01 mmol) and 40 (920 mg, 2.67 mmol) were allowed to react in toluene (2 mL). Carbamate 68 was obtained as a pale yellow solid (531 mg, 28%) after flash column chromatography (hexane:EtOAc 1:5).

R$_f$=0.5 (EtOAc); HRMS (ESI) calc. for C$_{37}$H$_{60}$N$_7$O$_5$Si (M+H$^+$): 710.4425, found: 710.4456.

Synthesis 55

4-(((3-iso-Propyl-7-((pyridin-4-ylmethyl)amino) pyrazolo[1,5-a]pyrimidin-5-yl)amino)methyl)piperidin-4-ol hydrochloride (PPDA-010)

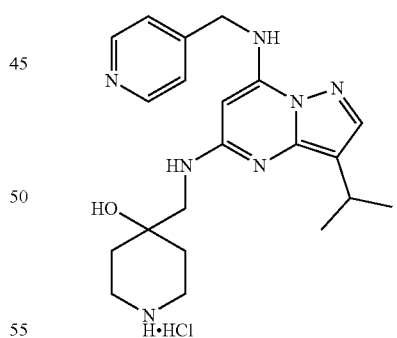

Following general procedure D, carbamate 68 (500 mg, 0.70 mmol), was allowed to react with 5 M methanolic HCl. PPDA-011 was obtained as a white solid (195 mg, 70%) after flash column chromatography (CH$_2$Cl$_2$:MeOH gradient 19:1 to 6:1).

R$_f$=0.4 (CHCl$_3$:MeOH 9:1); IR (neat): $v_{max}$=3321, 1728, 1660, 1584, 1460, 1384, 1290, 1272, 1123 cm$^{-1}$; $^1$H NMR (CD$_3$OD, 500 MHz) δ 8.80 (2H, d, J=10.0 Hz), 8.05 (2H, d, J=10.0 Hz), 7.93 (1H, s), 7.72-7.70 (1H, m), 7.62-7.61 (1H, m), 5.15 (2H, br s), 4.20 (1H, m), 3.51 (2H, s), 3.27-3.24

(4H, m), 3.11 (1H, m), 1.88 (5H, m), 1.33 (6H, d, J=10.0 Hz); HRMS (ESI) calc. for $C_{21}H_{30}N_{70}$ (M+H⁺): 396.2512, found: 396.2504.

4.8—Synthesis of PPDA-015

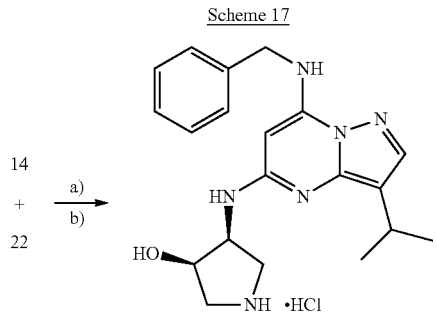

a) Pd₂(dba)₃, rac-BINAP, NaO'Bu, toluene, 95° C., 85%.
b) 5M HCl/MeOH, 95%.

Synthesis 56 tert-Butyl-5-((3S,4S)-1-(tert-butoxycarbonyl)-4-(methoxymethoxy)pyrrolidin-3-ylamino)-3-iso-propylpyrazolo[1,5-a]pyrimidin-7-ylbenzylcarbamate (69)

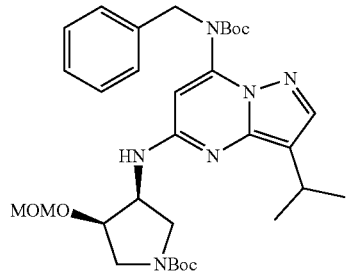

Following general procedure C, chloride 14 (110 mg, 0.28 mmol), Pd₂dba₃ (13 mg, 0.014 mmol), rac-BINAP (427 mg, 0.042 mmol), sodium tert-butoxide (36 mg, 0.37 mmol) and 22 (89 mg, 0.36 mmol) were allowed to react in toluene (3 mL). Carbamate 69 was obtained as an orange oil (145 mg, 85%) after flash column chromatography (hexane:Et₂O 7:3).

$R_f$=0.36 (Et₂O:hexane:30% aqueous ammonia 71.75:28: 0.25); $[α]^{20}_D$=+33 (c 0.58, CH₂Cl₂); ¹H NMR (400 MHz, CDCl₃) δ 7.76 (s, 1H), 7.23-7.30 (m, 5H), 5.76 (s, 1H), 5.29 (d, J=7.2 Hz, 0.6H rotamers), 5.24 (d, J=7.2 Hz, 0.4H rotamers), 4.94 (br s, 2H), 4.67 (t, J=10.4 Hz, 1H), 4.55-4.63 (m, 2H), 4.27 (br s, 1H), 3.83-3.91 (m, 1H), 3.51-3.63 (m, 2H), 3.28 (s, 1.7H rotamers), 3.27 (s, 1.3H rotamers), 3.12-3.23 (m, 2H), 1.47 (s, 3.7H rotamers), 1.45 (s, 5.3H rotamers), 1.40 (br s, 9H), 1.33 (d, J=6.8 Hz, 6H); ¹³C NMR (100 MHz, CDCl₃) δ 154.6, 153.8, 146.1, 142.9, 141.6, 137.7, 128.5, 127.9, 127.5, 113.8, 97.5, 96.0, 82.2, 79.6, 77.4, 75.7, 55.7, 52.5, 51.4, 50.5, 48.8, 28.5, 28.1, 23.9, 23.7; HRMS (ESI) calc. for $C_{32}H_{46}N_{56}O_6$ (M+H⁺): 611.3557, found 611.3543.

Synthesis 57

(3S,4S)-4-(7-(Benzylamino)-3-iso-propyl-pyrazolo [1,5-a]pyrimidin-5-ylamino)-pyrrolidin-3-ol hydrochloride (PPDA-015)

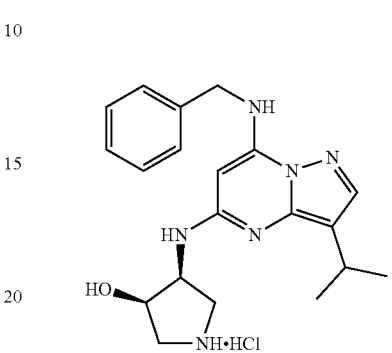

Following general procedure D, carbamate 69 (140 mg, 0.23 mmol), was allowed to react with 5M methanolic HCl. PPDA-016 was obtained as a pale orange solid (80 mg, 95%) after flash column chromatography (CH₂Cl₂: MeOH 4:1).

$R_f$=0.32 (CH₂Cl₂:MeOH:30% aqueous ammonia 80:19.5: 0.5); $[α]^{20}_D$=+12 (c 1.0, MeOH); m.p.=102° C.; ¹H NMR (400 MHz, CDCl₃) δ 7.65 (s, 1H), 7.30 (brs, 5H), 6.59 (brs, 1H), 5.58 (d, J=4.8 Hz, 1H), 5.1 (s, 1H), 4.62 (brs, 2H), 4.33-4.37 (m, 3H), 4.26-4.31 (m, 1H), 3.33 (dd, J=11.2, 8.0 Hz, 1H), 3.15 (dd, J=12.0, 4.0 Hz, 1H), 3.03-3.11 (m, 2H), 2.85 (dd, J=10.2, 7.2 Hz, 1H), 1.30 (d, J=6.8 Hz, 6H); ¹³C NMR (100 MHz, CDCl₃) δ 156.6, 146.8, 145.3, 140.8, 136.9, 129.0, 128.0, 127.3, 112.9, 73.1, 71.5, 55.4, 53.5, 50.3, 46.1, 29.8, 23.9, 23.4; HRMS (ESI) calc. for $C_{20}H_{26}N_6O$ (M+H⁺): 367.2246, found 367.2239; Anal. calc. for $C_{20}H_{27}ClN_6O$: C, 65.55, H, 7.15, N, 22.93, found: C, 65.54, H, 7.09, N, 22.87.

4.9—Synthesis of PPDA-018

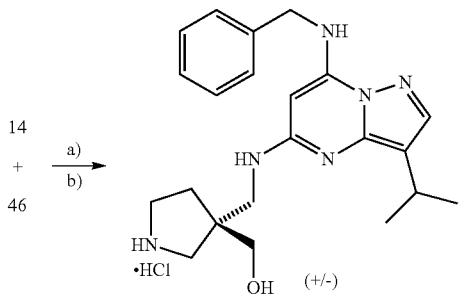

a) Pd₂(dba)₃, rac-BINAP, NaO'Bu, toluene, 95° C., 65%.
b) 5M HCl/MeOH, 80%.

Synthesis 58 tert-Butyl 3-((7-(benzyl(tert-butoxycarbonyl)amino)-3-iso-propylpyrazolo[1,5-a]pyrimidin-5-ylamino)methyl)-3-((methoxymethoxy) methyl)pyrrolidine-1-carboxylate (70)

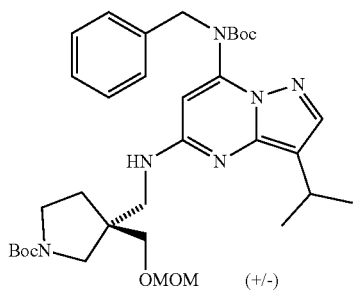

Following general procedure C, chloride 14 (879 mg, 2.2 mmol), Pd$_2$dba$_3$ (133 mg, 0.14 mmol) rac-BINAP (220 mg, 0.35 mmol), sodium tert-butoxide (220 mg, 2.3 mmol) and amine 46 (400 mg, 1.5 mmol) were allowed to react in toluene (15 mL). Carbamate 70 was obtained as a pale yellow solid (600 mg, 65%) after flash column chromatography (hexane:EtOAc gradient 19:1 to 7:3).

$^1$H NMR (400 MHz, CDCl$_3$) δ 7.75 (s, 1H), 7.30 (m, 5H), 7.22 (m, 1H), 5.66 (m, 1H), 5.03 (m, 3H), 4.60 (s, 2H), 3.50-3.25 (m, 10H), 3.12 (td, J=13.8, 6.9 Hz, 1H), 1.76 (m, 2H), 1.45 (d, J=9.3 Hz, 9H), 1.40 (s, 9H), 1.32 (d, J=6.8 Hz, 6H); MS (ESI): m/z 639.4 (M+H$^+$).

Synthesis 59

(3-((7-(Benzylamino)-3-iso-propylpyrazolo[1,5-a]pyrimidin-5ylamino)methyl)pyrrolidin-3-yl)methanol hydrochloride (PPDA-018)

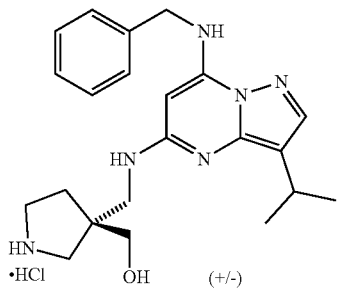 [SMILES: CC(C)c1cnn2c(NCc3ccccc3)cc(NC[C@@]3(CO)CCNC3)nc12 ; Cl ; "(+/-)"]

Following general procedure D, carbamate 70 (600 mg, 10.94 mmol), was allowed to react with 5 M methanolic HCl. PPDA-019 was obtained as a white solid (320 mg, 80%) after flash column chromatography (CH$_2$Cl$_2$:MeOH gradient 19:1 to 9:1).

IR (neat): ν$_{max}$=3274, 1663, 1577 cm$^{-1}$; $^1$H NMR (400 MHz, CD$_3$OD) δ 7.68 (s, 1H), 7.33 (m, 5H), 5.20 (s, 1H), 4.55 (s, 2H), 3.44 (m, 6H), 3.17 (q, J=12.2 Hz, 2H), 3.03 (m, 1H), 1.92 (m, 2H), 1.29 (dd, J=6.9, 3.9 Hz, 6H); $^{13}$C NMR (100 MHz, CD$_3$OD) δ 148.5, 141.7, 139.1, 129.8, 128.6, 128.1, 113.6, 73.8, 64.8, 51.9, 50.9, 46.6, 46.2, 44.9, 31.6, 24.7, 23.9, 23.8; HRMS (ESI) calc. for C$_{22}$H$_{30}$N$_6$O (M+H$^+$): 395.2481, found: 395.2534.

4.10—Synthesis of PPDA-022

Scheme 19

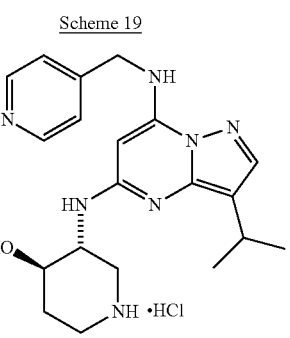

a) Pd$_2$(dba)$_3$, rac-BINAP, NaO$^t$Bu, toluene, 95° C., 30%.
b) 5M HCl/MeOH, 76%.

Synthesis 60

(3R,4R)-tert-Butyl 3-(7-(benzyl(tert-butoxy-carbonyl)amino)-3-iso-propylpyrazolo[1,5-a]pyrimidin-5-ylamino)-4 (methoxymethoxy) piperidine-1-carboxylate (71)

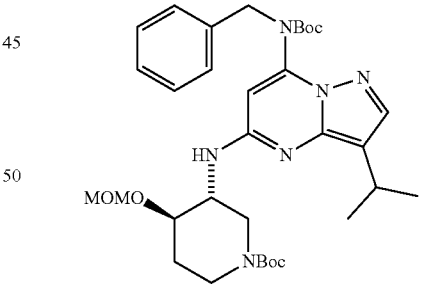

Following general procedure C, chloride 14 (72 mg, 0.18 mmol), Pd$_2$dba$_3$ (8 mg, 0.009 mmol), rac-BINAP (12 mg, 0.018 mmol), sodium tert-butoxide (26 mg, 0.27 mmol) and amine 62 (47 mg, 0.18 mmol) were allowed to react in toluene (1 mL). Carbamate 71 was obtained as a pale yellow oil (32 mg, 30%) after flash column chromatography (hexane:EtOAc 6:1).

R$_f$=0.3 (hexane:EtOAc 2:1); [α]$^{25}_D$=+1.0 (c 1.11, CHCl$_3$); IR (neat): ν$_{max}$=3347, 1719, 1670, 1640, 1366, 1153 cm$^{-1}$; HRMS (ESI) calc. for C$_{33}$H$_{48}$N$_6$O$_6$ (M+H$^+$): 625.3714, found: 625.3708.

Synthesis 61

(3R,4R)-3-(7-(Benzylamino)-3-iso-propyl-pyrazolo[1,5-a]pyrimidin-5-ylamino) piperidin-4-ol (PPDA-022)

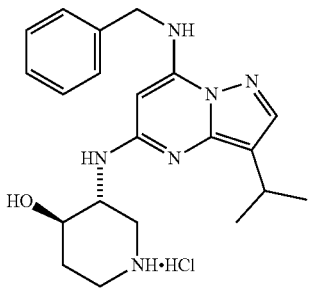

Following general procedure D, carbamate 71 (32 mg, 0.05 mmol), was treated with 5 M methanolic HCl. PPDA-023 was obtained as a white solid (16.2 mg, 76%) after flash column chromatography (CH$_2$Cl$_2$:MeOH 9:1).

$R_f$=0.13 (CHCl$_3$:MeOH 5:1); IR (neat): $v_{max}$=3294, 1626, 1569, 1450 cm$^{-1}$; $^1$H NMR (500 MHz, CD$_3$OD) δ 7.74 (s, 1H), 7.39 (d, J=7.6 Hz, 2H), 7.33 (tt, J=7.7, 1.5 Hz, 2H), 7.24-7.26 (m, 1H), 4.61 (s, 2H), 4.09 (dt, J=10.2, 5.0 Hz, 1H), 3.84 (td, J=9.2, 3.8 Hz, 1H), 3.57-3.61 (m, 2H), 3.40 (dt, J=12.8, 4.5 Hz, 1H), 3.09 (ddt, J=13.5, 11.1, 3.0 Hz, 3H), 2.21-2.27 (m, 1H), 1.83 (dd, J=18.7, 7.9 Hz, 1H), 1.31 (d, J=6 Hz, 3H), 1.29 (d, J=6 Hz, 3H); $^{13}$C NMR (125 MHz, CD$_3$OD) δ 156.9, 149.2, 144.1, 138.6, 129.8, 129.0, 128.7, 113.5, 69.0, 67.6, 53.4, 47.5, 46.6, 42.9, 30.3, 28.3, 24.6, 23.7; HRMS (ESI) calc. for C$_{21}$H$_{28}$N$_6$O (M+H$^+$): 381.2403, found: 381.2400.

4.11—Synthesis of PPDA-026

Scheme 20

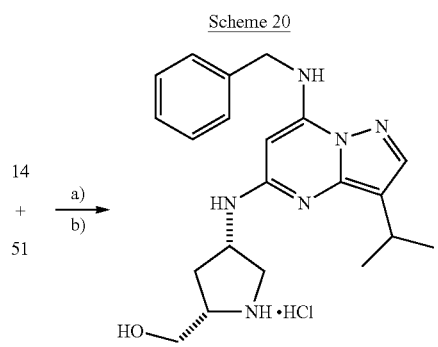

a) Pd$_2$(dba)$_3$, rac-BINAP, NaO$^t$Bu, toluene, 95° C., 59%.
b) 5M HCl/MeOH, 85%.

Synthesis 62

(2S,4S)-tert-Butyl 4-(7-(benzyl(tert-butoxy-carbonyl)amino)-3-iso-propylpyrazolo[1,5-a]pyrimidin-5-ylamino)-2-((tert-butyl dimethylsilyloxy)methyl)pyrrolidine-1-carboxylate (72)

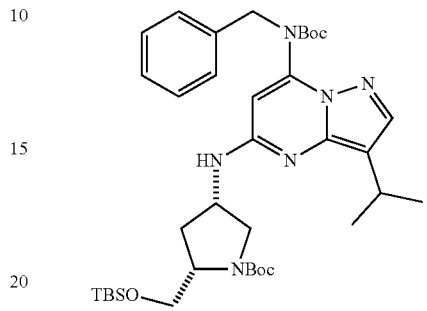

Following general procedure C, chloride 14 (45.1 mg, 0.112 mmol), Pd$_2$dba$_3$ (5 mg, 0.0056 mmol), rac-BINAP (8 mg, 0.011 mmol), sodium tert-butoxide (16.1 mg, 0.168 mmol) and amine 51 (44.7 mg, 0.135 mmol) were allowed to react in toluene (2 mL). Carbamate 72 was obtained as a pale yellow solid (45.5 mg, 59%) after flash column chromatography (hexane:EtOAc 4:1).

$R_f$=0.55 (hexane:EtOAc 2:1); $[α]^{24}_D$=−72.4 (c 1.7, CHCl$_3$); IR (neat): $v_{max}$=3343, 1692, 1641, 1518, 1390, 1366, 1252, 1157 cm$^{-1}$; $^1$H NMR (400 MHz, CDCl$_3$) δ 7.77 (s, 1H), 7.24-7.36 (m, 5H), 5.96-5.98 (m, 1H), 5.70 (s, 2H), 4.64 (s, 1H), 4.23-4.26 (m, 1H), 3.78-4.01 (m, 2H), 3.60-3.67 (m, 1H), 3.80-3.27 (m, 1H), 3.14 (sept, J=8.0 Hz, 1H), 2.43-2.51 (m, 1H), 1.88 (d, J=16.0 Hz, 1H), 1.47 (s, 9H), 1.43 (s, 9H), 1.36 (d, J=8.0 Hz, 6H), 0.9 (s, 9H), 0.09 (s, 3H), 0.06 (s, 3H); HRMS (ESI) calc. for C$_{37}$H$_{58}$N$_6$O$_5$Si (M+H$^+$): 695.4316, found: 695.4330.

Synthesis 63

((2S,4S)-4-(7-(Benzylamino)-3-iso-propyl pyrazolo[1,5-a]pyrimidin-5-ylamino) pyrrolidin-2-yl)methanol hydrochloride (PPDA-026)

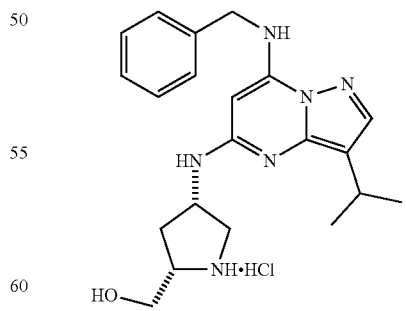

Following general procedure D, carbamate 72 (37.5 mg, 0.054 mmol), was allowed to react with 5M methanolic HCl. PPDA-027 was obtained as a yellow solid (20.9 mg, 85%) after flash column chromatography (CH$_2$Cl$_2$:MeOH gradient 9:1 to 5:1).

$R_f$=0.22 (CHCl$_3$:MeOH 9:1); [α]$^{27}_D$=−12.6 (c 0.80, MeOH); IR (neat): ν$_{max}$=3235, 1654, 1576 cm$^{-1}$; HRMS (ESI) calc. for C$_{21}$H$_{28}$N$_6$O (M+H$^+$): 381.2403, found: 381.2398.

5—Optimised Synthesis of PPDA-001

Scheme 21

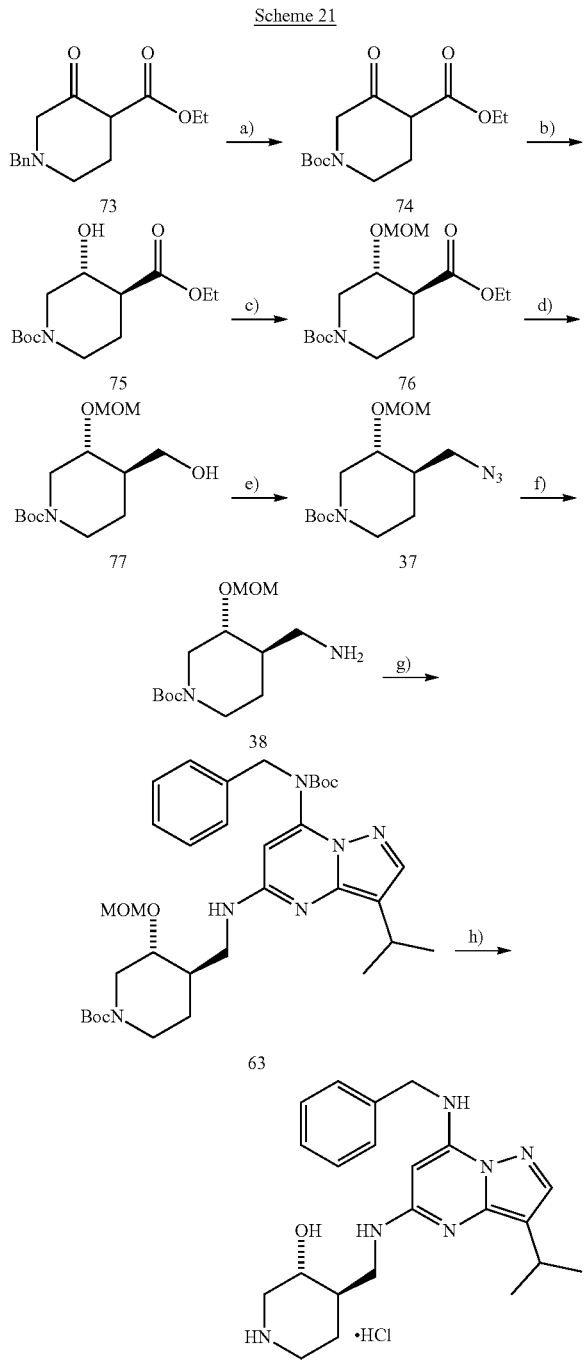

a) Pd/C, H$_2$ (38 bar), Boc$_2$O, Na$_2$CO$_3$, EtOH 99%.
b) [RuCl(cymene)((S)-T-BINAP)]Cl, H$_2$ (10 bar), CH$_2$Cl$_2$, 50° C., 48 h, 77% (97:3) er).
c) MOMCl, DIPEA, CH$_2$Cl$_2$, 75%.
d) DIBAL-H, CH$_2$Cl$_2$, −20° C., 77%.
e) MsCl, DIPEA, CH$_2$Cl$_2$ then NaN$_3$, NaI, DMF, 78%.
f) Pd/C, H$_2$ (20 bar), MeOH, 95%.
g) 14, Pd$_2$(dba)$_3$, rac-BINAP, NaO$^t$Bu, toluene, 95% °C., 75%.
h) 5M HCl/MeOH, 99%.

Synthesis 64

1-tert-butyl 4-ethyl 3-oxopiperidine-1,4-dicarboxylate (74)

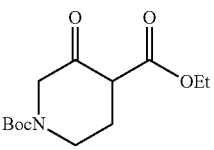

A mixture of ethyl 1-benzyl-3-oxo-4-piperidinecarboxylate hydrochloride (10.0 g, 33.58 mmol), Pd/C (10% wt., 1.0 g), Boc$_2$O (14.64 g, 67.16 mmol), Na$_2$CO$_3$ (3.56 g, 33.58 mmol) and EtOH (100 mL) was loaded into a Parr autoclave. Hydrogen was introduced (38 bar), and the mixture was stirred at 50° C. for 48 h. After the autoclave was cooled to 25° C. the hydrogen pressure was released, the catalyst was removed by filtration, and the mixture was concentrated under reduced pressure to give a yellow oil. Purification by column chromatography (hexane:EtOAc 2:1) gave the title compound (9.10 g, 100%) as a clear oil.

$R_f$=0.70 (hexane:EtOAc 2:1); $^1$H NMR (CDCl$_3$, 400 MHz) δ 12.10 (s, 1H, enol form —OH), 4.25 (q, J=7.1 Hz, 2H), 4.04 (s, 2H), 3.50 (t, J=5.8 Hz, 2H), 2.33 (t, J=5.8 Hz, 2H), 1.48 (s, 9H), 1.32 (t, J=7.1 Hz, 3H); HRMS (CI) calc. for C$_{13}$H$_{21}$NO$_5$ (M+NH$_4$)+289.1763, found: 289.1759.

Synthesis 65

(3R,4S)-1-tert-butyl 4-ethyl 3-hydroxypiperidine-1,4-dicarboxylate (75)

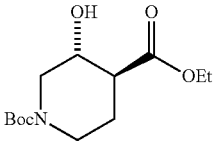

A solution of 1-tert-butyl 4-ethyl 3-oxopiperidine-1,4-dicarboxylate 74 (4.46 g, 16.47 mmol) and CH$_2$Cl$_2$ (20 mL) was added to a 450 mL glass liner containing a stirring bar and degassed by bubbling nitrogen for 30 min. [RuCl(p-cymene)(S)-T-BINAP]Cl complex (0.324 g, 0.33 mmol, 2 mol %) was added and the liner was loaded into a Parr autoclave. Hydrogen was introduced (10 bar), and the mixture was heated to 50° C. for 48 h. After the autoclave was cooled to 25° C. the hydrogen pressure was released, and the mixture was concentrated to give a red oil. Purification by column chromatography (hexane:EtOAc gradient 6:1 to 3:1) gave the title compound (3.47 g, 77%) as a clear oil. The enantiomeric ratio was determined to be 97:3 by HPLC analysis after converting an aliquot of the product to the (R)-acetylmandelic ester.

$R_f$=0.25 (hexane:EtOAc 2:1); [α]$_D^{22}$+14.2 (c 1.41, CHCl$_3$); $^1$H NMR (CDCl$_3$, 400 MHz) δ 4.27-4.22 (m, 1H), 4.21 (q, J=7.1 Hz, 2H), 3.83 (td, J=9.9, 4.8 Hz, 1H), 3.13 (brs, 1H), 2.71 (brs, 1H), 2.61 (dd, J=13.0, 10.3 Hz, 1H), 2.38 (ddd, J=12.3, 9.5, 4.1 Hz, 1H), 2.05-1.97 (m, 1H), 1.64-1.53 (m, 1H), 1.46 (s, 9H), 1.29 (t, J=7.1 Hz, 3H); $^{13}$C NMR (CDCl$_3$, 100 MHz) δ 173.9, 154.5, 80.0, 67.4, 49.2, 48.9, 42.7, 28.4, 26.7, 14.1; HRMS (ESI) calc. for C$_{13}$H$_{23}$NO$_5$ (M+Na)$^+$ 296.1474, found: 296.1486.

Synthesis 66

(3R,4S)-1-tert-butyl 4-ethyl 3-(methoxymethoxy)piperidine-1,4-dicarboxylate (76)

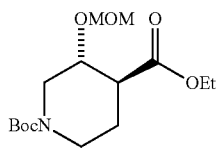

To a solution of (3R,4S)-1-tert-butyl 4-ethyl 3-hydroxypiperidine-1,4-dicarboxylate (4.10 g, 15.0 mmol) in CH$_2$Cl$_2$ (75 mL) was added DIPEA (10.18 mL, 60.0 mmol) and MOMCl (3.42 mL, 45.0 mmol). After 24 h, NaHCO$_3$ (50 mL) was added the organic layer was separated and the aqueous layer was extracted with EtOAc (4×30 mL). The combined organic layers were washed with NH$_4$Cl (30 mL), brine (30 mL), dried over MgSO$_4$, and concentrated under reduced pressure to give a yellow oil. Purification by column chromatography (hexane:EtOAc 4:1) gave the title compound as a clear oil (3.56 g, 75%).

R$_f$=0.65 (hexane:EtOAc 1:1); [α]$_D^{22}$+2.3 (c 1.12, CHCl$_3$); $^1$H NMR (CDCl$_3$, 400 MHz) δ 4.68 (s, 2H), 4.17 (q, J=7.2 Hz, 2H), 4.00-3.96 (m, 1H), 3.80-3.76 (m, J=9.6, 4.7 Hz, 2H), 3.35 (s, 3H), 2.78 (ddd, J=13.8, 11.8, 3.0 Hz, 1H), 2.70 (brs, 1H), 2.50 (ddd, J=11.4, 9.3, 4.1 Hz, 1H), 1.91 (dq, J=13.5, 3.6 Hz, 1H), 1.71-1.62 (m, 1H), 1.46 (s, 9H), 1.27 (t, J=7.1 Hz, 3H); $^{13}$C NMR (CDCl$_3$, 100 MHz) δ 173.4, 154.5, 96.3, 79.9, 73.3, 60.7, 55.6, 48.5, 47.1, 42.4, 28.3, 27.4, 14.2; HRMS (ESI) calc. for C$_{15}$H$_{27}$NO$_6$ (M+H)+ 318.1917, found: 318.1926.

Synthesis 67

(3R,4R)-tert-butyl 4-(hydroxymethyl)-3-(methoxymethoxy)piperidine-1-carboxylate (77)

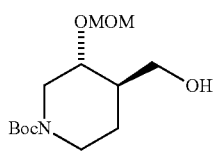

To a solution of (3R,4S)-1-tert-butyl 4-ethyl 3-(methoxymethoxy)piperidine-1,4-dicarboxylate (3.50 g, 11.0 mmol) in CH$_2$Cl$_2$ (60 mL) at −20° C. was added DIBAL-H (24 mL of a 1.0 M solution in hexane, 24.0 mmol). The solution was stirred at −20° C. for 1.5 h and then warmed to 22° C. The reaction mixture was quenched with Rochelle's salt and stirred vigorously for 2 h. The organic layer was separated and the aqueous phase was extracted with EtOAc (3×100 mL) and the combined organic phases were dried over MgSO$_4$ and concentrated under reduced pressure to give a clear oil. Purification by column chromatography (hexane:EtOAc 1:1) gave the title compound (2.35 g, 77%) as a clear oil.

R$_f$=0.20 (hexane:EtOAc 1:1); [α]$_D^{22}$+33.4 (c 1.11, CHCl$_3$); $^1$H NMR (CDCl$_3$, 400 MHz) δ 4.76 (d, J=6.7 Hz, 1H), 4.65 (d, J=6.7 Hz, 1H), 4.34 (brs, 1H), 4.04 (brs, 1H), 3.74-3.63 (m, 2H), 3.45-3.38 (m, 1H), 3.41 (s, 3H), 2.71-2.64 (m, 1H), 2.42 (brs, 2H) 1.71-1.64 (m, 2H), 1.45 (s, 9H), 1.39-1.34 (m, 1H); $^{13}$C NMR (CDCl$_3$, 100 MHz) δ 154.6, 96.1, 79.8, 75.5, 64.8, 55.9, 47.3, 44.2, 43.3, 28.4, 27.0; HRMS (ESI) calc. for C$_{13}$H$_{25}$NO$_5$ (M+Na)+298.1630, found: 298.1638.

Synthesis 68

(3R,4R)-tert-Butyl 4-(azidomethyl)-3-(methoxymethoxy)piperidine-1-carboxylate (37)

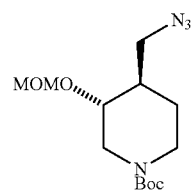

To a solution of (3R,4R)-tert-butyl 4-(hydroxymethyl)-3-(methoxymethoxy)piperidine-1-carboxylate (2.25 g, 8.2 mmol) and DI PEA (7.15 mL, 41.0 mmol) in CH$_2$Cl$_2$ (80 mL) was added MsCl (1.91 mL, 24.6 mmol). After 2 h, the reaction mixture was poured on water (50 mL) and extracted with EtOAc (4×50 mL). The combined organic layers were washed NH$_4$Cl (50 mL) with brine (50 mL), dried over MgSO$_4$, and concentrated under reduced pressure to a light yellow oil. The residue was dissolved in DMF (15 mL) and NaN$_3$ (2.66 g, 41.0 mmol) and NaI (122 mg, 0.82 mmol) were added and the mixture was heated 60° C. After 48 h, the reaction mixture was poured on water (50 mL) and extracted with EtOAc (3×50 mL). The combined organic layers were washed water (20 mL) and brine (20 mL), dried over MgSO$_4$, and concentrated under reduced pressure to give a light yellow oil. Purification by column chromatography (hexane:EtOAc 2:1) gave 37 (1.92 g, 78%) as a clear oil. All characterization data are identical to those reported in Synthesis 25.

Additional Compounds

The following additional compounds were prepared using analogous methods.

| Compound No. | Structure | Experimental Data |
|---|---|---|
| PPDA-004 | 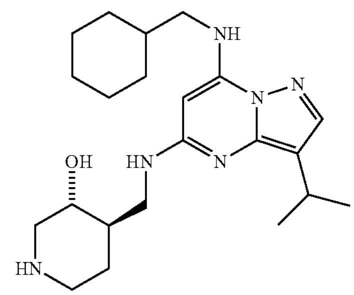 [SMILES: CC(C)c1cnn2c(NCC3CCCCC3)cc(NC[C@H]3CCNC[C@@H]3O)nc12] | $^1$H NMR (CD$_3$OD, 400 MHz) δ 7.88 (s, 1H), 5.56 (s, 1H), 3.76-3.66 (m, 2H), 3.54-3.39 (m, 4H), 3.11-2.95 (m, 2H), 2.82 (t, 1H, J = 11.3 Hz), 2.17 (ddd, J = 2.8, 6.1, 14.6 Hz, 1H), 1.85-1.67 (m, 8H), 1.36-1.30 (m, 10H), 1.11-1.03 (m, 2H |
| PPDA-005 | 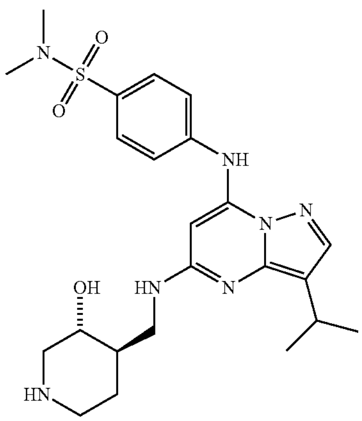 [SMILES: CC(C)c1cnn2c(Nc3ccc(S(=O)(=O)N(C)C)cc3)cc(NC[C@H]3CCNC[C@@H]3O)nc12] | $^1$H NMR (CD$_3$OD, 400 MHz) δ 7.81 (d, J = 8.7 Hz, 2H), 7.73 (s, 1H), 7.59 (d, J = 8.7 Hz, 2H), 5.52 (s, 1H), 3.97 (dd, J = 13.3, 3.3 Hz, 1H), 3.41 (td, J = 10.0, 4.3 Hz, 1H), 3.25-3.20 (m, 2H), 3.15-3.11 (m, 1H), 3.07 (sept, J = 6.9 Hz, 1H), 2.74 (dd, J = 12.1, 3.2 Hz, 1H), 2.70 (s, 6H), 2.61-2.55 (m, 1H), 1.84-1.80 (m, 1H), 1.66-1.49 (m, 2H), 1.30 (d, J = 7.1 Hz, 3H), 1.28 (d, J = 7.1 Hz, 3H)<br>HRMS (ESI) Calcd. for C$_{23}$H$_{34}$N$_7$O$_3$S [M + H]$^+$, 488.2444, found 488.2459 |
| PPDA-006 | 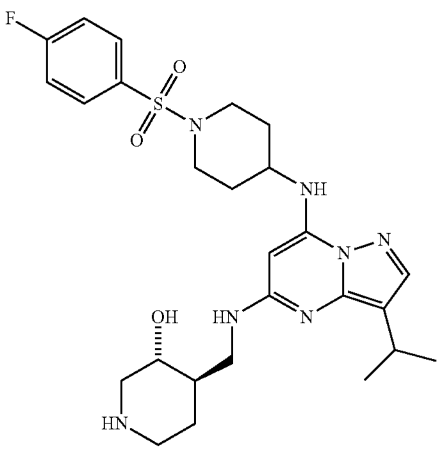 [SMILES: CC(C)c1cnn2c(NC3CCN(S(=O)(=O)c4ccc(F)cc4)CC3)cc(NC[C@H]3CCNC[C@@H]3O)nc12] | $^1$H NMR (CD$_3$OD, 500 MHz) δ 7.86 (dd, J = 8.6, 5.1 Hz, 2H), 7.61 (s, 1H), 7.36 (t, J = 8.7 Hz, 2H), 5.49 (s, 1H), 3.93 (dd, J = 14.5, 3.7 Hz, 1H), 3.81-3.63 (m, 1H), 3.58-3.40 (m, 1H), 3.33-3.20 (m, 7H), 3.01 (sept, J = 6.9 Hz, 1H), 2.87 (td, J = 12.2, 3.4 Hz, 1H), 2.70 (dd, J = 12.0, 10.6 Hz, 1H), 2.67-2.60 (m, 1H), 2.22-2.04 (m, 1H), 1.89 (dt, J = 10.4, 2.9 Hz, 1H), 1.75-1.61 (m, 4H), 1.34 (d, J = 6.8 Hz, 6H)<br>HRMS (ESI) Calcd. for C$_{26}$H$_{37}$N$_7$O$_3$FS [M + H]$^+$, 546.2663, found 546.2676 |
| PPDA-008 | 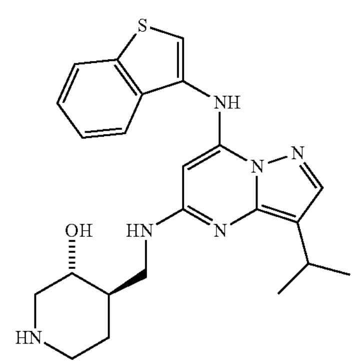 [SMILES: CC(C)c1cnn2c(Nc3csc4ccccc34)cc(NC[C@H]3CCNC[C@@H]3O)nc12] | $^1$H NMR (CD$_3$OD, 500 MHz) δ 8.00 (d, J = 7.6 Hz, 1H), 7.89 (d, J = 8.0 Hz, 1H), 7.88 (s, 1H), 7.71 (s, 1H), 7.42 (t, J = 7.2 Hz, 1H), 7.38 (t, J = 6.8 Hz, 1H), 5.60 (s, 1H), 3.76-3.70 (m, 1H), 3.65-3.6 (m, 1H), 3.45-3.42 (m, 1H), 3.37 (s, 2H), 3.11-3.07 (m, 1H), 2.96-2.91 (m, 1H), 2.81-2.77 (m, 1H), 2.05-2.01 (m, 1H), 1.89-1.84 (m, 1H), 1.66-1.62 (m, 1H), 1.31 (d, J = 6.8 Hz, 3H), 1.29 (d, J = 6.8, 3H) |

-continued

| Compound No. | Structure | Experimental Data |
|---|---|---|
| PPDA-011 | 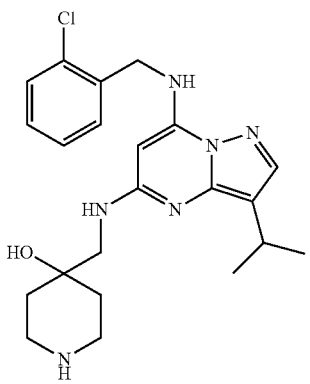 [SMILES: CC(C)c1cnn2c(NCc3ccccc3Cl)cc(NCC3(O)CCNCC3)nc12] | $^1$H NMR (CD$_3$OD, 500 MHz) δ 7.79 (s, 1H), 7.46-7.44 (m, 1H), 7.42-7.40 (m, 1H), 7.31-7.29 (m, 2H), 5.57 (s, 1H) 4.73 (brs, 2H), 3.45 (s, 2H), 3.28-3.25 (m, 4H), 3.06 (sept, J = 6.8 Hz, 1H), 1.87-1.76 (m, 4H), 1.31 (d, J = 6.8 Hz, 6H) HRMS (ESI) Calcd. for C$_{22}$H$_{30}$N$_6$OCl [M + H]$^+$, 429.2170, found 429.216 |
| PPDA-012 | 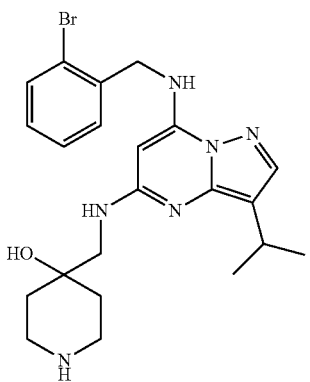 [SMILES: CC(C)c1cnn2c(NCc3ccccc3Br)cc(NCC3(O)CCNCC3)nc12] | $^1$H NMR (CD$_3$OD, 500 MHz) δ 7.90 (s, 1H), 7.64 (d, J = 10.0Hz, 1H), 7.42 (d, J = 10 Hz, 1H), 7.36 (t, J = 10 Hz, 1H), 7.24 (t, J = 10 Hz, 1H), 5.45 (s, 1H), 4.81 (s, 2H), 3.49 (s, 2H), 3.34-3.28 (m, 4H), 3.15-3.10 (m, 1H), 1.91-1.89 (m, 4H), 1.32 (6H, d, J = 6.8 Hz) $^{13}$C NMR (125 MHz, CD$_3$OD) δ 155.5, 150.8, 143.9, 136.4, 134.8, 134.3, 132.4, 130.9, 130.1, 129.2, 124.1, 112.6, 68.7, 53.5, 47.2, 41.0, 32.1, 24.1, 23.5 HRMS (ESI) Calcd. for C$_{22}$H$_{30}$N$_6$OBr [M + H]$^+$, 473.1664, found 473.1667 |
| PPDA-013 | 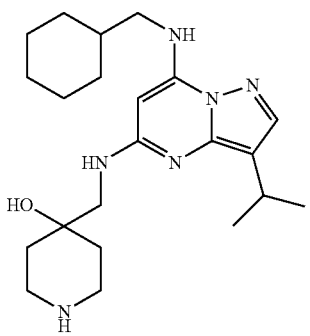 [SMILES: CC(C)c1cnn2c(NCC3CCCCC3)cc(NCC3(O)CCNCC3)nc12] | HRMS (ESI) Calcd. for C$_{22}$H$_{37}$N$_6$O [M + H]$^+$, 401.3029, found 401.3010 |
| PPDA-014 | 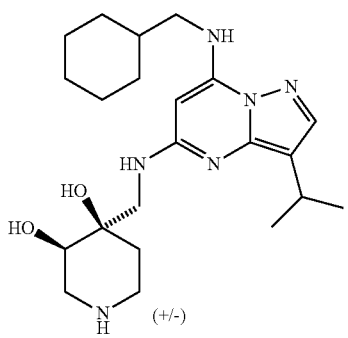 | $^1$H NMR (CD$_3$OD, 500 MHz) δ 7.88 (s, 1H), 5.60 (s, 1H), 3.90-3.88 (m, 1H), 3.69 (d, J = 14.2 Hz, 1H), 3.63 (d, J = 14.2 Hz, 1H), 3.35-3.15 (m, 5H), 3.07 (sept, J = 6.8 Hz, 1H), 1.85-1.70 (m, 6H), 1.32 (d, J = 6.8 Hz, 6H), 1.30-1.25 (m, 4H), 1.11-0.98 (m, 4H) |

| Compound No. | Structure | Experimental Data |
|---|---|---|
| PPDA-016 | 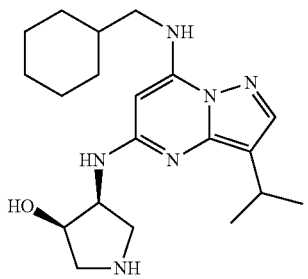 [SMILES: CC(C)c1cnn2c(NCC3CCCCC3)cc(N[C@H]3CNC[C@H]3O)nc12] | ¹H NMR (CD₃OD, 500 MHz) δ 7.85 (m, 1H), 4.71 (m, 1H), 4.52 (s, 1H), 3.84-3.80 (m, 1H), 3.51-3.38 (m, 4H), 3.07-3.02 (m, 1H), 1.82-1.64 (m, 6H), 1.35-1.30 (m, 6H), 1.23-1.18 (m, 3H), 1.15-0.92 (m, 4H) ¹³C-NMR (125 MHz, CD₃OD) δ 154.2, 151.3, 144.0, 134.8, 112.6, 69.7, 55.4, 53.4, 47.4, 39.0, 31.8, 27.4, 27.0, 24.2, 23.5 |
| PPDA-017 | 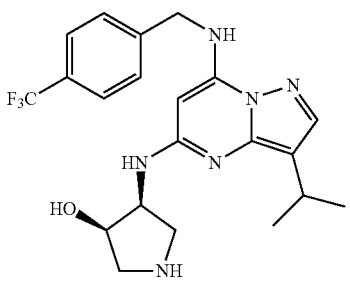 [SMILES: CC(C)c1cnn2c(NCc3ccc(C(F)(F)F)cc3)cc(N[C@H]3CNC[C@H]3O)nc12] | ¹H NMR (CD₃OD, 500 MHz) δ 7.93 (s, 1H), 7.73-7.56 (m, 4H), 4.93 (s, 2H), 4.68 (s, 1H), 4.49 (s, 1H), 3.77-3.72 (m, 1H), 3.51-3.40 (m, 3H), 3.17-3.12 (m, 2H), 1.32 (d, J = 6.8 Hz, 6H) ¹³C NMR (125 MHz, CD₃OD) δ 154.4, 151.3, 144.2, 142.6, 135.0, 131.2, 130.9, 129.0, 126.9, 126.84, 126.81, 124.3, 112.7, 69.7, 55.3, 53.2, 47.2, 46.2, 30.8, 24.1, 23.5 |
| PPDA-019 | 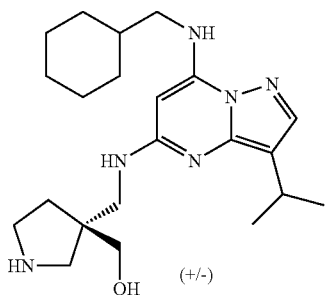 [SMILES: CC(C)c1cnn2c(NCC3CCCCC3)cc(NC[C@@]3(CO)CCNC3)nc12] | HRMS (ESI) Calcd. for C₂₂H₃₇N₆O [M + H]⁺, 401.3029, found 401.3042 |
| PPDA-020 | 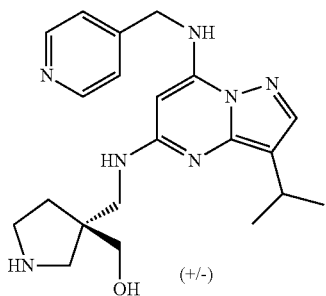 [SMILES: CC(C)c1cnn2c(NCc3ccncc3)cc(NC[C@@]3(CO)CCNC3)nc12] | ¹³C NMR (125 MHz, CD₃OD) δ 160.0, 155.8, 144.1, 143.1, 135.1, 126.6, 126.5, 112.9, 66.3, 65.4, 51.5, 46.2, 45.9, 31.7, 24.1, 23.5, 23.5; HRMS (ESI) Calcd. for C₂₁H₃₀N₇O [M + H]⁺, 396.2512, found 396.2527 |

| Compound No. | Structure | Experimental Data |
|---|---|---|
| PPDA-021 | 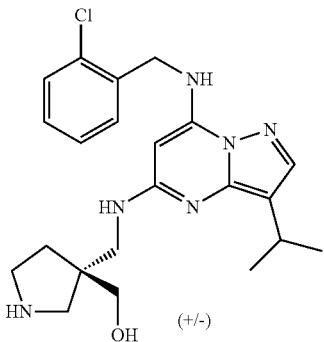 [SMILES: CC(C)c1cnn2c(NCc3ccccc3Cl)cc(NC[C@@]3(CO)CCNC3)nc12] (+/-) | ¹H NMR (CD₃OD, 500 MHz) δ 7.69 (s, 1H), 7.44-7.42 (m, 1H), 7.40-7.38 (m, 1H), 7.29-7.26 (m, 2H), 5.15 (s, 1H), 4.64 (s, 2H), 3.55-3.34 (m, 6H), 3.16 (m, 2H), 3.02 (sept, J = 6.5 Hz, 1H), 1.96-1.85 (m, 2H), 1.30 (d, J = 6.5 Hz, 3H), 1.28 (d, J = 6.5 Hz, 3H) ¹³C NMR (125 MHz, CD₃OD) δ 159.5, 148.3, 146.0, 141.7, 136.0, 134.1, 130.7, 130.1, 129.3, 128.4, 113.7, 73.9, 64.8, 51.8, 50.8, 46.1, 44.8, 44.4, 31.5, 24.7, 23.9, 23.7 HRMS (ESI) Calcd. for $C_{22}H_{30}N_6OCl$ [M + H]⁺, 429.2170, found 429.2175 |
| PPDA-023 | 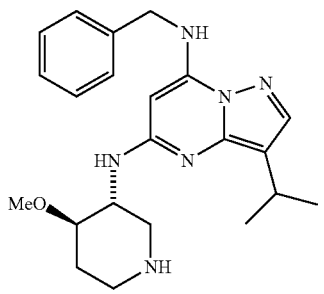 | ¹H NMR (CDCl₃, 500 MHz) δ 7.95 (s, 1H), 7.47 (d, J = 7.5 Hz, 2H), 7.39 (t, J = 7.4 Hz, 2H), 7.33 (t, J = 7.1 Hz, 1H), 5.42 (s, 1H) 4.78 (s, 2H), 4.16 (s, 1H), 3.39-3.52 (m, 2H), 3.39 (s, 3H), 3.11-3.18 (m, 4H), 2.48 (d, J = 13.4 Hz, 1H), 1.85 (s, 1H), 1.35 (d, J = 6.0 Hz, 3H), 1.33 (d, J = 6.0 Hz, 3H) HRMS (ESI) Calcd. for $C_{22}H_{30}N_6O$ [M + H]⁺, 395.2559, found 395.2547 |
| PPDA-024 | 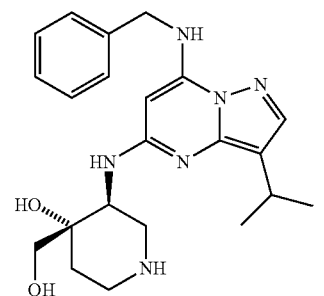 [SMILES: CC(C)c1cnn2c(NCc3ccccc3)cc(N[C@H]3CNCC[C@@]3(O)CO)nc12] | ¹H NMR (DMSO, 500 MHz) δ 9.55 (brs, 2H), 7.45-7.34 (m, 6H), 5.71 (brs, 1H), 4.66-4.62 (m, 2H), 4.12-4.09 (m, 1H), 3.20-3.11 (m, 9H), 2.48 (s, 1H), 2.15 (s, 1H), 1.62 (m, 1H), 1.20 (s, 6H); HRMS (ESI) Calcd. for $C_{22}H_{31}N_6O_2$ [M + H]⁺, 411.2508, found 411.2502 |
| PPDA-025 | 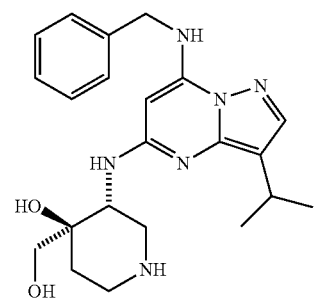 | ¹H NMR (DMSO, 500 MHz) δ 9.55 (brs, 2H), 7.45-7.34 (m, 6H), 5.71 (brs, 1H), 4.66-4.62 (m, 2H), 4.12-4.09 (m, 1H), 3.20-3.11 (m, 9H), 2.48 (s, 1H), 2.15 (s, 1H), 1.62 (m, 1H), 1.20 (s, 6H) HRMS (ESI) Calcd. for $C_{22}H_{31}N_6O_2$ [M + H]⁺, 411.2508, found 411.2497 |

-continued

| Compound No. | Structure | Experimental Data |
|---|---|---|
| PPDA-027 | 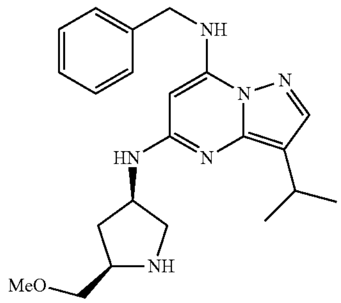 [SMILES: COC[C@H]1C[C@@H](Nc2cc(NCc3ccccc3)n3ncc(C(C)C)c3n2)CN1] | $^1$H NMR (DMSO, 500 MHz) δ 9.86 (brs, 1H), 9.19 (brs, 1H), 8.30 (brs, 1H), 7.79 (s, 1H), 7.42 (d, J = 7.5 Hz, 2H), 7.35 (t, J = 7.2 Hz, 2H), 7.27 (t, J = 7.0 Hz, 1H), 5.37 (s, 1H), 4.60-4.53 (m, 3H), 3.83-3.75 (m, 1H) 3.69 (dd, J = 10.7, 7.4 Hz, 1H), 3.63 (dd, J = 10.7, 4.2 Hz, 1H), 3.55 (dd, J = 11.8, 7.4 Hz, 1H), 3.36 (s, 3H), 3.14-3.80 (m, 2H), 2.08-2.03 (m, 1H), 1.74-1.68 (m, 1H), 1.29 (d, J = 7.0 Hz, 6H)<br>$^{13}$C NMR (125 MHz, DMSO) δ 143.0, 140.2, 139.4, 137.3, 127.9, 127.8, 126.6, 126.4, 126.3, 110.8, 70.2, 57.9, 57.0, 49.4, 48.2, 44.7, 39.0, 29.9, 22.5<br>HRMS (ESI) Calcd. for $C_{22}H_{30}N_6O$ [M + H]$^+$, 395.2559, found 395.2563 |
| PPDA-028 | 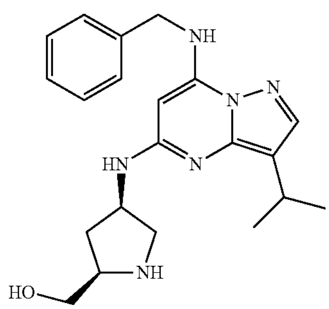 [SMILES: CC(C)c1cnn2c(NCc3ccccc3)cc(N[C@H]3CN[C@@H](CO)C3)nc12] | $^1$H NMR (DMSO, 500 MHz) δ 9.79 (brs, 1H), 9.15 (brs, 1H), 8.54 (brs, 1H), 7.83 (s, 1H), 7.43 (d, J = 6.5 Hz, 2H), 7.35 (t, J = 7.4, 7.0 Hz, 2H), 7.31-7.25 (m, 1H), 5.43 (s, 1H), 4.65-4.60 (m, 1H), 4.64 (s, 2H), 4.59-4.56 (m, 1H), 3.76-3.66 (m, 3H), 3.57 (dd, J = 11.6, 7.4 Hz, 1H), 3.13 (sept, J = 7 Hz, 1H), 3.08 (dd, J = 11.5, 6.0 Hz, 1H), 2.48-2.44 (m, 1H), 1.80-1.74 (m, 1H), 1.27 (d, J = 7.0 Hz, 6H)<br>HRMS (ESI) Calcd. for $C_{21}H_{28}N_6O$ [M + H]$^+$, 381.2403, found 381.2410 |
| PPDA-029 | 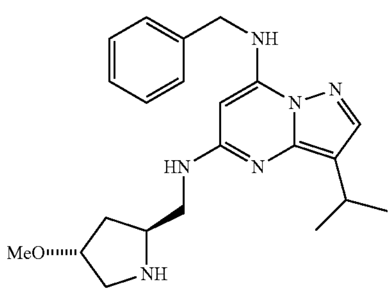 [SMILES: CO[C@H]1CN[C@H](CNc2cc(NCc3ccccc3)n3ncc(C(C)C)c3n2)C1] | $^1$H NMR (CD$_3$OD, 500 MHz) δ 7.75 (s, 1H), 7.39-7.32 (m, 5H), 5.32 (s, 1H), 4.58 (s, 2H), 4.14 (t, J = 3.2 Hz, 1H), 4.02-3.97 (m, 1H), 3.78 (dd, J = 15.4, 2.3 Hz, 1H), 3.52 (dd, J = 15.4, 6.4 Hz, 1H), 3.38 (m, 1H), 3.36 (s, 3H), 3.18 (dd, J = 12.4, 3.4 Hz, 1H), 3.04 (sept, J = 6.9 Hz, 1H), 2.29 (dd, J = 14.0, 6.8 Hz, 1H), 1.95 (ddd, J = 14.0, 10.4, 4.1 Hz, 1H), 1.34 (d, J = 6.9 Hz, 3H), 1.34 (d, J = 6.9 Hz, 3H)<br>$^{13}$C NMR (125 MHz, CD$_3$OD) δ 158.3, 147.3, 143.7, 140.3, 137.5, 128.4, 127.1, 126.6, 112.2, 79.7, 72.4, 60.2, 55.3, 48.7, 45.1, 43.0, 32.1, 23.5, 22.5<br>HRMS (ESI) Calcd. for $C_{22}H_{31}N_6O$ [M + H]$^+$, 395.2559, found 395.2557 |

| Compound No. | Structure | Experimental Data |
|---|---|---|
| PPDA-030 | 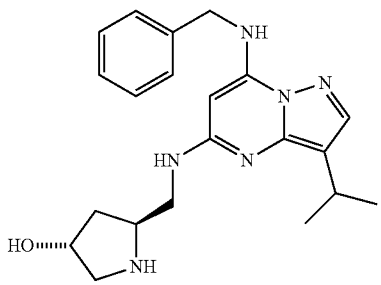 [SMILES: CC(C)c1cnn2c(NCc3ccccc3)cc(NC[C@@H]3C[C@@H](O)CN3)nc12] | $^1$H NMR (CD$_3$OD, 500 MHz) δ 7.73 (s, 1H), 7.33-7.27 (m, 5H), 5.38 (s, 1H), 4.55 (brs, 1H), 4.54 (s, 2H), 4.15-4.13 (m, 1H), 3.79 (br d, J = 14.9 Hz, 1H), 3.54 (dd, J = 15.1, 6.2 Hz, 1H), 3.21 (m, 2H), 3.03 (sept, J = 6.9 Hz, 1H), 2.13 (dd, J = 13.4, 6.9 Hz, 1H), 2.01 (td, J = 6.9, 3.8 Hz, 1H), 1.31 (d, J = 6.9 Hz, 6H) HRMS (ESI) Calcd. for C$_{21}$H$_{29}$N$_6$O [M + H]$^+$, 381.2403, found 381.2410 |
| PPDA-031 | 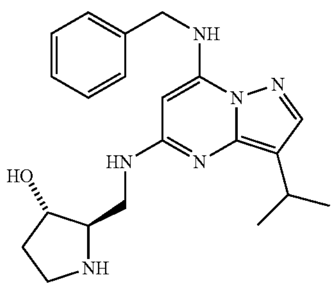 [SMILES: CC(C)c1cnn2c(NCc3ccccc3)cc(NC[C@H]3NCC[C@@H]3O)nc12] | $^1$H NMR (CD$_3$OD, 500 MHz) δ 7.96 (s, 1H), 7.42-7.35 (m, 5H), 5.57 (s, 1H), 4.82 (s, 2H), 4.36-4.32 (m, 1H), 3.79-3.77 (m, 3H), 3.67 (m, 1H), 3.50 (t, J = 7.4 Hz, 1H), 3.18 (sept, J = 6.8 Hz, 1H), 2.34 (m, 1H), 2.04 (m, 1H), 1.34 (d, J = 6.8 Hz, 6H) HRMS (ESI) Calcd. for C$_{21}$H$_{29}$N$_6$O [M + H]$^+$, 381.2403, found 381.2419 |
| PPDA-032 | 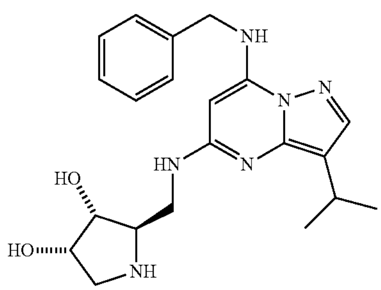 [SMILES: CC(C)c1cnn2c(NCc3ccccc3)cc(NC[C@H]3NC[C@H](O)[C@@H]3O)nc12] | $^1$H NMR (CD$_3$OD, 500 MHz) δ 7.75 (s, 1H), 7.44-7.35 (m, 5H), 5.34 (s, 1H), 4.59 (s, 2H), 4.22 (m, 2H), 3.84 (dd, J = 14.7, 1.1 Hz, 1H), 3.68-3.63 (m, 2H), 3.29-3.25 (m, 2H), 3.02 (sept, J = 6.9 Hz, 1H), 1.33 (d, J = 6.9 Hz, 3H), 1.32 (d, J = 6.9 Hz, 3H) $^{13}$C NMR (125 MHz, CD$_3$OD) δ 158.4, 147.4, 143.5, 140.3, 137.5, 128.4, 127.2, 126.6, 112.2, 72.4, 72.1, 70.2, 48.6, 48.5, 45.0, 41.2, 23.4, 22.5; HRMS (ESI) Calcd. for C$_{21}$H$_{29}$N$_6$O$_2$ [M + H]$^+$, 397.2352, found 397.2330 |

Biological Methods and Data

In vitro Kinase Assays and IC$_{50}$ Determination

Purified recombinant CDK1/cycA1, CDK2/cycA1, CDK4/cycD1, CDK5/p35NCK, CDK6/cycD1, CDK7/CycH/MAT1, and CDK9/CycT1 were purchased from ProQinase GmbH. Kinase assays were performed according to manufacturer's protocols. Rb-CTF (ProQinase GmbH) (cat number: 0040-0000-6) was used as the kinase substrate for CDK1, CDK2, CDK4, and CDK6 kinases. RNA Polymerase II C-Terminal domain (Pol II CTD) peptide (YSPTSPSYSPTSPSYSPTSPS) (Cambridge Research Biochemicals) peptide was used for CDK7 and CDK9 kinase assays. A luciferase assay (PKLight assay; Cambrex) was used to determine ATP remaining at the end of the kinase reaction, which provides a measure of kinase activity, according to the manufacturer's protocols.

Kinase assays were carried out by incubation of increasing amounts of test compound with purified recombinant CDK-Cyclin complex, followed by measurement of free ATP remaining in the reaction using the luciferase assay kit (PKLight, Cambrex) which therefore provided a measure of inhibition for the specific CDK.

5 μL of 1× kinase buffer (Cell Signalling Technologies) was mixed with 200 ng CDK1, 200 ng CDK2, 50 ng CDK4, 100 ng CDK5, or 200 ng CDK6 with 5 μg Rb-CTF and 300 ng CDK7 or 200 ng CDK9 with 500 μM RNA Poll II CTD peptide. ATP at the K$_m$ for each enzyme (0.16 μM for CDK1; 0.58 μM for CDK2; 18.7 μM for CDK4; 1.8 μM for CDK5; 20.9 μM for CKD6; 4.1 μM for CDK7; and 4 μM for CDK9) was added to the reaction mix and doubly distilled water was added to make the volume up to 39 μL. The mixture was incubated at 30° C. for 30 minutes. The reaction is stopped with 20 μL of Stop Solution (provided in the PKLight kit) for 10 minutes at room temperature. Then 40 μL of the luciferase mix was added to the reaction mixture which was incubated for a further 10 minutes at room temperature and measured using the Tecan Infinite 2000 plate reader. GraphPad Prism Software was used to generate standard curve and determine the $IC_{50}$'s for each CDK.

CDK activities for PPDA-001 were determined using an in vitro kinase assay, as described above. The $IC_{50}$ values (μmol/L) are shown in the following table. The results of three experiments are reported, along with standard errors of the means (SEM) (μmol/L).

TABLE 1

$IC_{50}$ Data for PPDA-001

| Kinase | $IC_{50}$ (μmol/L) | SEM (μmol/L) |
|---|---|---|
| CDK1 | 1.52 | 0.04 |
| CDK2 | 0.58 | 0.1 |
| CDK4 | 42.1 | 0.9 |
| CDK5 | 9.0 | 0.11 |
| CDK6 | 32.1 | 0.8 |
| CDK7 | 0.041 | 0.04 |
| CDK9 | 1.1 | 0.03 |

In vitro kinase inhibition data (CDK1, CDK2, CDK7) and selectivity (CDK1/7, CDK2/7) data are summarised in the following table.

TABLE 2

$IC_{50}$ Data for Various Compounds

| | In vitro Kinase Inhibition | | | Selectivity | |
|---|---|---|---|---|---|
| Compound | CDK1 $IC_{50}$ (nM) | CDK2 $IC_{50}$ (nM) | CDK7 $IC_{50}$ (nM) | CDK1/CDK7 (fold) | CDK2/CDK7 (fold) |
| PPDA-001 | 1520 | 580 | 41 | 37 | 14 |
| PPDA-002 | 1380 | 2030 | 18 | 77 | 113 |
| PPDA-003 | 1910 | 114 | 47 | 41 | 2.5 |
| PPDA-004 | 1820 | 1290 | 940 | 1.9 | 1.4 |
| PPDA-005 | 213 | 38 | 111 | 1.9 | 0.3 |
| PPDA-006 | 405 | 178 | 40 | 10 | 4.5 |
| PPDA-007 | 1146 | 503 | 461 | 2.5 | 1.1 |
| PPDA-008 | 2950 | 42 | 120 | 25 | 0.4 |
| PPDA-009 | 559 | 459 | 462 | 1.2 | 1.0 |
| PPDA-010 | 3625 | 115 | 788 | 4.6 | 0.1 |
| PPDA-011 | 143 | 98 | 414 | 0.3 | 0.2 |
| PPDA-012 | 74 | 118 | 484 | 0.2 | 0.2 |
| PPDA-013 | 330 | 344 | 80 | 4.1 | 4.3 |
| PPDA-014 | 8680 | 481 | 975 | 8.9 | 0.5 |
| | In vitro Kinase Inhibition | | | Selectivity | |
| PPDA-015 | 3950 | 1290 | 27 | 146 | 48 |
| PPDA-016 | 1460 | 4550 | 246 | 5.9 | 18 |
| PPDA-017 | 1350 | 754 | 1890 | 0.7 | 0.4 |
| PPDA-018 | 41 | 1 | 14 | 2.9 | 0.1 |
| PPDA-019 | 80 | 9 | 29 | 2.8 | 0.3 |
| PPDA-020 | 441 | 22 | 44 | 10 | 0.5 |
| PPDA-021 | 177 | 22 | 81 | 2.2 | 0.3 |
| PPDA-022 | 1900 | 568 | 73 | 26 | 7.8 |
| PPDA-023 | 1200 | 450 | 60 | 20 | 7.5 |
| PPDA-024 | 844 | 1027 | 150 | 5.6 | 6.8 |
| PPDA-025 | 285 | 106 | 77 | 3.7 | 1.4 |
| PPDA-026 | 162 | 203 | 89 | 1.8 | 2.3 |
| PPDA-027 | 253 | 680 | 18 | 14 | 38 |
| PPDA-028 | 4010 | 262 | 43 | 93 | 6.1 |
| PPDA-029 | — | 2840 | 1007 | — | 2.8 |
| PPDA-030 | — | 999 | 59 | — | 17 |
| PPDA-031 | — | 393 | 473 | — | 0.8 |
| PPDA-032 | — | 1500 | 305 | — | 4.9 |

Cell Growth Inhibitions Assays

All cells were purchased from the American Type Culture Collection (ATCC) and MCF7 cells were routinely cultured in Dulbecco's Modified Eagle's Medium (DMEM) supplemented with 10% fetal calf serum (FCS) (First Link) and HCT116 cells were routinely cultured in Roswell Park Memorial Instititute Medium (RPMI) supplemented with 10% FCS. Cell growth was assessed using a known sulforhodamine B assay (see, e.g., Skehan et al., 1990).

MCF-7 cells purchased from ATCC (USA) were routinely passaged in DMEM, supplemented with 10% FCS and HCT116 cells purchased from ATCC (USA) were routinely passaged in RPMI supplemented with 10% FCS and kept in a 37° C. incubator with 5% $CO_2$. The growth assay for both cell lines was performed in the appropriate media using the exact same protocol as described here. For the growth assay, 5000 cells were seeded into each well of 96-well plates in DMEM containing 10% FCS. Test compounds prepared in DMSO were added to the medium at concentrations ranging from 0.00038-100 μM. The cells were incubated for a further 72 hours, at which time they were fixed by the addition of 100 μL/well of ice-cold 40% trichloroacetic acid (TCA). The plates were left for 1 hour at 4° C., washed in water and 100 μL of 0.4% (w/v) sulforhodamine (SRB; Sigma-Aldrich, UK) prepared in 1% acetic acid was added. Plates were washed in 1% acetic acid to remove excess SRB reagent, air dried, and bound dye was solubilized by the addition of 100 μL of 10 mM tris base. The plates were read at 492 nm using a plate reader. The optical densities (OD) at 492 nm were plotted to determine the concentration of test compound at which 50% inhibition of growth is observed (using GraphPad Prism).

PPDA-001 inhibited the growth of breast (MCF7) and colorectal (HCT116) cancer cell lines with $GI_{50}$ values of <1 μmol/L.

The data are summarised in the following table.

TABLE 3

Growth Inhibition, $GI_{50}$ (μM)

| Compound No | MCF7 | HCT116 |
|---|---|---|
| PPDA-001 | 0.96 | 0.63 |
| PPDA-002 | 1.5 | 5.1 |
| PPDA-003 | — | — |
| PPDA-004 | 2.7 | 2.5 |
| PPDA-005 | 4.22 | 7.2 |
| PPDA-006 | 8.4 | 10.0 |
| PPDA-007 | 2.1 | 4.1 |
| PPDA-008 | 3.1 | 5.1 |
| PPDA-009 | 38.9 | 86.6 |
| PPDA-010 | 11.9 | 25.0 |
| PPDA-011 | 0.3 | 1.6 |
| PPDA-012 | 0.5 | 1.6 |
| PPDA-013 | 1.2 | 1.1 |
| PPDA-014 | 45.6 | 53.5 |
| PPDA-015 | 4.1 | 12.7 |
| PPDA-016 | 13.1 | 7.4 |
| PPDA-017 | 12.8 | 11.4 |
| PPDA-018 | 0.1 | 0.9 |
| PPDA-019 | 0.3 | 0.4 |
| PPDA-020 | 0.6 | 1.5 |
| PPDA-021 | 0.2 | 1.2 |
| PPDA-022 | 3.7 | 10.4 |
| PPDA-023 | 3.7 | 5.6 |
| PPDA-024 | 12.2 | 46.4 |
| PPDA-025 | 10.1 | 23.7 |
| PPDA-026 | 2.0 | 10.7 |
| PPDA-027 | 3.4 | 8.9 |
| PPDA-028 | 3.3 | 7.3 |
| PPDA-029 | 17.6 | >100 |
| PPDA-030 | 20.2 | >100 |
| PPDA-031 | 5.6 | 20.4 |
| PPDA-032 | — | — |

NCI Screening

To extend the analysis to a more extensive set of cancer cell lines, PPDA-001 was submitted to the National Cancer Institute's Division of Cancer Treatment and Diagnosis in vitro screen of human tumor cell lines (http://dtp.nci.nih.gov/branches/btb/ivclsp.html).

The results are shown graphically in FIG. 1.

FIG. 1 is a graph of percentage growth inhibition as a function of the base-10 logarithm of the molar concentration of the test compound, PPDA-001, as determined by the NCI60 cancer cell line screen. Each line represents one cell line.

The screen demonstrated that PPDA-001 caused inhibition of all 60 cancer cell lines (mean $GI_{50}$=0.28 μmol/L; range $GI_{50}$=0.04 to 2.1 μmol/L).

HCT116 Tumour Xenograft Study

Animals (female Balb/c nu/nu mice) were randomized to 4 arms (15 animals in each arm), with tumor-bearing animals being treated PO by oral gavage, with PPDA-001 using 5% DMSO in PBS as vehicle. Once tumors reached a volume of 100-200 mm$^3$, the animals were either left untreated, or treated with vehicle, 50 mg/kg PPDA-001 bi-daily (bd) (8-hours between $1^{st}$ and $2^{nd}$ administration daily), or treated once daily with 100 mg/kg PPDA-001.

Figure 2:
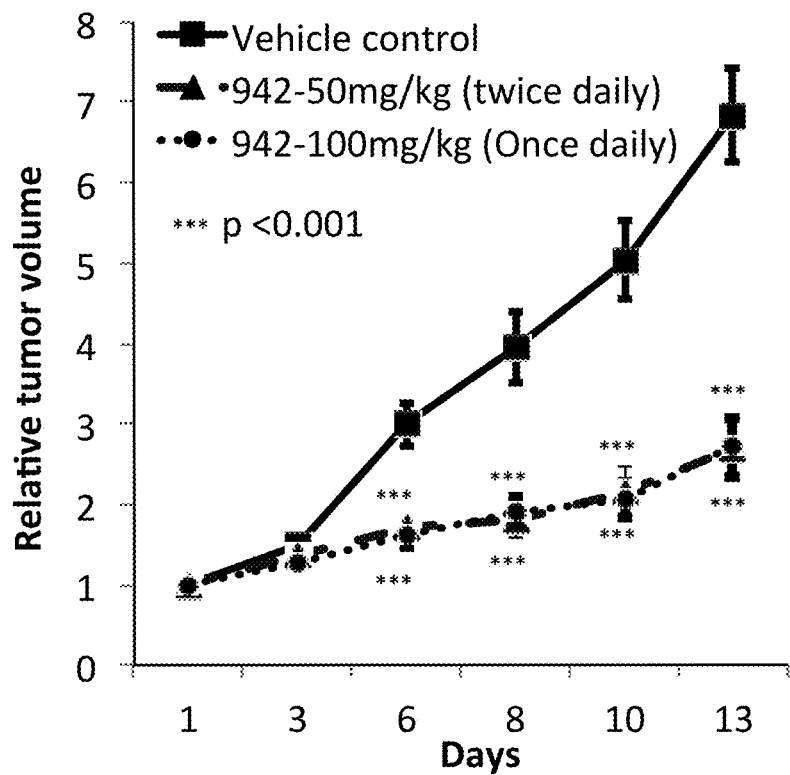
FIG. 2 is a graph of relative tumour volume as a function of time in the HCT116 tumour xenograft study, for vehicle control (squares), 50 mg/kg/bi-daily (triangles), and 100 mg/kg once daily (crosses). Error bars represent standard errors of the mean (SEM).

The results are illustrated in FIG. 2.

FIG. 2 is a graph of relative tumour volume as a function of time in the HCT116 tumour xenograft study, for vehicle control (squares), 50 mg/kg/bi-daily (triangles), and 100 mg/kg once daily (crosses). Error bars represent standard errors of the mean (SEM).

Animal weights in the PPDA-001 treatment arms fell over the course of the study, reaching 92%, compared to vehicle treated animals whose weight fell to 98%.

Figure 3:
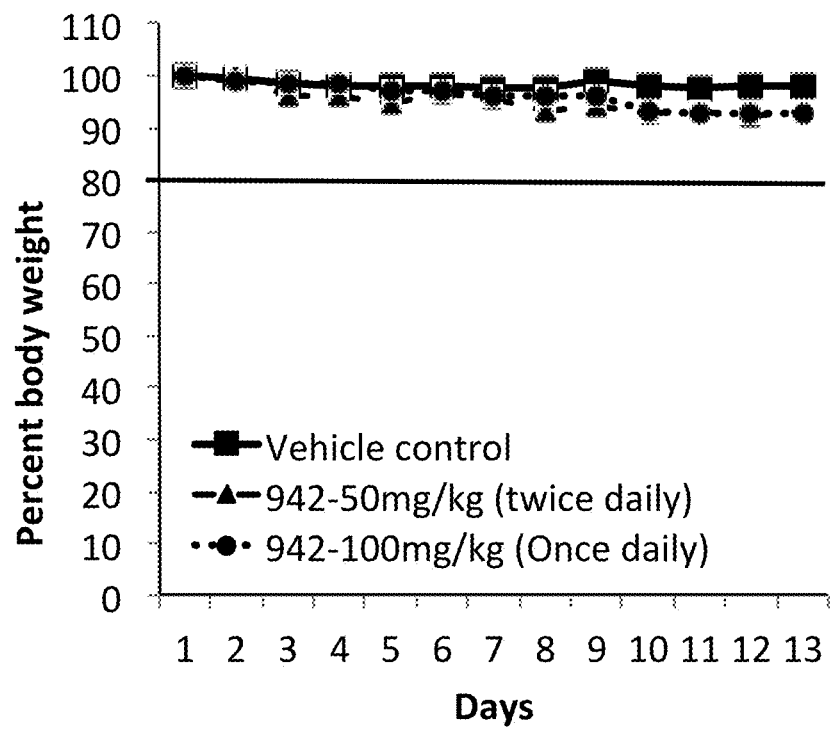
FIG. 3 is a graph of percent body weight as a function of time in the HCT116 tumour xenograft study, for vehicle control (squares), 50 mg/kg/bi-daily (triangles), and 100 mg/kg once daily (crosses).

The results are illustrated in FIG. 3.

FIG. 3 is a graph of percent body weight as a function of time in the HCT116 tumour xenograft study, for vehicle control (squares), 50 mg/kg/bi-daily (triangles), and 100 mg/kg once daily (crosses).

PPDA-001 substantially reduced tumor growth at the 50 mg/kg/bi-daily and 100 mg/kg once daily treatment regimens, demonstrating a 65% reduction in tumor growth in the PPDA-001 treatment arms, as compared with the control arms. There was no difference in tumor growth between these two doses (p<0.001).

Comparison Studies

The following compounds were prepared for comparison purposes, in particular, for comparison with PPDA-001. These compounds differ from PPDA-001 invention by (a) the absence of an "oxy" substituent, in the case of XX-01, or (b) the absence of a nitrogen-containing heterocyclic group, in the case of XX-02.

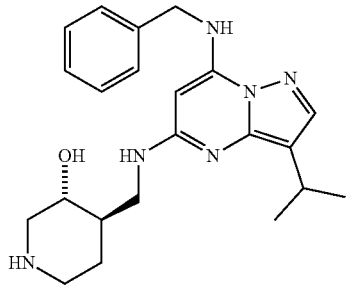

PPDA-001

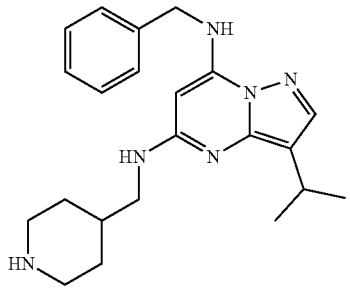

XX-01

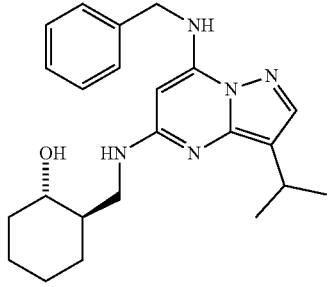

XX-02

Corresponding data for PPDA-001 and these comparison compounds are summarised in the following tables.

TABLE 5

| | IC$_{50}$ Data for Various Compounds | | | | |
|---|---|---|---|---|---|
| | In vitro Kinase Inhibition | | | Selectivity | |
| Compound | CDK1 IC$_{50}$ (nM) | CDK2 IC$_{50}$ (nM) | CDK7 IC$_{50}$ (nM) | CDK1/ CDK7 (fold) | CDK2/ CDK7 (fold) |
| PPDA-001 | 1520 | 580 | 41 | 37 | 14 |
| XX-01 | 1660 | 1520 | 310 | 5.4 | 4.9 |
| XX-02 | — | 1695 | 687 | — | 2.5 |

As can be seen from the data, PPDA-001 has a substantially greater selectivity for CKD7, as compared to both CKD1 and CKD2, than the structurally similar comparison compounds.

CDK7 selectively is desirable since CDK7 is a member of a large family of protein kinases with important developmental and cellular roles, comprising 25 members in man. CDK7 regulates cell cycle progression by phosphorylating and thereby activating cell cycle CDKs. In addition, CDK7 phosphorylates RNA polymerase II to facilitate gene transcription. Although CDK7 is an essential gene during development, in the adult CDK7 is not essential, as demonstrated in knockout mice, where its deletion demonstrates no phenotype in tissues with low proliferative index. However, re-population of cells in tissues with high cellular turnover is associated with adult stem cell depletion and premature ageing (see, e.g., Ganuza et al., 2012). Hence, treatment with CDK7 inhibitors is expected to be associated with fewer side effects.

TABLE 6

| | Growth Inhibition, GI$_{50}$ (μM) | |
|---|---|---|
| Compound No | MCF7 | HCT116 |
| PPDA-001 | 0.96 | 0.63 |
| XX-01 | 12.2 | 18.7 |
| XX-02 | 47 | >100 |

As can be seen from the data, PPDA-001 has a substantially greater growth inhibition than the structurally similar comparison compounds.

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Alarcon et al., 2009, Cell, Vol. 139, pp. 757-769.
Ali et al, 2011, Annu. Rev. Med., Vol. 62, pp. 217-232.
Ali et al., 1993, The EMBO Journal, Vol. 12, pp. 1153-1160.
Ali et al., 2002, Nat. Rev. Cancer, Vol. 2, pp. 101-112.
Ashton et al., 2004, International Patent Application Publication No. WO 2004/069162 A2, published 19 Aug. 2004.
Bartkowiak et al., 2010, Gene Dev., Vol. 24, pp. 2303-2316.
Bastien et al., 2000, J. Biol. Chem., Vol. 275, pp. 21896-21904.
Blazek et al., 2011, Gene Dev., Vol. 25, pp. 2158-2172.
Borg et al., 2000, JNCI, Vol. 92, No. 15, pp. 1260-1266.
Bosmans et al., 2005, International Patent Application Publication No. WO 2005/000838 A1, published 6 Jan. 2005.
Chen et al., 2000, Molecular Cell, Vol. 6, pp. 127-137.
Chen et al., 2002, Oncogene, Vol. 21, pp. 4921-4931.
Cheng et al., 2012, Mol. Cell. Biol., Vol. 32, pp. 4691-4704.
Chymkowitch et al., 2011, EMBO J., Vol. 30, pp. 468-490.
Claudio et al., 2006, J. Cell. Physiol., Vol. 208, pp. 602-612.
Cuzick et al., 2010, Lancet Oncol., Vol. 11, pp. 1135-1141.
Drogat et al., 2012, Cell Rep., Vol. 2, pp. 1068-1076.
Faterna et al, 2008, Cell. Mol. Neurobiol., Vol. 3, pp. 351-369.
Fisher et al., 1994, Cell, Vol. 78, pp. 713-724.
Ganuza et al., 2012, EMBO J., Vol. 31, pp. 2498-2510.
Gijsen et al., 2008, Tetrahedron, Vol. 64, pp. 2456-2464.
Gordon et al., 2010, Mol. Endocrinol., Vol. 24, pp. 2267-2280.
Guzi et al., 2004, International Patent Application Publication No. WO 2004/022561 A1, published 18 Mar. 2004.
Hansson, 2010. Adv. Exp. Med. Biol., Vol. 685, pp. 134-145.
Hong et al., 1997, Tetrahedron Letters, Vol. 38, pp. 5607-5610.
Jogalekar et al., 2008, International Patent Application Publication No. WO 2008/151304 A1, published 11 Dec. 2008.
Jogalekar et al., 2010, US Patent Publication No. 2010/0261683 A1, published 14 Oct. 2010.
Jogalekar et al., 2011, U.S. Pat. No. 8,067,424 B2, granted 29 Nov. 2011.
Johnston et al., 2003, Nat. Rev. Cancer, Vol. 3, pp. 821-831.
Jones et al., 2007, Cell, Vol. 128, pp. 683-692.
Kataoka et al., 2004, International Patent Application Publication No. WO 2004/076458 A1, published 10 Sep. 2004.
Knockaert et al., 2002, Trends Pharmacol. Sci., Vol. 23, pp. 417-425.
Ko et al., 1997, Mol. Cell. Biol., Vol. 17, No. 12, pp. 7220-7229.
Kolb et al., 1994, Chem. Rev., Vol. 94, pp. 2483-2547.
Larochelle et al., 2007, Mol. Cell, Vol. 25, pp. 839-850.
Larochelle et al., 2012, Nature Struct. Biol. Mol. Biol., Vol. 19, pp. 1108-1115.
Lorns et al., 2008, Cancer Cell, Vol. 13, pp. 91-104.
Lu et al., 1995, Nature, pp. 358, pp. 641-645.
Lu et al., 1997, Mol. Cell. Biol., Vol. 17, pp. 5923-5934.
Malumbres et al., 2001, Nature Rev. Cancer, Vol. 1, pp. 222-231.
Malumbres et al., 2009, Nature Cell Biology, Vol. 11, pp. 1275-1276.
Malumbres et al., 2009, Nature Reviews Cancer, Vol. 9, pp. 153-166.
Marshall et al., 2006, Nephron. Exp. Nephrol., Vol. 102, No. 2, pp. e39-e48.
Monaco et al., 2005, Front. Biosci., Vol. 10, No. 1, pp. 143-159.
Morgan, 1995, Nature, Vol. 374, pp. 131-134.
Moriarty et al., 2001, International Patent Application Publication No. WO 2001/047897 A1, published 5 Jul. 2001.
Nagel et al., 1984, Angew. Chemie, Vol. 96, pp. 425-426.
Ortega et al, 2002, Biochim. Biophys. Acta, Vol. 1602, pp. 73-87.
Osborne et al., 2011, Annu. Rev. Med., Vol. 62, pp. 233-247.
Osborne, 1998, The New England Journal of Medicine, Vol. 339, pp. 1609-1618.
Parratt et al., 2004, International Patent Application Publication No. WO 2004/087707 A1, published 14 Oct. 2004.
Pines, 1995, Biochem. J., Vol. 308, pp. 697-711.
Radhakrishnan et al., 2006, Cell Cycle, Vol. 5, pp. 519-521.
Rochette-Egly et al., 1997, Cell, Vol. 90, pp. 97-107.
Sengupta et al., 2012, International Patent Application Publication No. WO 2012/059932 A1, published 10 May 2012.
Serizawa et al., 1995, Nature, Vol. 374, pp. 283-287.
Sherr et al., 1995, Genes Dev., Vol. 9, pp. 1149-1163.
Skehan et al., 1990, J. Natl. Cancer Inst., Vol. 82, pp. 1107-1112.
Vince et al., 1991, J. Med. Chem., Vol. 34, pp. 2787-2797.
Wang et al., 2008, Trends Pharmacol. Sci., Vol. 29, pp. 302-312.
Xu et al., 2011, J. Genet. Genomics, Vol. 38, pp. 439-452.
Xu et al., 2011, Tetrahedron Letters, Vol. 52, pp. 3266-3270.
Yu et al., 2012, Oncol. Rep., Vol. 27, pp. 1266-1276.
Zuo et al., 1996, Nature Genetics, Vol. 12, pp. 97-99.

The invention claimed is:
1. A method of inhibiting the progress of colorectal cancer, reducing the rate of progress of colorectal cancer, halting the rate of progress of colorectal cancer, alleviating symptoms of colorectal cancer, and/or ameliorating colorectal cancer, comprising administering to a subject in need of treatment a therapeutically-effective amount of a compound of the following formula:

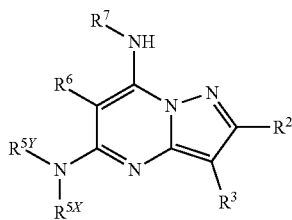

or a pharmaceutically acceptable salt thereof;
wherein:
—$R^{5X}$ is -$L^{5X}$-Q;
-$L^{5X}$- is independently a covalent single bond or -$L^{5XA}$-;
-$L^{5XA}$- is independently linear or branched saturated $C_{1-6}$alkylene, and is optionally substituted with one or more groups selected from —OH and —$OR^{L5X}$, wherein each —$R^{L5X}$ is independently linear or branched saturated $C_{1-6}$alkyl or saturated $C_{3-6}$cycloalkyl;
-Q is pyrrolidinyl, piperidinyl, morpholinyl, piperazinyl, azepanyl, or diazepanyl, wherein the point of attachment is via a ring carbon atom, and is substituted with "n" groups -J, and is substituted with "m" groups —$R^Q$;
"n" is 1, 2, or 3;
"m" is 0, 1, 2, or 3;
each -J is independently —OH, —$OR^J$, -$L^J$-OH, or -$L^J$-$OR^J$;
each —$R^J$ is independently linear or branched saturated $C_{1-6}$alkyl or saturated $C_{3-6}$cycloalkyl;
each -$L^J$- is independently linear or branched saturated $C_{1-6}$alkylene;
each —$R^Q$ is independently —F, —Cl, —Br, —I, —$R^{QA}$, —$CF_3$, —$OCF_3$, —$NH_2$, —$NHR^{QA}$, —$NR^{QA}{}_2$, pyrrolidino, piperidino, morpholino, piperazino, N—($R^{QA}$)-piperazino, —SH, —$SR^{QA}$, or —CN;
each —$R^{QA}$ is independently linear or branched saturated $C_{1-6}$alkyl or saturated $C_{3-6}$cycloalkyl;
—$R^{5Y}$ is independently —H or —$R^{5YA}$;
—$R^{5YA}$ is independently linear or branched saturated $C_{1-6}$alkyl;
—$R^7$ is independently —$R^{7X}$ or —C(=O)$R^{7X}$;
each —$R^{7X}$ is independently:
—$R^{7A}$, —$R^{7B}$, —$R^{7C}$, —$R^{7D}$, —$R^{7E}$, -$L^7$-$R^{7B}$, -$L^7$-$R^{7C}$, -$L^7$-$R^{7D}$, or -$L^7$-$R^{7E}$;
each -$L^7$- is independently linear or branched saturated $C_{1-6}$alkylene;
each —$R^{7A}$ is independently linear or branched saturated $C_{1-6}$alkyl, and is optionally substituted with one or more substituents —$W^1$;
each —$R^{7B}$ is saturated $C_{3-6}$cycloalkyl, and is optionally substituted with one or more substituents —$W^2$;
each —$R^{7C}$ is non-aromatic $C_{3-7}$heterocyclyl, and is optionally substituted with one or more substituents —$W^2$;
each —$R^{7D}$ is phenyl or naphthyl, and is optionally substituted with one or more substituents —$W^3$;
each —$R^{7E}$ is $C_{5-12}$heteroaryl, and is optionally substituted with one or more substituents —$W^3$;
each —$W^1$ is independently:
—F, —Cl, —Br, —I, —$CF_3$, —OH, —$OR^{W1}$, —$OCF_3$, —$NH_2$, —$NHR^{W1}$, —$NR^{W1}{}_2$, pyrrolidino, piperidino, morpholino, piperazino, N—($R^{W1}$)-piperazino, —C(=O)OH, —C(=O)$OR^{W1}$, —C(=O)$NH_2$, —C(=O)$NHR^{W1}$, —C(=O)$NR^{W1}{}_2$, —C(=O)-pyrrolidino, —C(=O)-piperidino, —C(=O)-morpholino, —C(=O)-piperazino, —C(=O)—N—($R^{W1}$)-piperazino, —S(=O)$R^{W1}$, —S(=O)$_2R^{W1}$, —S(=O)$_2NH_2$, —S(=O)$_2NHR^{W1}$, —S(=O)$_2NR^{W1}{}_2$, —S(=O)$_2$-pyrrolidino, —S(=O)$_2$-piperidino, —S(=O)$_2$-morpholino, —S(=O)$_2$-piperazino, —S(=O)$_2$—N—($R^{W1}$)-piperazino, —CN, or —$NO_2$;
wherein each —$R^{W1}$ is independently linear or branched saturated $C_{1-6}$alkyl, phenyl, or —$CH_2$-phenyl, wherein each phenyl is optionally substituted with one or more groups selected from —F, —Cl, —Br, —I, —$R^{W11}$, —$CF_3$, —OH, —$OR^{W11}$, and —$OCF_3$, wherein each —$R^{W11}$ is independently linear or branched saturated $C_{1-6}$alkyl;
each —$W^2$ is independently:
—F, —Cl, —Br, —I, —$R^{W2}$, —$CF_3$, —OH, —$OR^{W2}$, —$OCF_3$, —$NH_2$, —$NHR^{W2}$, —$NR^{W2}{}_2$, pyrrolidino, piperidino, morpholino, piperazino, N—($R^{W2}$)-piperazino, —C(=O)OH, —C(=O)$OR^{W2}$, —C(=O)$NH_2$, —C(=O)$NHR^{W2}$, —C(=O)$NR^{W2}{}_2$, —C(=O)-pyrrolidino, —C(=O)-piperidino, —C(=O)-morpholino, —C(=O)-piperazino, —C(=O)—N—($R^{W2}$)-piperazino, —S(=O)$R^{W2}$, —S(=O)$_2R^{W2}$, —S(=O)$_2NH_2$, —S(=O)$_2NHR^{W2}$, —S(=O)$_2NR^{W2}{}_2$, —S(=O)$_2$-pyrrolidino, —S(=O)$_2$-piperidino, —S(=O)$_2$-morpholino, —S(=O)$_2$-piperazino, —S(=O)$_2$—N—($R^{W2}$)-piperazino, —CN, or —$NO_2$;
wherein each —$R^{W2}$ is independently linear or branched saturated $C_{1-6}$alkyl, phenyl, or —$CH_2$-phenyl, wherein each phenyl is optionally substituted with one or more groups selected from —F, —Cl, —Br, —I, —$R^{W22}$, —$CF_3$, —OH, —$OR^{W22}$, and —$OCF_3$, wherein each —$R^{W22}$ is independently linear or branched saturated $C_{1-6}$alkyl;
each —$W^3$ is independently:
—F, —Cl, —Br, —I, —$R^{W3}$, —$CF_3$, —OH, —$OR^{W3}$, —$OCF_3$, —$NH_2$, —$NHR^{W3}$, —$NR^{W3}{}_2$, pyrrolidino, piperidino, morpholino, piperazino, N—($R^{W3}$)-piperazino, —C(=O)OH, —C(=O)$OR^{W3}$, —C(=O)$NH_2$, —C(=O)$NHR^{W3}$, —C(=O)$NR^{W3}{}_2$, —C(=O)-pyrrolidino, —C(=O)-piperidino, —C(=O)-morpholino, —C(=O)-piperazino, —C(=O)—N—($R^{W3}$)-piperazino, —S(=O)$R^{W3}$, —S(=O)$_2R^{W3}$, —S(=O)$_2NH_2$, —S(=O)$_2NHR^{W3}$, —S(=O)$_2NR^{W3}{}_2$, —S(=O)$_2$-pyrrolidino, —S(=O)$_2$-piperidino, —S(=O)$_2$-morpholino, —S(=O)$_2$-piperazino, —S(=O)$_2$—N—($R^{W3}$)-piperazino, —CN, or —$NO_2$;
wherein each —$R^{W3}$ is independently linear or branched saturated $C_{1-6}$alkyl, phenyl, or —$CH_2$-phenyl, wherein each phenyl is optionally substituted with one or more groups selected from —F, —Cl, —Br, —I, —$R^{W33}$, —$CF_3$, —OH, —$OR^{W33}$, and —$OCF_3$, wherein each —$R^{W33}$ is independently linear or branched saturated $C_{1-6}$alkyl;
—$R^3$ is independently —$R^{3A}$ or —$R^{3B}$;
—$R^{3A}$ is independently linear or branched saturated $C_{1-6}$alkyl;
—$R^{3B}$ is independently saturated $C_{3-7}$cycloalkyl;
—$R^2$ is independently —H or —$R^{2A}$;
—$R^{2A}$ is independently —F, —Cl, —Br, —I, —$R^{2AA}$, —$CF_3$, —OH, —$OR^{2AA}$, —$OCF_3$, —$NH_2$, —$NHR^{2AA}$, —$NR^{2AA}{}_2$, pyrrolidino, piperidino, morpholino, piperazino, N—($R^{2AA}$)-piperazino, —SH, —$SR^{2AA}$, or —CN;
each —$R^{2AA}$ is independently linear or branched saturated $C_{1-6}$alkyl;
—$R^6$ is independently —H or —$R^{6A}$;
—$R^{6A}$ is independently —F, —Cl, —Br, —I, —$R^{6AA}$, —$CF_3$, —OH, —$OR^{6AA}$, —$OCF_3$, —$NH_2$, —$NHR^{6AA}$, —NR$^{6AA}{}_2$, pyrrolidino, piperidino, morpholino, piperazino, N—(R$^{6AA}$)-piperazino, —SH, —SR$^{6AA}$, or —CN; and each —R$^{6AA}$ is independently linear or branched saturated C$_{1-6}$alkyl.

2. A method according to claim 1, wherein:
—R$^{5Y}$ is —H;
—R$^2$ is —H; and
—R$^6$ is —H.

3. A method according to claim 2, wherein:
-L$^{5X}$- is independently a covalent single bond or -L$^{5XA}$-; and
-L$^{5XA}$- is —CH$_2$—.

4. A method according to claim 3, wherein:
-Q is pyrrolidinyl, wherein the point of attachment is via a ring carbon atom, and is substituted with "n" groups -J, and is substituted with "m" groups —R$^Q$; or
-Q is piperidinyl, wherein the point of attachment is via a ring carbon atom, and is substituted with "n" groups -J, and is substituted with "m" groups —R$^Q$.

5. A method according to claim 3, wherein -Q is selected from:

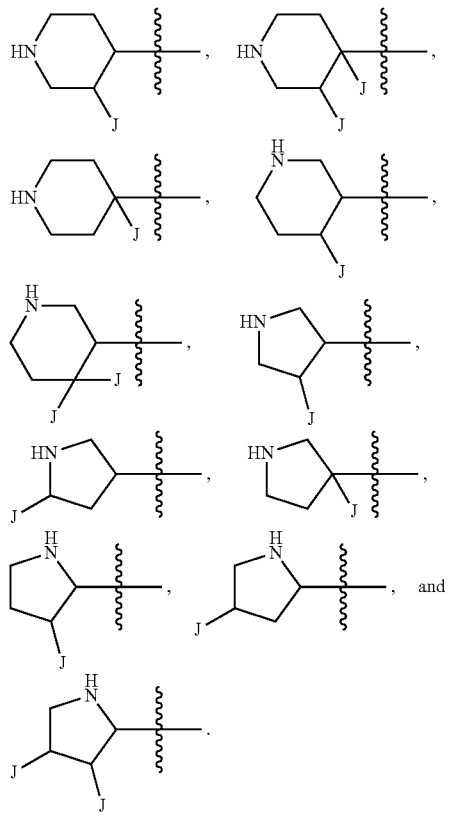

6. A method according to claim 3, wherein -Q is:

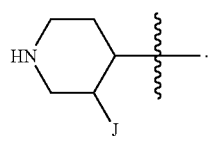

7. A method according claim 4, wherein each -J is —OH.
8. A method according claim 5, wherein each -J is —OH.
9. A method according claim 6, wherein each -J is —OH.
10. A method according to claim 7, wherein —R$^3$ is —R$^{3A}$; and —R$^{3A}$ is -iPr.
11. A method according to claim 8, wherein —R$^3$ is —R$^{3A}$; and —R$^{3A}$ is -iPr.
12. A method according to claim 9, wherein —R$^3$ is —R$^{3A}$; and —R$^{3A}$ is -iPr.
13. A method according to claim 4, wherein —R$^7$ is —R$^{7X}$; and —R$^{7X}$ is independently: R$^{7C}$, —R$^{7D}$, —R$^{7E}$, -L$^7$-R$^{7B}$, L$^7$-R$^{7D}$, or -L$^7$-R$^{7E}$.
14. A method according to claim 7, wherein —R$^7$ is —R$^{7X}$; and —R$^{7X}$ is independently: —R$^{7C}$, —R$^{7D}$, R$^{7E}$, -L$^7$-R$^{7B}$, -L$^7$-R$^{7D}$, or L$^7$-R$^{7E}$.
15. A method according to claim 10, wherein —R$^7$ is —R$^{7X}$; and —R$^{7X}$ is independently: —R$^{7C}$, —R$^{7D}$, —R$^{7E}$, -L$^7$-R$^{7B}$, -L$^7$-R$^{7D}$, or -L$^7$-R$^{7E}$.
16. A method according to claim 12, wherein —R$^7$ is —R$^{7X}$; and —R$^{7X}$ is independently: —R$^{7C}$, —R$^{7D}$, —R$^{7E}$, -L$^7$-R$^{7B}$, -L$^7$-R$^{7D}$, or -L$^7$-R$^{7E}$.
17. A method according to claim 4, wherein:
—R$^7$ is —R$^{7X}$;
—R$^{7X}$ is independently: —R$^{7C}$, —R$^{7D}$, —R$^{7E}$, -L$^7$-R$^{7B}$, -L$^7$-R$^{7D}$, or -L$^7$-R$^{7E}$;
each -L$^7$- is —CH$_2$—;
each —R$^{7B}$ is cyclohexyl, and is optionally substituted with one or more substituents —W$^2$;
each —R$^{7C}$ is independently piperidinyl, and is optionally substituted with one or more substituents —W$^2$;
each —R$^{7D}$ is phenyl, and is optionally substituted with one or more substituents —W$^3$; and
each —R$^{7E}$ is pyridyl, and is optionally substituted with one or more substituents —W$^3$;
wherein:
each —W$^2$ is independently: —F, —Cl, —Br, —I, —CF$_3$, —OH, —OR$^{W2}$, —OCF$_3$, or —CN;
each —R$^{W2}$ is independently linear or branched saturated C$_{1-4}$alkyl;
each —W$^3$ is independently: —F, —Cl, —Br, —I, —CF$_3$, —OH, —OR$^{W3}$, —OCF$_3$, or —CN; and
each —R$^{W3}$ is independently linear or branched saturated C$_{1-4}$alkyl.
18. A method according to claim 4, wherein:
—R$^7$ is —R$^{7X}$;
—R$^{7X}$ is -L$^7$-R$^{7D}$;
-L$^7$- is —CH$_2$—;
—R$^{7D}$ is phenyl, and is optionally substituted with one or more substituents —W$^3$;
each —W$^3$ is independently: —F, —Cl, —Br, —I, —CF$_3$, —OH, —OR$^{W3}$, —OCF$_3$, or —CN; and
each —R$^{W3}$ is independently linear or branched saturated C$_{1-4}$alkyl.
19. A method according to claim 6, wherein:
—R$^7$ is —R$^{7X}$;
—R$^{7X}$ is -L$^7$-R$^{7D}$;
-L$^7$- is —CH$_2$—;
—R$^{7D}$ is phenyl, and is optionally substituted with one or more substituents —W$^3$;
each —W$^3$ is independently: —F, —Cl, —Br, —I, —CF$_3$, —OH, —OR$^{W3}$, —OCF$_3$, or —CN; and
each —R$^{W3}$ is independently linear or branched saturated C$_{1-4}$alkyl.
20. A method according to claim 7, wherein:
—R$^7$ is —R$^{7X}$;
—R$^{7X}$ is -L$^7$-R$^{7D}$;
-L$^7$- is —CH$_2$—;

—R[7D] is phenyl, and is optionally substituted with one or more substituents —W³;

each —W³ is independently: —F, —Cl, —Br, —I, —CF₃, —OH, —OR^{W3}, —OCF₃, or —CN; and each —R^{W3} is independently linear or branched saturated C₁₋₄alkyl.

21. A method according to claim 9, wherein:
—R⁷ is —R[7X];
—R[7X] is -L⁷-R[7D];
-L⁷- is —CH₂—;
—R[7D] is phenyl, and is optionally substituted with one or more substituents —W³;
each —W³ is independently: —F, —Cl, —Br, —I, —CF₃, —OH, —OR^{W3}, —OCF₃, or —CN; and
each —R^{W3} is independently linear or branched saturated C₁₋₄alkyl.

22. A method according to claim 10, wherein:
—R⁷ is —R[7X];
—R[7X] is -L⁷-R[7D];
-L⁷- is —CH₂—;
—R[7D] is phenyl, and is optionally substituted with one or more substituents —W³;
each —W³ is independently: —F, —Cl, —Br, —I, —CF₃, —OH, —OR^{W3}, —OCF₃, or —CN; and
each —R^{W3} is independently linear or branched saturated C₁₋₄alkyl.

23. A method according to claim 12, wherein:
—R⁷ is —R[7X];
—R[7X] is -L⁷-R[7D];
-L⁷- is —CH₂—;
—R[7D] is phenyl, and is optionally substituted with one or more substituents —W³;
each —W³ is independently: —F, —Cl, —Br, —I, —CF₃, —OH, —OR^{W3}, —OCF₃, or —CN; and
each —R^{W3} is independently linear or branched saturated C₁₋₄alkyl.

24. A method according to claim 23, wherein -L[5X]- is -L[5XA]-.

25. A method of inhibiting the progress of colorectal cancer, reducing the rate of progress of colorectal cancer, halting the rate of progress of colorectal cancer, alleviating symptoms of colorectal cancer, and/or ameliorating colorectal cancer, comprising administering to a subject in need of treatment a therapeutically-effective amount of a compound selected from compounds of the following formulas and pharmaceutically acceptable salts thereof:

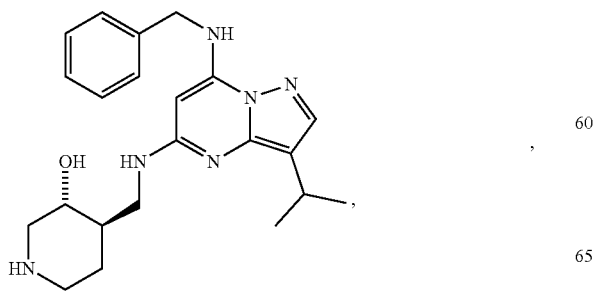

(PPDA-001)

-continued

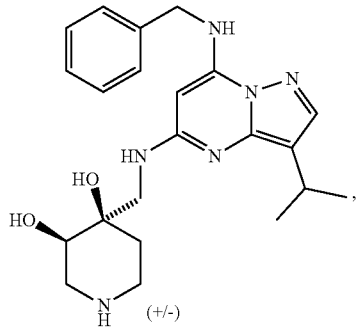

(PPDA-002)

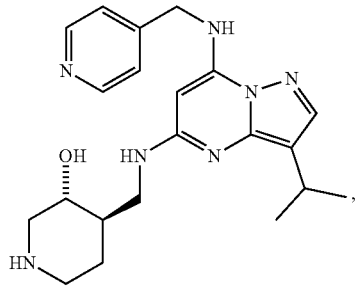

(PPDA-003)

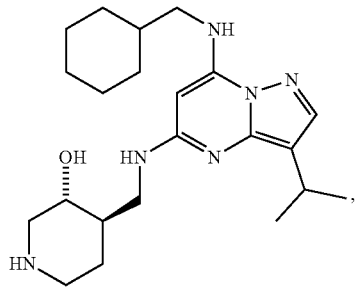

(PPDA-004)

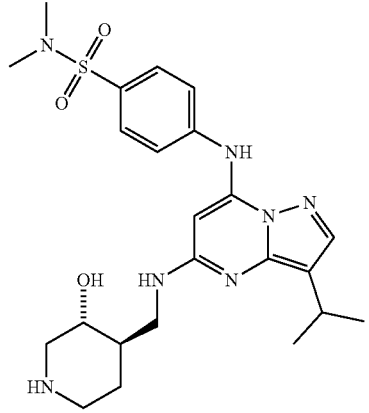

(PPDA-005)

-continued
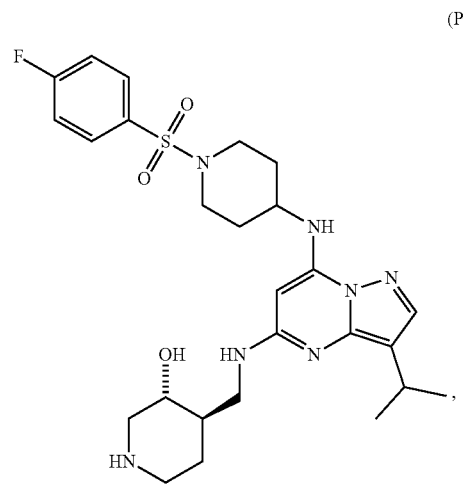
(PPDA-006)
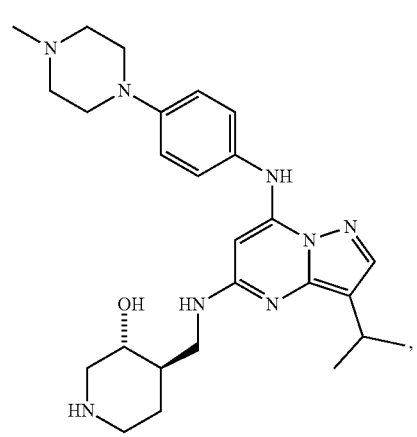
(PPDA-007)
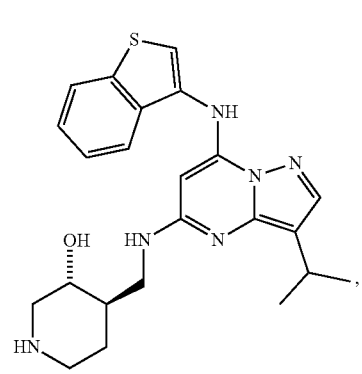
(PPDA-008)
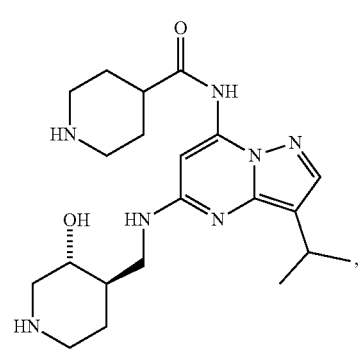
(PPDA-009)
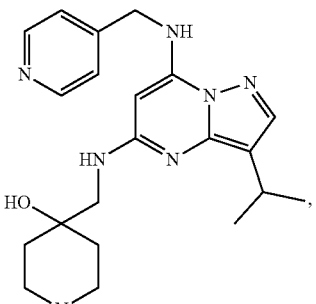
(PPDA-010)
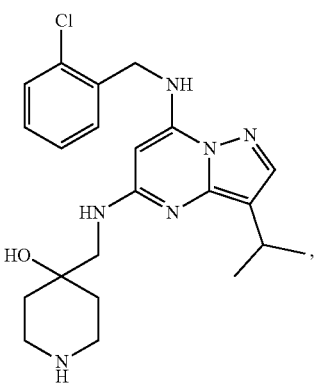
(PPDA-011)
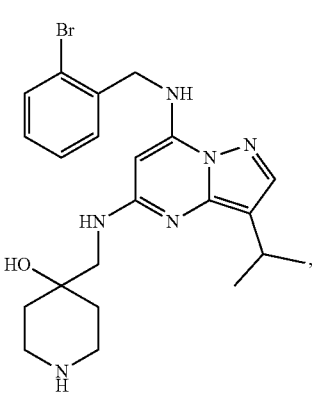
(PPDA-012)
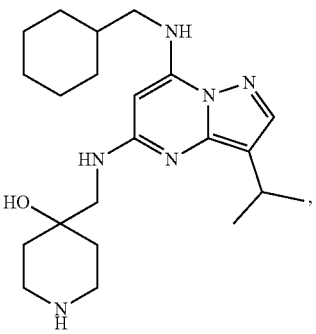
(PPDA-013)

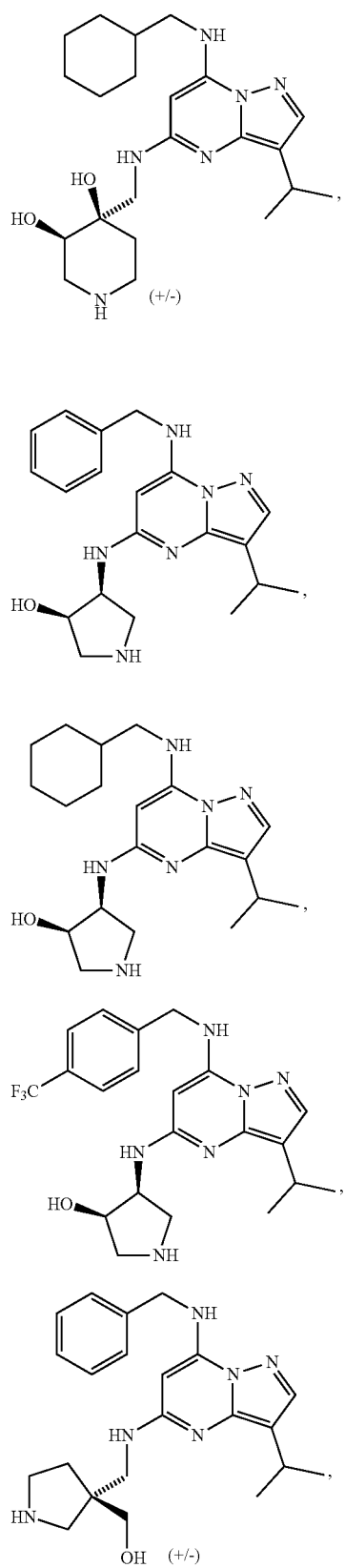
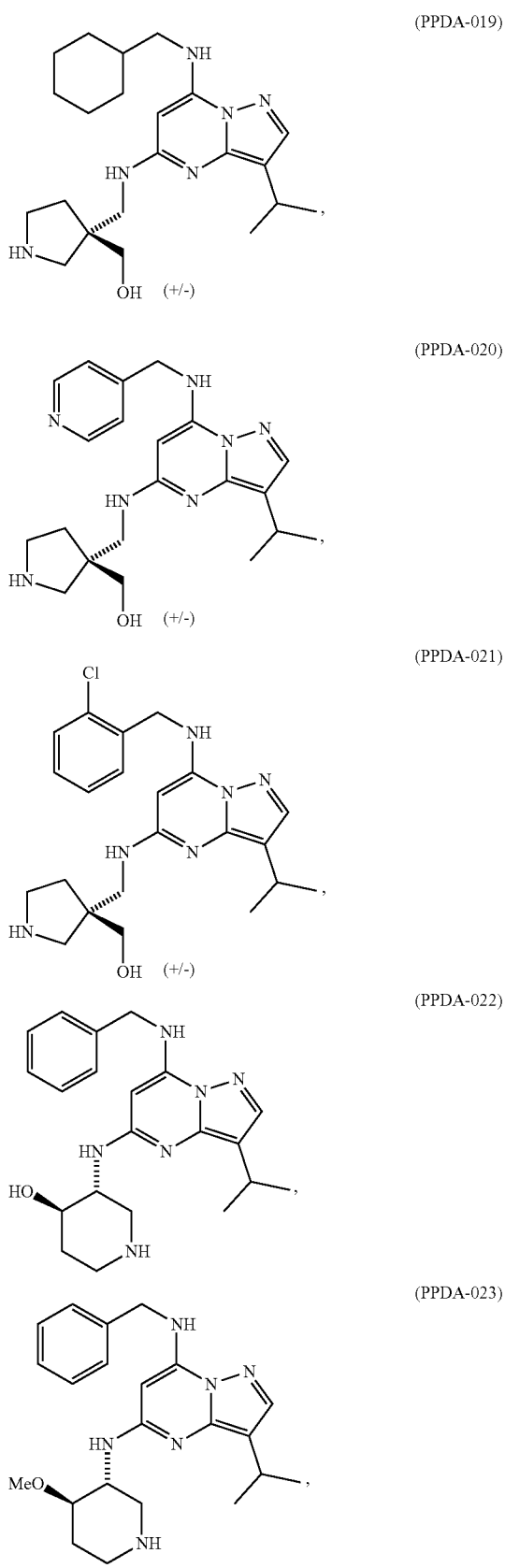

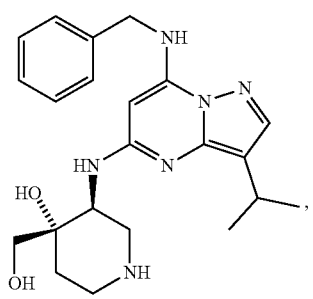 (PPDA-024)

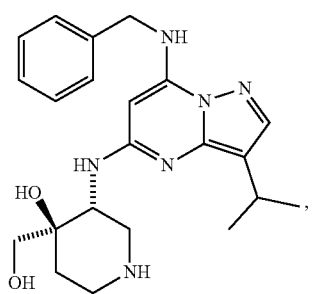 (PPDA-025)

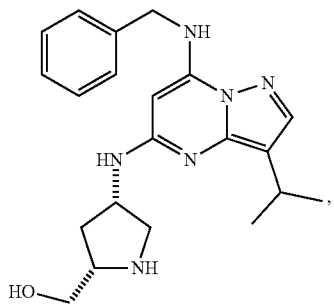 (PPDA-026)

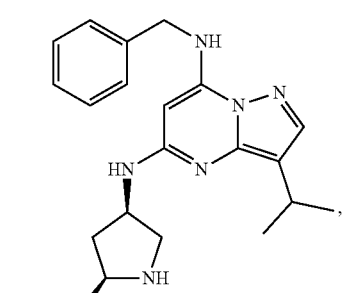 (PPDA-027)

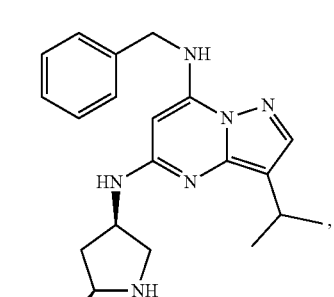 (PPDA-028)

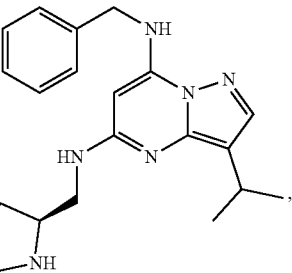 (PPDA-029)

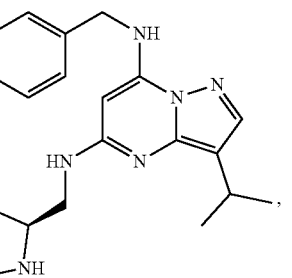 (PPDA-030)

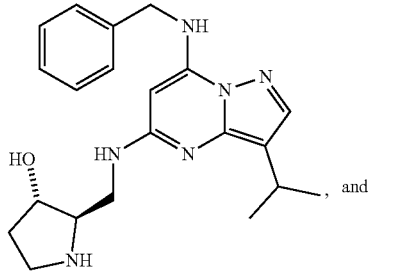 (PPDA-031)

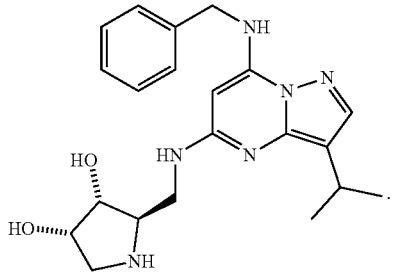 (PPDA-032)

26. A method of inhibiting the progress of colorectal cancer, reducing the rate of progress of colorectal cancer, halting the rate of progress of colorectal cancer, alleviating symptoms of colorectal cancer, and/or ameliorating colorectal cancer, comprising administering to a subject in need of treatment a therapeutically-effective amount of a compound selected from a compound of the following formula and pharmaceutically acceptable salts thereof:

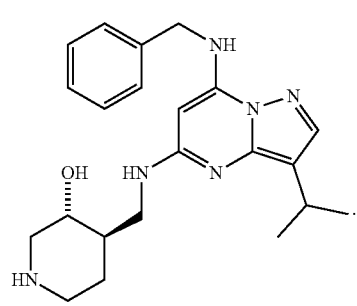
(PPDA-001)
* * * * *